United States Patent
Callewaert et al.

(10) Patent No.: US 11,293,012 B2
(45) Date of Patent: Apr. 5, 2022

(54) CELLS PRODUCING GLYCOPROTEINS HAVING ALTERED N- AND O-GLYCOSYLATION PATTERNS AND METHODS AND USE THEREOF

(71) Applicants: VIB VZW, Ghent (BE); Universiteit Gent, Ghent (BE)

(72) Inventors: Nico Callewaert, Nevele (BE); Leander Meuris, Ghent (BE); Francis Santens, Ghent (BE)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 0 days.

(21) Appl. No.: 15/741,025

(22) PCT Filed: Jul. 8, 2016

(86) PCT No.: PCT/EP2016/066362
§ 371 (c)(1),
(2) Date: Dec. 29, 2017

(87) PCT Pub. No.: WO2017/005925
PCT Pub. Date: Jan. 12, 2017

(65) Prior Publication Data
US 2018/0187177 A1    Jul. 5, 2018

(30) Foreign Application Priority Data
Jul. 9, 2015   (EP) ..................... 15176111

(51) Int. Cl.
| | | |
|---|---|---|
| *C12N 9/24* | (2006.01) | |
| *C12P 21/00* | (2006.01) | |
| *C12N 9/90* | (2006.01) | |
| *C07K 14/505* | (2006.01) | |
| *C07K 14/535* | (2006.01) | |
| *C07K 14/005* | (2006.01) | |
| *C07K 14/715* | (2006.01) | |

(52) U.S. Cl.
CPC .......... *C12N 9/2402* (2013.01); *C07K 14/005* (2013.01); *C07K 14/505* (2013.01); *C07K 14/535* (2013.01); *C07K 14/7151* (2013.01); *C12N 9/90* (2013.01); *C12P 21/005* (2013.01); *C12Y 204/99001* (2013.01); *C12Y 302/01096* (2013.01); *C12Y 501/03002* (2013.01); *C07K 2319/02* (2013.01); *C07K 2319/21* (2013.01); *C07K 2319/30* (2013.01); *C12N 2760/00051* (2013.01)

(58) Field of Classification Search
None
See application file for complete search history.

(56) References Cited

U.S. PATENT DOCUMENTS

| | | | |
|---|---|---|---|
| 5,721,121 A | 2/1998 | Etcheverry et al. | |
| 7,244,619 B2 | 7/2007 | Contreras et al. | |
| 7,335,512 B2 | 2/2008 | Callewaert et al. | |
| 8,815,544 B2* | 8/2014 | Davidson ............. | C12N 9/1051 435/72 |
| 8,815,580 B2* | 8/2014 | Callewaert ..... | C12Y 302/01096 435/254.1 |
| 2006/0148039 A1 | 7/2006 | Kobayashi et al. | |
| 2013/0137140 A1 | 5/2013 | Callewaert et al. | |
| 2014/0345004 A1 | 11/2014 | Callewaert et al. | |
| 2014/0357521 A1 | 12/2014 | Steyaert et al. | |
| 2016/0200825 A1 | 7/2016 | Callewaert et al. | |

FOREIGN PATENT DOCUMENTS

| | | |
|---|---|---|
| EP | 549062 B1 | 3/1999 |
| EP | 1211310 B1 | 12/2006 |
| WO | 0200879 A2 | 1/2002 |
| WO | 0248187 A2 | 6/2002 |
| WO | 03046150 A2 | 6/2003 |
| WO | 2006050584 A1 | 5/2006 |
| WO | 2007133855 A2 | 11/2007 |
| WO | 2010015722 A1 | 2/2010 |
| WO | 2017005925 A1 | 1/2017 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Edge, Deglycosylation of glycoproteins with trifluoromethanesulphonic acid: elucidation of molecular structure and function, Biochemical Journal, Dec. 1, 2003, pp. 339-350, vol. 376, No. 2.
Kingsley et al., Reversible defects in O-linked glycosylation and LDL receptor expression in a UDP-GalUDP-GalNAc 4-epimerase deficient mutant, Cell, Mar. 14, 1986, pp. 749-749, vol. 44, No. 5, Cell Press, US.
Kwon et al., The Effect of gale Gene Inactivation on Lipopolysaccharide Profile of Helicobacter pylori, Current Microbiology, Aug. 1, 1998, pp. 144-148, vol. 37, No. 2.

(Continued)

*Primary Examiner* — Richard G Hutson
(74) *Attorney, Agent, or Firm* — Patent Law Works, LLP

(57) ABSTRACT

The present application relates to the field of glyco-engineering and, more specifically, to eukaryotic cells wherein both an endoglucosaminidase is present and made deficient in UDP-galactose 4-epimerase (GalE). Typically, a glycoprotein is also present in the cells. These cells can be used to deglycosylate or partly deglycosylate the (exogenous) glycoprotein, in particular, without the need for adding an extra enzyme. Methods are also provided for the application of these cells in protein production.

10 Claims, 16 Drawing Sheets

Specification includes a Sequence Listing.

(56) References Cited

OTHER PUBLICATIONS

Meuris et al., GlycoDelete engineering of mammalian cells simplifies N-Glycosylation of recombinant proteins, Nature Biotechnology, Apr. 20, 2014, pp. 485-489, vol. 32, No. 5.
PCT International Search Report, PCT/EP2016/066362, dated Sep. 29, 2016.
PCT International Written Opinion, PCT/EP2016/066362, dated Sep. 29, 2016.
Sanders et al., UDP-galactose 4' epimerase (GALE) is essential for development of *Drosophila melanogaster*, Disease Models & Mechanisms, Jun. 2, 2010, pp. 628-638, vol. 3, No. 9-10.
Kingsley et al., "Three Types of Low Denisty Lipoprotein Receptor-deficeint Mutant Have Pleiotropic Defects in the Synthesis of N-linked, O-linked, and Lipid-linked Carbohydrate Chains," The Rockefeller University Press, The Journal of Cell Biology, vol. 102, May 1986; pp. 1576-1585.

\* cited by examiner

○ Mannose
■ GlcNAc
━━ Peptide backbone

SEQUENCE LISTING

<160> NUMBER OF SEQ ID NOS: 53

<210> SEQ ID NO 1
<211> LENGTH: 4
<212> TYPE: PRT
<213> ORGANISM: Artificial Sequence
<220> FEATURE:
<223> OTHER INFORMATION: consensus sequence

<400> SEQUENCE: 1

Lys Asp Glu Leu

```
<210> SEQ ID NO 2
<211> LENGTH: 4
<212> TYPE: PRT
<213> ORGANISM: Artificial Sequence
<220> FEATURE:
<223> OTHER INFORMATION: consensus sequence

<400> SEQUENCE: 2

His Asp Glu Leu
1

<210> SEQ ID NO 3
<211> LENGTH: 19
<212> TYPE: PRT
<213> ORGANISM: Artificial Sequence
<220> FEATURE:
<223> OTHER INFORMATION: tryptic peptide

<400> SEQUENCE: 3

Ser Pro Ser Pro Ser Thr Gln Pro Trp Glu His Val Asn Ala Ile Gln
1               5                   10                  15

Glu Ala Arg

<210> SEQ ID NO 4
<211> LENGTH: 6
<212> TYPE: PRT
<213> ORGANISM: Artificial Sequence
<220> FEATURE:
<223> OTHER INFORMATION: sialidase treated peptide

<400> SEQUENCE: 4

Leu Leu Asn Leu Ser Arg
1               5

<210> SEQ ID NO 5
<211> LENGTH: 15
<212> TYPE: PRT
<213> ORGANISM: Artificial Sequence
<220> FEATURE:
<223> OTHER INFORMATION: tryptic peptide

<400> SEQUENCE: 5

Glu Ala Ile Ser Pro Pro Asp Ala Ala Ser Ala Ala Pro Leu Arg
1               5                   10                  15

<210> SEQ ID NO 6
<211> LENGTH: 20
<212> TYPE: DNA
<213> ORGANISM: Artificial Sequence
<220> FEATURE:
<223> OTHER INFORMATION: oligo

<400> SEQUENCE: 6
tggaagttat cgatgaccac                                              20

<210> SEQ ID NO 7
<211> LENGTH: 20
<212> TYPE: DNA
<213> ORGANISM: Artificial Sequence
<220> FEATURE:
<223> OTHER INFORMATION: oligo

<400> SEQUENCE: 7
gtggtcatcg ataacttcca                                              20
```

<210> SEQ ID NO 8
<211> LENGTH: 20
<212> TYPE: DNA
<213> ORGANISM: Artificial Sequence
<220> FEATURE:
<223> OTHER INFORMATION: oligo

<400> SEQUENCE: 8 cttttgaag agacgctgta                                         20

<210> SEQ ID NO 9
<211> LENGTH: 20
<212> TYPE: DNA
<213> ORGANISM: Artificial Sequence
<220> FEATURE:
<223> OTHER INFORMATION: oligo

<400> SEQUENCE: 9
tacagcgtct cttcaaaaag                                        20

<210> SEQ ID NO 10
<211> LENGTH: 20
<212> TYPE: DNA
<213> ORGANISM: Artificial Sequence
<220> FEATURE:
<223> OTHER INFORMATION: oligo

<400> SEQUENCE: 10
cttctgcacc gactcgccca                                        20

<210> SEQ ID NO 11
<211> LENGTH: 20
<212> TYPE: DNA
<213> ORGANISM: Artificial Sequence
<220> FEATURE:
<223> OTHER INFORMATION: oligo

<400> SEQUENCE: 11
tgggcgagtc ggtgcagaag                                        20

<210> SEQ ID NO 12
<211> LENGTH: 26
<212> TYPE: DNA
<213> ORGANISM: Artificial Sequence
<220> FEATURE:
<223> OTHER INFORMATION: primer

<400> SEQUENCE: 12
agcctatgga aaacgccag caacgc                                  26

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
gtgtagtggc ctgatttggc tcac                                   24

<210> SEQ ID NO 14
<211> LENGTH: 22
<212> TYPE: DNA
<213> ORGANISM: Artificial Sequence
<220> FEATURE:

<223> OTHER INFORMATION: primer

<400> SEQUENCE: 14
gtgggaagga agctctgagc ag                                              22

<210> SEQ ID NO 15
<211> LENGTH: 40
<212> TYPE: DNA
<213> ORGANISM: Artificial Sequence
<220> FEATURE:
<223> OTHER INFORMATION: primer

<400> SEQUENCE: 15
taatacgact cactataggg tggaagttat cgatgaccac                            40

<210> SEQ ID NO 16
<211> LENGTH: 40
<212> TYPE: DNA
<213> ORGANISM: Artificial Sequence
<220> FEATURE:
<223> OTHER INFORMATION: primer

<400> SEQUENCE: 16
taatacgact cactataggg cttttgaag agacgctgta                             40

<210> SEQ ID NO 17
<211> LENGTH: 40
<212> TYPE: DNA
<213> ORGANISM: Artificial Sequence
<220> FEATURE:
<223> OTHER INFORMATION: primer

<400> SEQUENCE: 17
taatacgact cactataggg cttctgcacc gactcgccca                            40

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
aaaagcaccg actcggtgcc                                                  20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
tgatctcctc acctcggcct                                                  20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
acactgccgc ctccttccaa                                                  20

<210> SEQ ID NO 21
<211> LENGTH: 26
<212> TYPE: DNA
<213> ORGANISM: Artificial Sequence
<220> FEATURE:
<223> OTHER INFORMATION: primer

<400> SEQUENCE: 21
tgacctctgc ctcacacatt actccc                                    26

<210> SEQ ID NO 22
<211> LENGTH: 25
<212> TYPE: DNA
<213> ORGANISM: Artificial Sequence
<220> FEATURE:
<223> OTHER INFORMATION: primer

<400> SEQUENCE: 22
ctggacaaca gagcgagact gtcaa                                     25

<210> SEQ ID NO 23
<211> LENGTH: 25
<212> TYPE: DNA
<213> ORGANISM: Artificial Sequence
<220> FEATURE:
<223> OTHER INFORMATION: oligo

<400> SEQUENCE: 23
caccgtggaa gttatcgatg accac                                     25

<210> SEQ ID NO 24
<211> LENGTH: 25
<212> TYPE: DNA
<213> ORGANISM: Artificial Sequence
<220> FEATURE:
<223> OTHER INFORMATION: oligo

<400> SEQUENCE: 24
aaacgtggtc atcgataact tccac                                     25

<210> SEQ ID NO 25
<211> LENGTH: 25
<212> TYPE: DNA
<213> ORGANISM: Artificial Sequence
<220> FEATURE:
<223> OTHER INFORMATION: oligo

<400> SEQUENCE: 25 caccgcttt tgaagagacg ctgta                                      25

<210> SEQ ID NO 26
<211> LENGTH: 25
<212> TYPE: DNA
<213> ORGANISM: Artificial Sequence
<220> FEATURE:
<223> OTHER INFORMATION: oligo

<400> SEQUENCE: 26
aaactacagc gtctcttcaa aaagc                                     25

<210> SEQ ID NO 27
<211> LENGTH: 25
<212> TYPE: DNA
<213> ORGANISM: Artificial Sequence
<220> FEATURE:
<223> OTHER INFORMATION: oligo

<400> SEQUENCE: 27
caccgcttct gcaccgactc gccca    25

<210> SEQ ID NO 28
<211> LENGTH: 25
<212> TYPE: DNA
<213> ORGANISM: Artificial Sequence
<220> FEATURE:
<223> OTHER INFORMATION: oligo

<400> SEQUENCE: 28
aaactgggcg agtcggtgca gaagc    25

<210> SEQ ID NO 29
<211> LENGTH: 53
<212> TYPE: DNA
<213> ORGANISM: Artificial Sequence
<220> FEATURE:
<223> OTHER INFORMATION: primer

<400> SEQUENCE: 29
cctacacgac gctcttccga tctggtcccg gtcaggttaa ctctgtaata atc    53

<210> SEQ ID NO 30
<211> LENGTH: 45
<212> TYPE: DNA
<213> ORGANISM: Artificial Sequence
<220> FEATURE:
<223> OTHER INFORMATION: primer

<400> SEQUENCE: 30
agttcagacg tgtgctcttc cgatctgtga gtgcaggcag gcagg    45

<210> SEQ ID NO 31
<211> LENGTH: 41
<212> TYPE: DNA
<213> ORGANISM: Artificial Sequence
<220> FEATURE:
<223> OTHER INFORMATION: primer

<400> SEQUENCE: 31
cctacacgac gctcttccga tctccgctca ccacggaagg c    41

<210> SEQ ID NO 32
<211> LENGTH: 50
<212> TYPE: DNA
<213> ORGANISM: Artificial Sequence
<220> FEATURE:
<223> OTHER INFORMATION: primer

<400> SEQUENCE: 32
agttcagacg tgtgctcttc cgatctgcct cagccacctc tgagactctg    50

<210> SEQ ID NO 33
<211> LENGTH: 58
<212> TYPE: DNA
<213> ORGANISM: Artificial Sequence
<220> FEATURE:
<223> OTHER INFORMATION: primer

<400> SEQUENCE: 33
aatgatacgg cgaccaccga gatctacact cttccctac acgacgctct tccgatct    58

<210> SEQ ID NO 34
<211> LENGTH: 64

```
<212> TYPE: DNA
<213> ORGANISM: Artificial Sequence
<220> FEATURE:
<223> OTHER INFORMATION: primer

<400> SEQUENCE: 34
caagcagaag acggcatacg agatttgact gtgactggag ttcagacgtg tgctcttccg    60
atct                                                                 64

<210> SEQ ID NO 35
<211> LENGTH: 64
<212> TYPE: DNA
<213> ORGANISM: Artificial Sequence
<220> FEATURE:
<223> OTHER INFORMATION: primer

<400> SEQUENCE: 35
caagcagaag acggcatacg agatggaact gtgactggag ttcagacgtg tgctcttccg    60
atct                                                                 64

<210> SEQ ID NO 36
<211> LENGTH: 64
<212> TYPE: DNA
<213> ORGANISM: Artificial Sequence
<220> FEATURE:
<223> OTHER INFORMATION: primer

<400> SEQUENCE: 36
caagcagaag acggcatacg agattgacat gtgactggag ttcagacgtg tgctcttccg    60
atct                                                                 64

<210> SEQ ID NO 37
<211> LENGTH: 64
<212> TYPE: DNA
<213> ORGANISM: Artificial Sequence
<220> FEATURE:
<223> OTHER INFORMATION: primer

<400> SEQUENCE: 37
caagcagaag acggcatacg agatggacgg gtgactggag ttcagacgtg tgctcttccg    60
atct                                                                 64

<210> SEQ ID NO 38
<211> LENGTH: 64
<212> TYPE: DNA
<213> ORGANISM: Artificial Sequence
<220> FEATURE:
<223> OTHER INFORMATION: primer

<400> SEQUENCE: 38
caagcagaag acggcatacg agatgcggac gtgactggag ttcagacgtg tgctcttccg    60
atct                                                                 64

<210> SEQ ID NO 39
<211> LENGTH: 64
<212> TYPE: DNA
<213> ORGANISM: Artificial Sequence
<220> FEATURE:
<223> OTHER INFORMATION: primer

<400> SEQUENCE: 39
caagcagaag acggcatacg agattttcac gtgactggag ttcagacgtg tgctcttccg    60
``` atct 64

<210> SEQ ID NO 40
<211> LENGTH: 64
<212> TYPE: DNA
<213> ORGANISM: Artificial Sequence
<220> FEATURE:
<223> OTHER INFORMATION: primer

<400> SEQUENCE: 40
caagcagaag acggcatacg agatggccac gtgactggag ttcagacgtg tgctcttccg    60
atct    64

<210> SEQ ID NO 41
<211> LENGTH: 64
<212> TYPE: DNA
<213> ORGANISM: Artificial Sequence
<220> FEATURE:
<223> OTHER INFORMATION: primer

<400> SEQUENCE: 41
caagcagaag acggcatacg agatcgaaac gtgactggag ttcagacgtg tgctcttccg    60
atct    64

<210> SEQ ID NO 42
<211> LENGTH: 64
<212> TYPE: DNA
<213> ORGANISM: Artificial Sequence
<220> FEATURE:
<223> OTHER INFORMATION: primer

<400> SEQUENCE: 42
caagcagaag acggcatacg agatcgtacg gtgactggag ttcagacgtg tgctcttccg    60
atct    64

<210> SEQ ID NO 43
<211> LENGTH: 64
<212> TYPE: DNA
<213> ORGANISM: Artificial Sequence
<220> FEATURE:
<223> OTHER INFORMATION: primer

<400> SEQUENCE: 43
caagcagaag acggcatacg agatccactc gtgactggag ttcagacgtg tgctcttccg    60
atct    64

<210> SEQ ID NO 44
<211> LENGTH: 64
<212> TYPE: DNA
<213> ORGANISM: Artificial Sequence
<220> FEATURE:
<223> OTHER INFORMATION: primer

<400> SEQUENCE: 44
caagcagaag acggcatacg agatatcagt gtgactggag ttcagacgtg tgctcttccg    60
atct    64

<210> SEQ ID NO 45
<211> LENGTH: 64
<212> TYPE: DNA
<213> ORGANISM: Artificial Sequence
<220> FEATURE:
<223> OTHER INFORMATION: primer

<400> SEQUENCE: 45
caagcagaag acggcatacg agataggaat gtgactggag ttcagacgtg tgctcttccg    60
atct                                                                64

<210> SEQ ID NO 46
<211> LENGTH: 64
<212> TYPE: DNA
<213> ORGANISM: Artificial Sequence
<220> FEATURE:
<223> OTHER INFORMATION: primer

<400> SEQUENCE: 46
caagcagaag acggcatacg agatcttttg gtgactggag ttcagacgtg tgctcttccg    60
atct                                                                64

<210> SEQ ID NO 47
<211> LENGTH: 50
<212> TYPE: DNA
<213> ORGANISM: Homo sapiens

<400> SEQUENCE: 47
cttctgcacc gactcgccca cggccttgag ccccgcaaag tggatgaccg               50

<210> SEQ ID NO 48
<211> LENGTH: 51
<212> TYPE: DNA
<213> ORGANISM: Artificial Sequence
<220> FEATURE:
<223> OTHER INFORMATION: Clone figure 5

<400> SEQUENCE: 48
cttctgcacc gactcgctgc acggccttga rccccgcaaa gtggatgacc g             51

<210> SEQ ID NO 49
<211> LENGTH: 49
<212> TYPE: DNA
<213> ORGANISM: Artificial Sequence
<220> FEATURE:
<223> OTHER INFORMATION: clone figure 5

<400> SEQUENCE: 49
cttctgcacc gactcgccmc ggccttgagc cccgmaaagt ggatgaccg                49

<210> SEQ ID NO 50
<211> LENGTH: 36
<212> TYPE: DNA
<213> ORGANISM: Artificial Sequence
<220> FEATURE:
<223> OTHER INFORMATION: clone figure 5

<400> SEQUENCE: 50
cttctgcacc gactcgcccc gcaaagtgga tgaccg                              36

<210> SEQ ID NO 51
<211> LENGTH: 50
<212> TYPE: DNA
<213> ORGANISM: Artificial Sequence
<220> FEATURE:
<223> OTHER INFORMATION: clone figure 5

<400> SEQUENCE: 51
cttctgcmcc gactctcarc gkcctaaagc ccatgawagc caataacctg               50

```
<210> SEQ ID NO 52
<211> LENGTH: 48
<212> TYPE: DNA
<213> ORGANISM: Artificial Sequence
<220> FEATURE:
<223> OTHER INFORMATION: clone figure 5

<400> SEQUENCE: 52
cttctgcacc gactcgccwy ggccttgasc cccksaaaga gsatgacc          48

<210> SEQ ID NO 53
<211> LENGTH: 49
<212> TYPE: DNA
<213> ORGANISM: Artificial Sequence
<220> FEATURE:
<223> OTHER INFORMATION: clone figure 5

<400> SEQUENCE: 53
cttctgcacc gactcgccca cggccttgag ccccgcaaag tggatgacc         49
```

CELLS PRODUCING GLYCOPROTEINS HAVING ALTERED N- AND O-GLYCOSYLATION PATTERNS AND METHODS AND USE THEREOF

CROSS-REFERENCE TO RELATED APPLICATIONS

This application is a national phase entry under 35 U.S.C. § 371 of International Patent Application PCT/EP2016/066362, filed Jul. 8, 2016, designating the United States of America and published in English as International Patent Publication WO 2017/005925 A1 on Jan. 12, 2017, which claims the benefit under Article 8 of the Patent Cooperation Treaty to European Patent Application Serial No. 15176111.1 filed Jul. 9, 2015.

TECHNICAL FIELD

This application relates to the field of glyco-engineering, more specifically to eukaryotic cells wherein both an endoglucosaminidase is present, and made deficient in UDP-galactose 4-epimerase (GalE). Typically, a glycoprotein is also present in the cells. These cells can be used to deglycosylate or partly deglycosylate the (exogenous) glycoprotein, in particular without the need for adding an extra enzyme. Methods are also provided for the application of these cells in protein production.

STATEMENT ACCORDING TO 37 C.F.R. § 1.821(c) or (e)—SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

BACKGROUND

Glycoproteins are an important class of biomolecules that play crucial roles in many biological events such as cell adhesion, tumor metastasis, pathogen infection, and immune response. Most mammalian cell surface proteins and human serum proteins are glycoproteins and it is not surprising then that therapeutic glycoproteins are an important class of biotechnology products. These include, amongst many others, granulocyte macrophage-colony stimulating factor, tissue plasminogen activator, interleukin-2, erythropoietin (EPO), and antibodies. Both natural and recombinant glycoproteins are typically produced as a mixture of glycoforms that differ only in the structure of the pendent oligosaccharides. This heterogeneity in glycosylation is a major problem in structural and functional studies of glycoproteins (e.g., crystallization studies), as well as in development of glycoprotein drugs. The attached sugar chains may, for instance, have profound effects on protein folding, stability, action, pharmacokinetics, and serum half-life of the glycoprotein, and some sugar chains are very immunogenic.

Glycosylation is one of the most common post-translational modifications of proteins in eukaryotes. N-glycosylation is a highly conserved metabolic process, which in eukaryotes is essential for viability. Protein N-glycosylation originates in the endoplasmic reticulum (ER), where an N-linked oligosaccharide ($Glc_3Man_9GlcNAc_2$) assembled on dolichol (a lipid carrier intermediate) is transferred to the appropriate asparagines residue (Asn) of a nascent protein. This is a co-translational event largely common to all eukaryotic organisms. The three glucose residues and one specific α-1,2-linked mannose residue are removed by specific glucosidases and an α-1,2-mannosidase in the ER, resulting in the core oligosaccharide structure, $Man_8GlcNAc_2$. Proteins with this core sugar structure are transported to the Golgi apparatus where the sugar moiety undergoes various modifications. Glycosyltransferases and mannosidases line the inner (luminal) surface of the ER and Golgi apparatus and thereby provide a catalytic surface that allows for the sequential processing of glycoproteins as they proceed through the ER and Golgi network. The multiple compartments of the cis, medial, and trans Golgi and the trans Golgi Network (TGN), provide the different localities in which the ordered sequence of glycosylation reactions can take place. As a glycoprotein proceeds from synthesis in the ER to full maturation in the late Golgi or TGN, it is sequentially exposed to different glycosidases, mannosidases and glycosyltransferases such that a specific N-glycan structure may be synthesized. There are significant differences in the modifications of the sugar chain in the Golgi apparatus between lower and higher eukaryotes.

In higher eukaryotes, the N-linked oligosaccharides are typically high mannose, complex and mixed (hybrid) types of structures that vary significantly from those produced in yeast (Kornfeld et al., *Ann. Rev. Biochem.* 54:631-664 (1985)). In mammalian cells, the modification of the sugar chain can follow three different pathways depending on the protein moiety to which it is added. That is: (1) the core sugar chain does not change; (2) the core sugar chain is changed by adding the N-acetylglucosamine-1-phosphate moiety (GlcNAc-1-P) in UDP-N-acetyl glucosamine (UDP-GlcNAc) to the 6-position of mannose in the core sugar chain, followed by removal of the GlcNAc moiety to form an acidic sugar chain in the glycoprotein; and (3) the core sugar chain is first converted into $Man_5GlcNAc_2$ by removing three mannose residues with Golgi α-Mannosidase I; $Man_5GlcNAc_2$ is then further modified by adding GlcNAc and removing 2 more mannose residues, followed by sequentially adding GlcNAc, galactose (Gal), GalNAc, fucose and N-acetylneuraminic acid (also called sialic acid (NeuNAc)) to form various hybrid or complex sugar chains (R. Kornfeld and S. Kornfeld, 1985; Chiba et al., 1998). Different organisms provide different glycosylation enzymes (glycosyltransferases and glycosidases) and different glycosyl substrates, so that the final composition of a sugar side chain may vary markedly depending upon the higher eukaryotic host. Typically, the protein N-glycans of animal glycoproteins have bi-, tri-, or tetra-antennary structures. These branched structures are synthesized by the GlcNAc transferase-catalyzed addition of GlcNAc to regions of the oligosaccharide residue. Subsequent to their formation, the antennary structures are terminated with different sugars including Gal, GalNAc, GlcNAc, fucose (Fuc) and sialic acid residues.

In yeast and filamentous fungi (lower eukaryotes), only a part of the $Man_{8(9)}GlcNAc_2$ structures are (partially) trimmed down to $Man_5GlcNAc_2$. These oligosaccharides can then be further modified to fungal-specific glycans through the addition of mannose and/or mannosephosphate residues in a diester linkage. The resulting glycans are known as "high-mannose" type glycans or mannans. For example, yeast glycopeptides include oligosaccharide structures that consist of a high mannose core of 9-13 mannose residues, or extended branched mannan outer chains consisting of up to 200 residues (Ballou et al., *Dev. Biol.* 166:363-379 (1992); Trimble et al., *Glycobiology* 2:57-75 (1992)).

Considerable effort has been directed towards the identification and optimization of new strategies for the preparation of glycopeptides and glycoproteins for therapeutic application. Probably the most documented approach amongst the many promising methods is the engineering of cellular hosts that produce glycopeptides having a desired glycosylation pattern. For a recent review on how this can be achieved, in particular in yeast, see Wildt et al., *Nature Reviews* 2005, 119-28; and Hamilton et al., *Curr. Opin. Biotechnol.* 2007; 18(5):387-92. Other exemplary methods include chemical synthesis, enzymatic synthesis, enzymatic remodeling of formed glycopeptides and of course methods that are hybrids or combinations of one or more of these techniques.

Regarding cell host systems, in principle, mammalian, insect, yeast, fungal, plant or prokaryotic cell culture systems can be used for production of most therapeutic and other glycopeptides in commercially feasible quantities. In practice, however, a desired glycosylation pattern on a recombinantly produced protein is difficult to achieve. For example, bacteria do not N-glycosylate via the dolichol pathway, and yeast only produces oligomannose-type N-glycans, which are not generally found in large quantities in humans and are actively cleared by the liver residing macrophages. Similarly, plant cells do not produce sialylated oligosaccharides, a common constituent of human glycopeptides. In addition, plants add xylose and/or α-1, 3-linked fucose to protein N-glycans, resulting in glycoproteins that differ in structure from animals and are immunogenic in mammals (Lerouge et al., *Plant Mol. Biol.* 1998; 38(1-2): 31-48; Betenbaugh et al., *Curr. Opin. Struct. Biol.* 2004; 14(5): 601-6; Altmann, *Int. Arch. Allergy Immunol.* 2007; 142(2):99-115). As recently reviewed, none of the insect cell systems presently available for the production of recombinant mammalian glycopeptides will produce glycopeptides with the same glycans normally found when they are produced in mammals (Harrison and Jarvis, 2006, 159).

Moreover, glycosylation patterns of recombinant glycopeptides may also differ when produced under different cell culture conditions (Watson et al., *Biotechnol. Prog.* 10:39-44 (1994); and Gawlitzek et al., *Biotechnol. J.* 42:117-131 (1995)) or even between glycopeptides produced under nominally identical cell culture conditions in two different bioreactors (Kunkel et al., *Biotechnol. Prog.* 2000; 462-470 (2000)).

Thus, despite significant advances in this field, heterogeneity of glycosylation remains an issue. Heterogeneity in the glycosylation of recombinantly produced glycopeptides arises because the cellular machinery (e.g., glycosyltransferases and glycosidases) may vary from species to species, cell to cell, or even from individual to individual. The substrates recognized by the various enzymes may be sufficiently different that glycosylation may not occur at some sites or may be vastly modified from that of the native protein. Glycosylation of recombinant proteins produced in heterologous eukaryotic hosts will often differ from the native protein. Therapeutic glycoproteins are typically produced in cell culture systems as a mixture of glycoforms that possess the same peptide backbone but differ in both the nature and site of glycosylation. The heterogeneity in glycosylation poses significant difficulty for the purification, efficacy, as well as therapeutic safety of glycoproteins. Cell and/or glyco-engineering and some biochemical modifications may have yielded cells or (e.g., yeast) strains that produce recombinant glycoproteins with predominant glycoforms but, in most cases, as with natively expressed glycoproteins, the structures that have been obtained remain heterogeneous. Notably, different glycosylation forms can exert significantly different effects on the properties of a given protein, and some glycoforms can even cause allergy problems and undesired immune responses. This is, e.g., particularly true for the high-mannose-type glycoproteins normally produced in yeast. Isolation of a glycoprotein having a particular glycosylation state from such a mixture of glycosylation forms is extremely difficult. However, as small amounts of impurities can dramatically interfere with the desired activities of the glycoprotein of interest, such inhibition is also highly desirable.

A solution for this has recently been proposed in WO 2010/015722 and Meuris et al. (*Nat. Biotechnol.* 2014 32(5):485-9). The reported glycoengineering strategy—termed GlycoDelete—shortens the Golgi N-glycosylation pathway in mammalian cells. This shortening results in the expression of proteins with small, sialylated trisaccharide N-glycans and reduced complexity compared to native mammalian cell glycoproteins. GlycoDelete engineering does not interfere with the functioning of N-glycans in protein folding, and the physiology of cells modified by GlycoDelete is similar to that of wild-type cells.

However, heterogeneity in glycosylation does not only originate from N-linked sugars, but also from O-glycans attached to the glycoprotein. These carbohydrate chains are very diverse, but mucin type O-glycosylation is the most common. Contrary to endoglucosaminidases, there exists no enzyme to remove O-glycans.

Unlike N-glycans, which all share the trimannosyl core, mucin type O-glycans structurally have little in common. N-acetylgalactosamine (GalNAc) linkage to serine or threonine initiates mucin-type O-glycosylation in mammalian cells. GalNAc is the only common residue of the different mucin-type O-glycans. Further elongation of these initiating residues with a variety of monosaccharides catalyzed by a family of GalNAc transferases in the Golgi apparatus using UDP-GalNAc as donor results in a highly diverse collection of oligosaccharides.

Thus, there is a need to have a cell system or synthesis method providing homogeneous (uniform) glycosylation on a population of glycoproteins. Preferably, such a method would result in glycoproteins devoid of N- and O-glycosylation. The glycoproteins thus obtained could be used directly, or as a starting point for subsequent transglycosylation.

BRIEF SUMMARY

Provided are systems and methods for obtaining desired glycosylation profiles of a glycoprotein that are economical in both cost and time. The methods can be cheaper and faster than existing methods because there is no need for adding an enzyme to the produced glycoprotein in order to remove the undesired glycosylation products. The cells and methods address both N- and O-glycosylation. This can be achieved by expressing an endoglucosaminidase enzyme in a cell that is deficient in expression and/or activity of an endogenous GalE. Correct glycosylation of a glycoprotein (or an essentially homogeneous glycosylated population of an intermediate glycoform of the glycoprotein) is achieved by producing the glycoprotein in the same cellular system.

Thus, according to a first aspect, the following is provided: a eukaryotic cell comprising an exogenous nucleic acid sequence encoding an endoglucosaminidase enzyme and deficient in expression and/or activity of an endogenous UDP-galactose 4-epimerase (GalE).

This eukaryotic cell may further comprise a second exogenous nucleic acid sequence encoding a glycoprotein. Particularly, the eukaryotic cell does not express an endogenous endoglucosaminidase enzyme.

According to specific embodiments, the eukaryotic cell is a mammalian cell, in particular a Hek293 cell or a CHO cell.

According to specific embodiments, the endoglucosaminidase particularly is a mannosyl-glycoprotein endo-beta-N-acetylglucosaminidase (E.C. 3.2.1.96), in particular Endo T. The endoglucosaminidase may be operably linked to an ER or Golgi localization signal.

The glycoprotein may be secreted by the cell.

That such a strategy works is particularly surprising, since too strong deglycosylation of cell membrane components by the exogenous endoglucosaminidase would be expected to lead to cell membrane weakening, ultimately leading to cell lysis. This is particularly true for deglycosylation of mannoproteins of the yeast cell wall. Furthermore, the fact that the cells also lack O-glycosylation means that all glycoproteins in the cell only have single GlcNAc modifications. It is particularly surprising that the cells are still viable and show no apparent growth defects as they lack all galactose containing glycolipids, nor a penalty in yield of exogenously produced glycoproteins.

Also provided are methods for using the cells described herein. Particularly, methods are provided for producing single GlcNAc modified proteins also lacking O-glycosylation in a eukaryotic cell, comprising the steps of:
  providing a eukaryotic cell comprising a first exogenous nucleic acid sequence encoding an endoglucosaminidase enzyme, deficient in expression and/or activity of an endogenous UDP-galactose 4-epimerase (GalE) and comprising a second exogenous nucleic acid sequence encoding a glycoprotein, in conditions suitable for expressing the endoglucosaminidase enzyme and the glycoprotein; and
  recovering the glycoprotein after it has been intracellularly or extracellularly contacted with the endoglucosaminidase.

The intracellular contact with the endoglucosaminidase may particularly occur in the Golgi or endoplasmic reticulum (ER).

The methods may further comprise the step of having the glycoprotein processed by a glycosyltransferase after it has been intracellularly or extracellularly processed with the endoglucosaminidase.

This corresponds with the reduced N-glycans in HEK293sGlycoDelete and HEK293sGlycoDoubleDelete cells and the absent O-glycans in HEK293sGalE–/– and HEK293sGlycoDoubleDelete cells.

Figure 18:
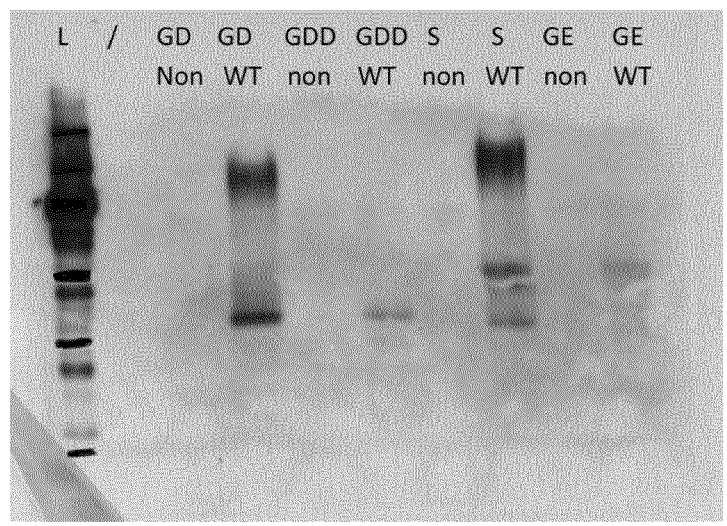

FIG. 18: SDS-PAGE and RSV-G-specific (Rabbit-anti-RSV-G) Western Blot analysis of RSV-G, expressed in HEK293s, HEK293sGalE–/–, HEK293sGlycoDelete, and HEK293sGlycoDoubleDelete cells. Non=non-transfected cells; WT=cells transfected with vector encoding wild type RSV-G protein.

DETAILED DESCRIPTION

Definitions

This disclosure will be described with respect to particular embodiments and with reference to certain drawings but the disclosure is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

The following terms or definitions are provided solely to aid in the understanding of the disclosure. Unless specifically defined herein, all terms used herein have the same meaning as they would to one skilled in the art of this disclosure. Practitioners are particularly directed to Sambrook et al., *Molecular Cloning: A Laboratory Manual,* 4th ed., Cold Spring Harbor Press, Plainsview, New York (2012); and Ausubel et al., *Current Protocols in Molecular Biology* (Supplement 114), John Wiley & Sons, New York (2016), for definitions and terms of the art. The definitions provided herein should not be construed to have a scope less than understood by a person of ordinary skill in the art.

"Glyco-engineered yeast cells" as used in the application are yeast cells that express at least one exogenous nucleic acid sequence encoding an enzyme needed for complex glycosylation that is not expressed in the wild-type yeast, and/or that do not express at least one enzyme involved in the production of high-mannose type structures that is normally expressed in the wild type yeast.

An "endoglucosaminidase" as used herein refers to enzymes that hydrolyze the bond between the anomeric carbon of a non-terminal beta-linked N-acetylglucosamine residue in an oligosaccharide of a glycoprotein or a glycolipid, and its aglycon, thereby releasing mono- or oligosaccharides from glycoproteins or glycolipids or sugar polymers. Endoglucosaminidases are a subset of the glycosidases, and may or may not have other enzymatic activities (such as, e.g., glycosyltransferase activity). A particular class of endoglucosaminidases is formed by the endo-β-N-acetylglucosaminidases or mannosyl-glycoprotein endo-β-N-acetylglucosaminidases, indicated as EC 3.2.1.96 in the International Union of Biochemistry and Molecular Biology (IUBMB) nomenclature. This particular class of enzymes are capable of catalyzing the endohydrolysis of the N,N'-diacetylchitobiosyl unit in high-mannose glycopeptides and glycoproteins containing the -[Man(GlcNAc)$_2$]Asn- structure. One N-acetyl-D-glucosamine (GlcNAc) residue remains attached to the protein; the rest of the oligosaccharide is released intact. The result thus is a single GlcNAc-modified glycoprotein. Of note, the remaining GlcNAc residue may be either unmodified or still be modified with other sugar residues in other positions than that of the hydrolyzed bond, for instance, the GlcNAc residue may carry a fucose on position 3 or 6. Nevertheless, glycoproteins with a modified GlcNAc residue will still be referred to as single GlcNAc-modified proteins, as there is no second sugar residue on position 4 of the GlcNAc residue (i.e., there is no typical sugar chain). A particular advantage of endoglucosaminidases as compared to exoglycosidases is that they allow discrimination between N-linked and O-linked glycans and between classes of glycans. A non-limiting list of endoglucosaminidases is provided in the application.

Particularly with regard to the glyco-engineered yeast cells, an "enzyme needed for complex glycosylation" as used herein refers to any enzyme not naturally occurring in the host yeast cell that may be involved in the synthesis of complex glycans as found in higher eukaryotes, in particular as found in mammals, more in particular as found in humans. Most particularly, such enzymes are enzymes that remove mannose residues from the sugar chain (i.e., mannosidases) or glycosyltransferases, in particular glycosyltransferases other than mannosyltransferases (i.e., glycosyltransferases that transfer monosaccharides that are not found in high-mannose glycans) and/or phosphomannosyltransferases.

A "glycosyltransferase" as used in the application is any of a group of enzymes that catalyze the transfer of glycosyl groups in biochemical reactions, in particular glycosyl transfer to asparagine-linked sugar residues to give N-linked glycoproteins. Glycosyltransferases fall under EC 2.4 in the IUBMB nomenclature, a particular class of glycosyltransferases are hexosyltransferases (EC 2.4.1). Among the wide variety of these post-translational enzymes that process peptides into glycoproteins are enzymes such as, but not limited to, N-acetylglucosaminyl transferases, N-acetylgalactosaminyltransferases, sialyltransferases, fucosyltransferases, galactosyltransferases, and mannosyltransferases.

Note that exogenous mannosyltransferases are excluded for specific embodiments of glyco-engineered yeast cells described herein. "Mannosyltransferases" as used in the application refers to enzymes that catalyze the transfer of a mannosyl group to an acceptor molecule, typically another carbohydrate, in the Golgi apparatus. Mannosyltransferases are typically endogenous enzymes in yeast and involved in the synthesis of high-mannose type glycans.

Of note, an enzyme may possess both endoglucosaminidase and glycosyltransferase activity. Although it may be possible to use one enzyme to exert these two activities, typically the enzymes used will fulfill only one function. Thus, it is envisaged to use enzymes that have been modified or mutated to make sure they perform only one function, or that have been modified or mutated to ensure they carry out a specific function more efficiently. Such modified enzymes are known in the art.

"Glycoproteins" as used in the application refers to proteins that, in their normal physiological context and/or their functional form, contain oligosaccharide chains (glycans) covalently attached to their polypeptide side-chains. The carbohydrate may be attached to the protein in a co-translational or post-translational modification. In particular, glycoproteins as used herein are proteins that show N-glycosylation in their physiologically active form. Thus, glycoproteins typically contain a sugar chain at least on one asparagine residue. A non-limiting list of glycoproteins is provided in the specification. The term "glycoproteins" is not intended to refer to the length of the amino acid chain, "glycopeptides" are included within the definition of "glycoproteins."

The terms "(glyco)protein" and "enzyme" (e.g., endoglucosaminidase, glycosyltransferase, mannosidase, mannosyltransferase) as used in the application are also intended to cover functionally active fragments and variants of the naturally occurring proteins.

Indeed, for many (e.g., therapeutic) proteins, part of the protein may be sufficient to achieve an (e.g., therapeutic, enzymatic) effect. The same applies for variants (i.e., proteins in which one or more amino acids have been substituted with other amino acids, but that retain functionality or even show improved functionality), in particular for variants of the enzymes optimized for enzymatic activity.

In the context of the application, a glycoprotein refers to the protein itself; a glycoprotein may be either in its glycosylated or non-glycosylated form. A "glycosylated" protein is a (glyco)protein that carries at least one oligosaccharide chain.

A "sugar chain," "oligosaccharide chain" or "carbohydrate chain," as used herein, is a chain of two or more monosaccharides. As a consequence, a protein carrying only a single monosaccharide (e.g., a single GlcNAc residue) will usually, unless specified otherwise, not be referred to as a glycosylated protein, but as a protein that carries a monosaccharide, or a monosaccharide (e.g., GlcNAc)-modified protein. Typical monosaccharides that may be included in an oligosaccharide chain of a glycoprotein include, but are not limited to, glucose (Glu), galactose (Gal), mannose (Man), fucose (Fuc), N-acetylneuraminic acid (NeuAc) or another sialic acid, N-acetylglucosamine (GlcNAc), N-acetylgalactosamine (GalNAc), xylose (Xyl) and derivatives thereof (e.g., phosphoderivatives). Sugar chains may be branched or not, and may comprise one or more types of oligosaccharide. In general, sugar chains in N-linked glycosylation may be divided in three types: high-mannose, complex and hybrid type glycosylation. These terms are well known to the skilled person and defined in the literature. Briefly, high-mannose type glycosylation typically refers to oligosaccharide chains comprising two N-acetylglucosamines with (possibly many) mannose and/or mannosylphosphate residues (but typically no other monosaccharides).

Complex glycosylation typically refers to structures with typically one, two or more (e.g., up to six) outer branches with a sialyllactosamine sequence, most often linked to an inner core structure $Man_3GlcNAc_2$. For instance, a complex N-glycan may have at least one branch, or at least two, of alternating GlcNAc and galactose (Gal) residues that may terminate in a variety of oligosaccharides but typically will not terminate with a mannose residue.

Hybrid type glycosylation covers the intermediate forms, i.e., those glycosylated proteins carrying both terminal mannose and terminal non-mannose residues in addition to the two N-acetylglucosamine residues. In contrast to complex glycosylation, at least one branch of hybrid type glycosylation structures ends in a mannose residue.

Although this classification is most often used to describe naturally occurring glycans on proteins, it is evident that synthetic and/or non-naturally occurring sugars can also be classified this way, even if their structures diverge from the classical example. For instance, a sugar chain consisting of a single branch of a galactose and a sialic acid residue linked to a single GlcNAc would be a complex sugar, even though it lacks the inner core $Man_3GlcNAc_2$.

An "ER localization signal" or a "Golgi localization signal" is a molecule, typically a peptide that directs localization of the polypeptide or protein to which it is conjugated to the ER or Golgi apparatus, respectively. Localization thus also implies retention in the ER or Golgi apparatus, respectively. Typically, these localization (or retention) sequences are peptide sequences derived from (pre)proteins that are situated in the ER or Golgi when functionally active as a mature protein.

"UDP-galactose 4-epimerase," "GalE" or "UDP-glucose 4-epimerase" as used herein refers to an enzyme of enzyme class EC 5.1.3.2. Human (and selected other) GalE isoforms bind UDP-GlcNAc, reversibly catalyzing its conversion to UDP-GalNAc, and also convert UDP-Glu to UDP-Gal. A family of glycosyltransferases known as UDP-N-acetylgalactosamine:polypeptide N-acetylgalactosamine transferases (ppGaNTases) transfers GalNAc from UDP-GalNAc to glycoprotein serine and threonine residues. ppGaNTase-mediated glycosylation represents the first committed step in mucin biosynthesis.

To make a cell deficient in expression and/or activity of an endogenous UDP-galactose 4-epimerase, several strategies can be used, and the nature of the strategy is not vital to the disclosure, as long as it results in diminishing GalE activity to the extent that O-glycosylation is not present in the cell. Cells can be made deficient for GalE at the genetic level, e.g., by deleting, mutating, replacing or otherwise disrupting the (endogenous) gene encoding GalE (for instance, using Crispr/Cas technologies as described in the Examples).

Alternatively, one can interfere with transcription from the GalE gene, or remove or inhibit the transcribed (nucleic acid, mRNA) or translated (amino acid, protein) gene products. This may, for instance, be achieved through siRNA inhibition of the GalE mRNA. Also morpholinos, miRNAs, shRNA, LNA, small molecule inhibition or similar technologies may be used, as the skilled person will be aware of. The GalE protein can, for instance, be inhibited using inhibitory antibodies, antibody fragments, scFv, Fc or nanobodies, small molecules or peptides.

As will be clear to those of skill in the art, deficiency of GalE expression and/or activity may both be constitutive (e.g., genetic deletion) or inducible (e.g., small molecule inhibition).

"Deficient" as used herein typically means that the activity of GalE is less than 75% of a relevant control (e.g., the same cell with an intact GalE gene), particularly less than 90%. More important than the percentage of activity, however, is the functional deficiency; i.e., a cell is functionally deficient in GalE if the GalE inhibition results in the fact that no GalNAc can be added to a serine or threonine residue, or to a nascent glycan chain (particularly to a GlcNAc residue present on an amino acid). Thus, regardless of measured enzyme activity, a cell that, through inhibition of GalE nucleic acid or protein, can no longer add GalNAc residues to amino acids of a glycoprotein (bare serine and threonine residues, or GlcNAc modified amino acids), is said to be deficient in GalE expression and/or activity.

The wording "devoid of mucin type O-glycans" means that the glycoprotein of the composition is essentially free of mucin type O-glycans and thus, that all of the O-glycans that were originally present on the glycoproteins are removed. In the scope of this disclosure, glycoproteins that still comprise 5, 10, 15, or 20% of their original mucin type O-glycans are considered to be essentially free of mucin type O-glycans.

This disclosure aims to provide cells producing glycoproteins with an altered glycosylation pattern, in particular a more homogeneous glycosylation pattern that makes them more amenable for further use, e.g., therapeutic use, or use in crystallization studies. We previously showed this could be done for N-glycosylation in Glycodelete cell lines (WO 2010/015722 and Meuris et al. (*Nat. Biotechnol.* 2014; 32(5):485-9)).

Just like N-glycosylation, O-glycosylation is a major source of heterogeneity in recombinant protein production. Removing this could be convenient in crystallography, where O-glycosylation often forms a major issue, since crystallizing heterogeneous proteins is very challenging. Also there might be potential in the subunit vaccine field, where O-glycans could cover stable epitopes, just like N-glycans do. For example, gp120 of HIV, G-protein of RSV and the mucin domain on GP protein of Ebola are all abundantly O-glycosylated.

Figure 13:
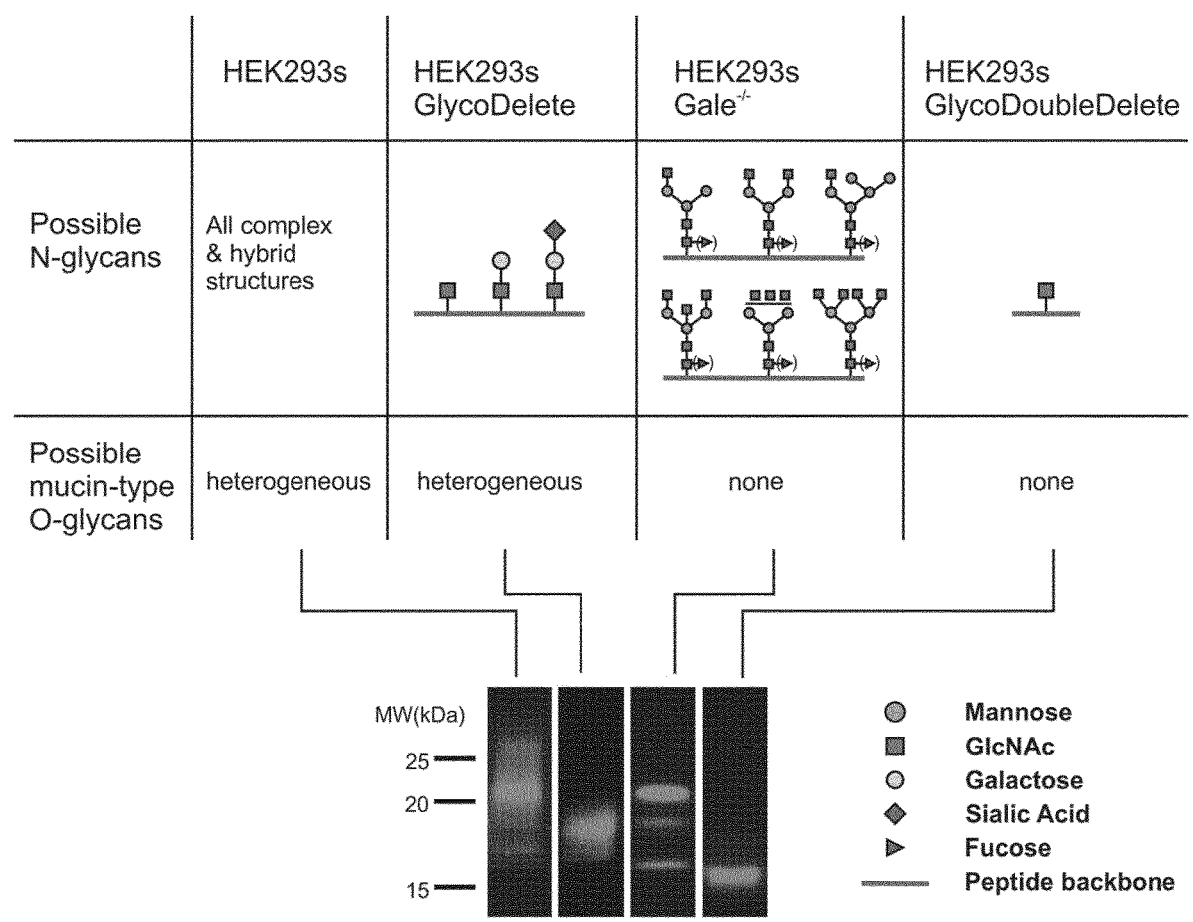
FIG. 13: An overview of the different cell lines we derived from HEK293s, their possible N- and O-linked glycans and the result of this engineering on heterogeneity of hGM-CSF expressed in the different cell lines.

Interestingly, combining the approach for removal of O-glycosylation even further reduces the variability of N-glycosylation, so that only a single GlcNAc residue remains on all sugars. See Examples section and FIG. 13.

Thus, according to a first aspect, eukaryotic cell are provided comprising an exogenous nucleic acid sequence encoding an endoglucosaminidase enzyme and deficient in expression and/or activity of an endogenous UDP-galactose 4-epimerase (GalE). This eukaryotic cell typically also comprises a second exogenous nucleic acid sequence encoding a glycoprotein.

The nature of the glycoprotein is not critical to the disclosure, but glycoproteins will typically be proteins relevant for medicine and/or industry for which correct N-glycosylation is important for their function. Non-limiting examples include many hormones, growth factors, cytokines and their corresponding receptors, such as follicle-stimulating hormone (FSH), luteinizing hormone (LH), thyroid-stimulating hormone (TSH), epidermal growth factor (EGF), human epidermal growth factor receptor-2 (HER-2), fibroblast growth factor-alpha (FGF-α), fibroblast growth factor-beta (FGF-β), transforming growth factor-alpha (TGF-α), transforming growth factor-beta (TGF-β), platelet-derived growth factor (PDGF), insulin-like growth factor-1 (IGF-1), insulin-like growth factor-2 (IGF-2), nerve growth factor (NGF), nerve growth factor-beta (NGF-13); receptors of the aforementioned, growth hormones (e.g., human growth hormone, bovine growth hormone); insulin (e.g., insulin A chain and insulin B chain), proinsulin; erythropoietin (EPO); colony stimulating factors (e.g., granulocyte colony-stimulating factor (G-CSF), granulocyte macrophage colony-stimulating factor (GM-CSF), macrophage colony-stimulating factor (M-CSF)); interleukins (e.g., IL-1 through IL-12); vascular endothelial growth factor (VEGF) and its receptor (VEGF-R); interferons (e.g., IFN-α, β, or γ); tumor necrosis factor (e.g., TNF-α and TNF-β) and their receptors, TNFR-1 and TNFR-2; thrombopoietin (TPO); thrombin; brain natriuretic peptide (BNP); clotting factors (e.g., Factor VIII, Factor IX, von Willebrands factor, and the like); anti-clotting factors; tissue plasminogen activator (TPA), e.g., urokinase or human urine or tissue type TPA; calcitonin; CD proteins (e.g., CD3, CD4, CD8, CD28, CD19, etc.); CTLA proteins (e.g., CTLA4); T-cell and B-cell receptor proteins; bone morphogenic proteins (BMPs, e.g., BMP-1, BMP-2, BMP-3, etc.); neurotrophic factors, e.g., bone-derived neurotrophic factor (BDNF); neurotrophins, e.g., 3-6; renin; rheumatoid factor; RANTES; albumin; relaxin; macrophage inhibitory protein (e.g., MIP-1, MIP-2); viral proteins or antigens; surface membrane proteins; ion channel proteins; enzymes; alkaline phosphatase; lectins; regulatory proteins; antibodies; immunomodulatory proteins, (e.g., HLA, MHC, the B7 family); homing receptors; transport proteins; superoxide dismutase (SOD); G-protein coupled receptor proteins (GPCRs); neuromodulatory proteins; Alzheimer's Disease associated proteins and peptides, (e.g., A-beta), and others as known in the art, including fusion or chimeric proteins of the above. Fragments or portions, or mutants, variants, or analogues of any of the aforementioned proteins and polypeptides are also included among the suitable proteins, polypeptides and peptides that can be produced by the cells and methods presented herein.

The glycoprotein may be secreted by the cell.

The nature of the endoglucosaminidase will depend on the desired glycopopulation of the glycoproteins. For instance, endoglucosaminidases may be selected for their substrate specificity. Some endoglucosaminidases, e.g., Endo H and Endo T, hydrolyze high-mannose type sugar chains and hybrid type sugars, but leave complex carbohydrate structures intact. Such enzymes are ideal, e.g., for obtaining single GlcNAc-modified glycoproteins from cells incapable of complex glycosylation, or for removing contaminating high-mannose and/or hybrid type sugars in cells producing complex glycosylated proteins as well as other glycoforms (such as most glyco-engineered yeast strains). According to particular embodiments, the endoglucosaminidase hydrolyses high mannose-type sugar chains and hybrid-type glycans, but not complex-type glycans.

Endoglucosaminidases may also have substrate specificity with regard to the glycoprotein (instead of only the sugar chain), some endoglucosaminidases are, e.g., more successful in hydrolyzing sugar chains from (particularly compactly folded) proteins than other endoglucosaminidases (e.g., Endo T), others may (also) be particularly successful in hydrolyzing sugar chains from glycopeptides or not-compactly folded proteins (e.g., Endo H, Endo T). Importantly, as this typically has to do with access to or availability of the substrate rather than with the specificity of the endoglucosaminidase, this does not exclude the use of certain enzymes for specific proteins, but some endoglucosaminidases may require more time to complete the hydrolysis of all N-linked sugar structures.

The choice of endoglucosaminidases may also depend on the resulting product(s). For instance, when different glycopopulations are secreted (e.g., complex-type glycosylated proteins that are not hydrolyzed and other types that are hydrolyzed), it may be important that the resulting proteins can be easily separated. As another example, when further transglycosylation is envisaged, endoglucosaminidases leaving single GlcNAc-modified proteins (e.g., Endo H, Endo T) are particularly envisaged, as the single GlcNAc residue on the protein offers a suitable substrate for the glycosyltransferase to attach the sugar modification. This is a significant advantage of the eukaryotic cells described herein as compared to bacterial expression systems, as the bacteria cannot produce single GlcNAc-modified glycoproteins, which makes it much more difficult to use proteins produced in bacteria as starting point for transglycosylation. Alternatively, single GlcNAc-modified proteins can be used in crystallization studies, although this is also true for non-glycosylated proteins. Thus, endoglucosaminidases removing the whole sugar chain without leaving a monosaccharide on the protein (such as peptide-N-glycosidase F) may be envisaged when using the produced glycoproteins for crystallization. Another consideration may be the presence or absence of other enzymatic activities, such as glycosyltransferase activity. Endo A, Endo BH and Endo M, for instance, are known to possess such glycosyltransferase activity, and it may for some embodiments be desirable to work with mutants that do no longer possess this activity.

A particular class of endoglucosaminidases is formed by the mannosyl-glycoprotein endo-β-N-acetylglucosaminidases, indicated as EC 3.2.1.96 in the IUBMB nomenclature. These enzymes can remove sugar chains while leaving one GlcNAc residue on the protein. Examples of these include, but are not limited to Endo A, Endo BH, Endo CE, Endo D, Endo F1, Endo F2, Endo F3, Endo H, Endo M, Endo T (see also WO2006/050584), AcmA, and ENGase. Other examples are known to the skilled person and can, for instance, be found on www.cazy.org, in particular under the Glycoside Hydrolase Family 85 and 18. Particularly envisaged is the use of the Endo T enzyme from *Hypocrea jecorina* (formerly known as *Trichoderma reesei*) that is described in WO2006/050584 (see, e.g., SEQ ID NOS:9-12 therein).

According to particular embodiments, the eukaryotic cells do not express an endogenous endoglucosaminidase enzyme, in particular no mannosyl-glycoprotein endo-β-N-acetylglucosaminidase. According to alternative particular embodiments, the eukaryotic cells do not express an enzyme with functional endoglucosaminidase activity other than the endoglucosaminidase enzyme encoded by the first exogenous nucleic acid sequence. That is, they may, for instance, express another endoglucosaminidase, but an endoglucosaminidase that is modified to no longer have its hydrolase activity (but, e.g., only its glycosyltransferase activity, so that it can function in the synthesis of complex glycosylation structures).

Further, the cells are made deficient in expression and/or activity of an endogenous UDP-galactose 4-epimerase (GalE). As this is the first step of the O-glycosylation pathway, this ensures that no O-glycosylation is present in the cells. Furthermore, this also can even further reduce the remaining heterogeneity that is sometimes observed when N-glycosylation is already modified by introduction of an exogenous endoglucosaminidase.

The eukaryotic cells as described herein produce uniformly, single GlcNAc-modified glycoproteins that are ready to use (e.g., for crystallization studies), or that may be used as a starting point for further glycomodification reactions, e.g., by glycosyltransferases.

Glycosyltransferases have been used to modify the oligosaccharide structures on glycopeptides, and have been shown to be very effective for producing specific products with good stereochemical and regiochemical control. Glycosyltransferases may be used to prepare oligosaccharides and to modify terminal N- and O-linked carbohydrate structures on glycopeptides produced in eukaryotic cells. For example, the terminal oligosaccharides may be completely sialylated and/or fucosylated to create sugar structures that improve glycoprotein (or glycopeptides) pharmacodynamics and a variety of other biological properties, such as, e.g., immunogenicity. Such glycosyltransferases may be used in natural or synthetic pathways, for instance, fucosyltransferases have been used in synthetic pathways to transfer a fucose unit from guanosine-5'-diphosphofucose to a specific hydroxyl of a saccharide acceptor (Ichikawa et al., *J. Am. Chem. Soc.* 114:9283-9298 (1992)).

Under appropriate conditions, both exoglycosidases and endoglycosidases have been shown to possess glycosyl transferase activity. Methods based on the use of endoglycosidases have the advantage that an oligosaccharide, rather than a monosaccharide, is transferred. The above enzymes can be utilized in the generation of carbohydrates (that are, e.g., to be conjugated to glycoproteins) as well as glycosylated glycoproteins themselves. For examples of how glycosyltransferases may be used in the further processing of, e.g., single GlcNAc modified-glycoproteins, see, e.g., Takegawa, *JBC* 3094, Koeller et al., 835, *Nat. Biotech.* 2000; WO03/046150, and WO07/133855.

However, instead of delivering the intermediary glycoprotein product that is to be used in further transglycosylation steps with a glycosyltransferase that needs to be added, it is also envisaged that the cells described herein may themselves produce the glycosyltransferase(s). Indeed, it is envisaged that the glycosyltransferase(s) of the cells perform a glycosylation reaction on the glycoproteins, either within the cells or in the extracellular environment, thereby yielding a uniform population of glycoproteins with the desired (typically complex) glycosylation profile.

Thus, according to particular embodiments, the cells possess a third exogenous nucleic acid sequence encoding a glycosyltransferase enzyme. According to specific alternative embodiments, the endoglucosaminidase and glycosyltransferase activity are performed by the same enzyme. This may be because there is only one enzyme and both activities are thus encoded by the same sequence (although it is also possible that the enzyme sequence is identical, but the localization or secretion sequence differs). Alternatively, it is envisaged that two versions of the same enzyme are expressed in the cell (e.g., Endo T, Endo M), one that has endoglucosaminidase activity but (preferably) no glycosyltransferase activity, and one that has only glycosyltransferase activity. If an enzyme is used that still has both activities, it is important to control (spatiotemporal) access to its substrate, in order to avoid interference of the two enzymatic activities. For instance, when the enzyme and glycoprotein are secreted, the endoglucosaminidase activity may be activated first (e.g., by adapting pH), after which substrates for transglycosylation can be added to the medium. Even so, it should be ensured that the endoglucosaminidase is not able to hydrolyze the glycoprotein after it has been modified with a sugar chain by the glycosyltransferase activity.

According to particular embodiments however, the glycosyltransferase is not encoded by the same sequence as the endoglucosaminidase. According to further particular embodiments, one or more glycosyltransferases different from the endoglucosaminidases are used. Examples include, but are not limited to, sialyltransferases such as α-sialyltransferases, galactosyltransferases such as β-1, 4-galactosyltransferase, and fucosyltransferases.

According to alternative, but not necessarily exclusive, particular embodiments, the cells are glyco-engineered yeast cells, i.e., yeast cells that also possess at least a third exogenous nucleic acid sequence encoding at least one enzyme needed for complex glycosylation, and/or are deficient in the activity of at least one endogenous glycosyltransferase. According to particular embodiments, the enzyme needed for complex glycosylation is a mannosidase or a glycosyltransferase other than a mannosyltransferase. According to further particular embodiments, the at least one enzyme needed for complex glycosylation is selected from the group consisting of N-acetylglucosaminyl transferase I, N-acetylglucosaminyl transferase II, mannosidase II, galactosyltransferase, and sialyltransferase.

According to particular embodiments, the glyco-engineered yeast cell may be characterized in that at least one enzyme involved in the production of high mannose structures (high mannose-type glycans) is not expressed (or is not functionally active in the cell). According to further particular embodiments, at least one mannosyltransferase is not expressed in the glyco-engineered yeast cell. Typically, the mannosyltransferase that is not expressed in the glyco-engineered yeast cell is expressed in the wild-type counterpart of the yeast cell. According to yet further particular embodiments, the mannosyltransferase is a α-1, 2-mannosyltransferase, α-1, 3-mannosyltransferase, α-1, 6-mannosyltransferase, or β-1, 4-mannosyltransferase. These proteins often have specific names in yeast (e.g., Alg, Och, Mnn), but their activities are well known in the art. Alternatively or additionally, at least one mannosylphosphate transferase is not functionally active in the glyco-engineered yeast cell.

In the eukaryotic cells described herein, the glycosyltransferase may, just like the endoglucosaminidase, be secreted or be retained in the cell, in particular targeted to the ER or Golgi. In the latter case, it will typically be targeted to a later stage of the ER→Golgi assembly pathway for glycosylated proteins, to ensure that the proteins are (partly) deglycosylated by the endoglucosaminidase first, after which they are subject to transglycosylation by the glycosyltransferase. This way, depending on the combinations of endoglucosaminidase(s) and glycosyltransferase(s), naturally occurring as well as synthetic glycans can be added to the glycoproteins.

Eukaryotic cells can be of any eukaryotic organism, but in particular embodiments yeast, plant, mammalian and insect cells are envisaged. The nature of the cells used will typically depend on the desired glycosylation properties and/or the ease and cost of producing the glycoprotein. Mammalian cells may, for instance, be used for achieving complex glycosylation and avoiding problems with immunogenicity, but it may not be cost-effective to produce proteins in mammalian cell systems. Plant and insect cells, as well as yeast typically achieve high production levels and are more cost-effective, but additional modifications may be needed to mimic the complex glycosylation patterns of mammalian proteins, or to reduce problems with immunogenicity. Eukaryotic cell lines for protein production are well known in the art, including cell lines with modified glycosylation pathways. Nonlimiting examples of animal or mammalian host cells suitable for harboring, expressing, and producing proteins for subsequent isolation and/or purification include Chinese hamster ovary cells (CHO), such as CHO-K1 (ATCC CCL-61), DG44 (Chasin et al., 1986, *Som. CellMolec. Genet.* 12:555-556; and Kolkekar et al., 1997, *Biochemistry* 36:10901-10909), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), RR-CHOK1 designated ECACC 92052129 (CAMR, Salisbury, Wiltshire, UK), suspension-adapted CHO-XL99 cells (Acyte Biotech, Brisbane, Australia), Freestyle CHO-S cells (Life Technologies), dihydrofolate reductase negative CHO cells (CHO/-DHFR, Urlaub and Chasin, 1980, *Proc. Natl. Acad. Sci. USA*, 77:4216), and dp12.CHO cells (U.S. Pat. No. 5,721,121); monkey kidney CV1 cells transformed by SV40 (COS cells, COS-7, ATCC CRL-1651); human embryonic kidney cells (e.g., 293 cells, or 293T cells, or 293 cells subcloned for growth in suspension culture, Graham et al., 1977, *J. Gen. Virol.* 36:59); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse sertoli cells (TM4, Mather, 1980, *Biol. Reprod.* 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982, *Annals N.Y. Acad. Sci.* 383:44-68); MCR 5 cells; FS4 cells. Exemplary non-mammalian cell lines include, but are not limited to, Sf9 cells, baculovirus-insect cell systems (e.g., review Jarvis, *Virology*, Volume 310, Issue 1, 25 May 2003, Pages 1-7), plant cells such as tobacco cells, tomato cells, maize cells, algae cells, or yeasts such as *Saccharomyces* species, *Hansenula* species, *Yarrowia* species or *Pichia* species. According to particular embodiments, the eukaryotic cells are yeast cells from a *Saccharomyces* species (e.g., *Saccharomyces cerevisiae*), a *Hansenula* species (e.g., *Hansenula polymorpha*), a *Yarrowia* species (e.g., *Yarrowia lipolytica*), a *Kluyveromyces* species (e.g., *Kluyveromyces lactis*) or a *Pichia* species (e.g., *Pichia pastoris*). According to a specific embodiment, the eukaryotic cells are *Pichia* cells, and in a most particular embodiment *Pichia pastoris* cells. *Pichia pastoris* has been shown to have a secretory pathway with distinct Golgi stacks similar to those found in mammalian cells.

According to an alternative particular embodiment, the cells are mammalian cells selected from Hek293 cells or CHO cells.

The eukaryotic cells as described herein may produce uniformly glycosylated glycoproteins that are single GlcNAc-modified.

According to particular embodiments, the endoglucosaminidase enzyme encoded by the first exogenous nucleic acid sequence is a mannosyl-glycoprotein endobeta-N-acetylglucosaminidase, i.e., it has the activity of E.C. 3.2.1.96 in the IUBMB nomenclature, implying that it can remove sugar chains while leaving one GlcNAc residue on the protein. According to alternative embodiments, the endoglucosaminidase encoded by the first exogenous nucleic acid sequence has different affinities towards different types of glycosylation structures. Typical examples of the latter are endoglucosaminidases that are able to hydrolyze hybrid type sugars and/or high-mannose sugars, but are not capable of cleaving complex type glycans. According to further particular embodiments, the endoglucosaminidase is a mannosyl-glycoprotein endo-beta-N-acetylglucosaminidase that has different affinities towards different types of glycosylation structures. According to yet further particular embodiments, the endo-beta-N-acetylglucosaminidase is able to cleave hybrid type sugars and/or high-mannose sugars, but not complex type glycans. According to even more particular embodiments, the endoglucosaminidase is EndoH or EndoT. According to most particular embodiments, the endoglucosaminidase is Endo T.

The glycoproteins produced by the cells described herein typically should be easily recovered. This will particularly be achieved by secretion of the glycoprotein. This can be after contact with the endoglucosaminidase (e.g., when the endoglucosaminidase remains in the cell), or before the contact with the endoglucosaminidase (e.g., when both are secreted). Secretion signals will in general be similar for both glycoproteins and endoglucosaminidases (or optionally also glycosyltransferases), if the latter are secreted. The nature of the secretion signal will indeed typically not depend on the protein to be secreted, but on the type of eukaryotic cells used. As long as the secretion signal is functional in the cell type in which it is used (i.e., it results in secretion to the extracellular environment of the protein or peptide to which it is fused), this feature is not critical to the disclosure. Thus, secretion signals from other organisms may be used, as long as these signals lead to secretion in the eukaryotic cells used. Secretion signals are well known in the art and may be derived from—typically the N-terminus of—proteins that are secreted, or may be made synthetically (e.g., Tan et al., *Protein Engineering* 2002, vol. 15, no. 4, pp. 337-345). Alternatively, they can be derived from genomic sequences using computational methods (Klee et al., *BMC Bioinformatics* 2005, 6:256). Also, bacterial secretion signals can be used. Further examples of signal peptides that can be used are described in WO2002/048187 (eukaryotic cells), Schaaf et al. (*BMC Biotechnol.* 2005; 5:30) (moss cells), EP549062. Specific secretion signals used in yeast include, e.g., α-factor secretory peptide, the PH05 secretory peptide, and the BAR1 secretion signal.

Although secretion is particularly envisaged for easy recovery of glycoproteins, alternative options exist. The produced glycoproteins may, for instance, be deposited in inclusion bodies in the cell, or in membrane-bound organelles or in structures with similar functions. When cells are part of an organism that is used for production (e.g., a plant instead of a plant cell culture), the glycoprotein may be produced in or transported to specific organs or tissues of the organism from which it can be recovered (e.g., glands or trichomes). It should be noted that, particularly in cases where the protein is not secreted, it is possible that the protein is deposited in an inactive form. Thus, additional refolding or re-activating steps may be needed in order to obtain a physiologically relevant form of the glycoprotein.

Although, in addition to the glycoprotein, the endoglucosaminidase may also be secreted by the cell (using identical or similar secretion signals—i.e., the remarks on secretion signals for glycoproteins also apply for endoglucosaminidases), it can be a particular advantage that the endoglucosaminidase remains in the cell. This takes away the need for separation of the endoglucosaminidase and the glycoprotein, which arises when both proteins are secreted. Most particularly, the endoglucosaminidase not only remains in the cell, but is also fully active. Its activity should be regulated spatiotemporally, in order to ensure that the desired hydrolysis takes place. To this end, the endoglucosaminidase may be operably linked to an ER or Golgi localization signal. Such signal directs the endoglucosaminidase to the ER or Golgi, respectively, where it is retained. As the ER and Golgi apparatus are the intracellular locations where glycosylation of proteins takes place, targeting to these organelles ensures that the endoglucosaminidase is in the correct intracellular position to modify the glycosylation of the glycoprotein.

This is particularly also true for the glyco-engineered yeast cells described herein, as the at least one enzyme needed for complex glycosylation is also targeted to function in the ER→Golgi secretory pathway, the endoglucosaminidase can be targeted in such a way that these enzymes act cooperatively on the glycoprotein.

Indeed, in yeast—as in humans—the luminal surface of the ER and Golgi apparatus provides catalytic surfaces that allow the sequential processing of glycoproteins as they proceed from the ER through the Golgi network into the medium. As a glycoprotein proceeds from the ER through the secretory pathway, it is sequentially exposed to different mannosidases and glycosyltransferases. Several processing steps rely on previous reactions because some N-glycosylation enzymes depend on a particular substrate that is created by the previous enzyme. N-glycosylation enzymes, in particular exogenous enzymes such as the endoglucosaminidase and the at least one enzyme needed for complex glycosylation, must therefore be arranged in a predetermined sequence to allow for the synthesis of specific N-glycan structures.

Establishing the sequential processing environments of the secretory pathway requires the proper localization of N-glycosylation enzymes. The mechanisms by which secreted proteins can be transported through the secretory pathway (from the ER to the cis-, medial- and trans-Golgi compartments and into the medium), while each compartment maintains a specific set of resident (for example, N-glycosylation) enzymes, has been the subject of extensive study. Two well-established mechanisms that localize proteins to the various compartments of the secretory pathway are retrieval and retention (van Vliet et al., *PBMB* 1 2003; Teasdale et al., 27 1996).

Retrieval is a process by which proteins are localized to certain organelles through interaction with other proteins. Several ER-residing proteins contain a carboxy-terminal tetrapeptide with the consensus sequence KDEL (SEQ ID NO: 1) (or HDEL (SEQ ID NO:2) in yeast), which has been shown to be required for efficient localization to the ER.

Several ER- and Golgi-residing enzymes are type II membrane proteins. These proteins have a common domain structure comprising a short cytoplasmic tail at the amino terminus, a hydrophobic transmembrane domain, a luminal stem and a C-terminal catalytic domain. Deletion studies as well as fusions to non-Golgi-residing proteins have identified the N-terminus, and in particular the transmembrane region, as containing the targeting information of many type II membrane proteins. Although it is clear that N-terminal domains are involved in targeting, the extent to which their targeting ability is transferable between different species is not yet totally clear. Nevertheless, considerable advances have been made, such as the design of genetic libraries of known type II membrane protein domains that encode peptides that are associated with proteins that naturally localize to the ER and Golgi of S. cerevisiae or P. pastoris (Choi et al., 5022 2003; Hamilton et al.; Science 1244) confirming the suitability of, e.g., the leader sequence from S. cerevisiae Sec12 (ER localization), MNN2 (Golgi localization), and MNN9 (Golgi localization). Sequences listed in Table 5 of WO02/000879 include HDEL and the leader sequences from MnsI for ER localization, and leader sequences from Och1 and Mntl (Golgi-cis localization), from Mnn2 (Golgi medial localization), from Mnn1 (Golgi trans localization), from alpha-2,6-sialyltransferase (trans-Golgi network) and from beta-1,4-galactosyltransferase I (Golgi localization).

Localization signals thus are well known in the art and may be derived from proteins that are normally localized in the ER or Golgi for their function. Moreover, localization sequences from one organism may function in other organisms. For example, the membrane spanning region of $\alpha$-2, 6-sialyltransferase from rats, an enzyme known to localize in the rat trans Golgi, was shown to also localize a reporter gene (invertase) in the yeast Golgi (Schwientek, et al., 1995). Schwientek and co-workers have also shown that fusing 28 amino acids of a yeast mannosyltransferase (Mntl), a region containing an N-terminal cytoplasmic tail, a transmembrane region and eight amino acids of the stem region, to the catalytic domain of human GalT are sufficient for Golgi localization of an active GalT (Schwientek et al. 1995 J. Biol. Chem. 270 (10):5483-5489). Other well-documented motifs are the KDEL and HDEL motif for retention in the ER. According to particular embodiments, the ER or Golgi localization signal is from a protein that is itself localized in the ER or Golgi when functionally active. Examples of such proteins include, but are not limited to, S. cerevisiae dipeptidyl aminopeptidase A (Ste13p), human β-galactoside-α-2, 6-sialyltransferase (ST6GalI) and the human ganglioside-GM$_2$-synthase. According to further embodiments, the localization sequence is derived from one of the following proteins: Ste13p, GL2-synthase, ganglioside-GM$_2$-synthase, and α-2,6-glycosyltransferase, in particular α-2,6-sialyltransferase, most particularly β-galactoside-α-2,6-sialyltransferase.

Importantly, the Golgi apparatus is not just one homogeneous region, but has five functional regions: the cis-Golgi network, cis-Golgi, medial-Golgi, trans-Golgi, and trans-Golgi network. Vesicles from the endoplasmic reticulum (via the vesicular-tubular cluster) fuse with the cis-Golgi network and subsequently progress through the stack of cisternae that make up the Golgi apparatus to the trans-Golgi network, where they are packaged and sent to the required destination. Each region contains different enzymes that selectively modify the contents, e.g., depending on where they are destined to reside. Thus, depending on the exact targeting of the endoglucosaminidase within cells, glycosylation pathways may be modified in different ways.

For instance, the endoglucosaminidase may be targeted late in the Golgi, after sugar structures have already been added to the glycoprotein. This may, for instance, be particularly envisaged as a kind of "proofreading" or "in vivo clean-up," i.e., in situations where the desired complex glycosylation pattern is produced on the glycoproteins as well as hybrid type and/or high mannose structures (a situation often observed in yeasts modified for human-type glycosylation). There, a late-Golgi targeting of an endoglucosaminidase specific for hybrid-type and high-mannose glycosylation structures (e.g., Endo T, Endo H) ensures that the aberrantly glycosylated glycoproteins are deglycosylated (particularly to a single GlcNAc), while the glycoproteins with complex glycosylation are secreted as such. Thus, two easily separable glycopopulations are obtained. An alternative option is the late targeting of an endoglucosaminidase that hydrolyzes all glycosylation structures made in the cell (which notably need not be endoglucosaminidases with broad specificity, as some eukaryotic cells have only a limited glycodiversity, or as the eukaryotic cells may be modified to produce glycoproteins with limited glycodiversity, e.g., by deficiency of an enzymatic activity needed for complex glycosylation). This way, a uniform glycosylation pattern may be obtained in the population of glycoproteins, e.g., only non-glycosylated or only single monosaccharide-modified glycoproteins. Another option would be to target the endoglucosaminidases to an earlier stage in the ER→Golgi glycosylation pathway, while a glycosyltransferase (e.g., an additional exogenous glycosyltransferase that is targeted to later in the pathway) is active further downstream. This way, a uniform glycopopulation (e.g., of single GlcNAc-modified glycoproteins) is presented as substrate to the glycosyltransferases. This results in a uniform population of glycosylated glycoproteins. Note that this uniform glycopopulation may particularly be a uniform population of non-naturally occurring glycoforms, as typical endoglucosaminidases will also remove the inner Man$_3$GlcNAc$_2$ core structure typical of natural glycostructures. However, such structures are often less immunogenic in mammals than particular glycans produced in plant, yeast or insect cells.

It will be clear that statements made here on the targeting of endoglucosaminidases of course also apply to the targeting of other enzymes within the cell, in particular to glycosyltransferases and/or to the at least one enzyme needed for complex glycosylation used in particular embodiments. Indeed, as these enzymes are active in the ER→Golgi pathway and act sequentially, these enzymes should be carefully targeted. According to particular embodiments, the at least one enzyme needed for complex glycosylation is more than one enzyme. More particularly, the at least one enzyme is the number of enzymes needed to form a pathway for complex glycosylation. Most particularly, each of these enzymes needed for complex glycosylation is targeted so that they act sequentially and in the right order (typically, one enzyme will modify the sugar chain to a substrate for the next enzyme). According to a particular embodiment, the at least one enzyme needed for complex glycosylation is at least one N-acetylglucosaminyl transferase (e.g., GnT I, GnT II, GnT III, GnT IV, GnT V, GnT VI), at least one mannosidase (in particular mannosidase II), at least one fucosyltransferase, at least one galactosyltransferase, at least one sialyltransferase, or any combination of these enzymes.

Examples of glyco-engineered yeasts wherein complex glycosylation pathways have been engineered are extensively described in the art (see, e.g., Choi et al., 5022 2003; Hamilton et al.; Science 1244; Wildt et al., 119 2005; Hamilton et al., 387 2007; EP1211310; WO02/000879; and US2006148039). Note that the enzyme(s) needed for complex glycosylation is/are all targeted to compartments of the secretory ER→Golgi pathway and thus are not secreted.

In addition, a number of other genes may also be transformed in the glyco-engineered yeast cells described herein to ensure optimal production of complex-type glycosylated glycoproteins, such as ER and Golgi specific transporters (e.g., sym- and antiport transporters for UDP-galactose and other precursors), or enzymes involved in the synthesis of activated oligosaccharide precursors such as UDP-galactose and CMP-N-acetylneuraminic acid. Indeed, the contacting with the at least one enzyme needed for complex glycosylation may occur in the presence of specific glycosyl donors (e.g., sugar nucleotide donors) to ensure efficient and correct glycosylation.

The glycosylation status of the produced glycoprotein will depend both on the cellular system used (e.g., which enzymes are present therein) and the specificity of the endoglucosaminidase. Moreover, the time and place where these enzymes act is also important (e.g., which enzyme acts first in the ER→Golgi pathway). Thus, it is possible that cells will express solely non-glycosylated proteins, or proteins having only single GlcNAc residues (e.g., in the case of yeast cells and an endoglucosaminidase capable of hydrolyzing high-mannose and hybrid type glycans). These proteins can serve as the basis for, e.g., crystallization studies. Another possibility is that such proteins are further modified, e.g., by treatment with glycosyltransferases, resulting in proteins with the desired glycan moieties.

Alternatively, cells can be used capable of achieving the desired (typically complex) glycosylation (e.g., glyco-engineered yeast wherein the endoglucosaminidase acts after the enzymes needed for complex glycosylation (either intracellularly, e.g., in the trans Golgi or trans-Golgi network, or extracellularly)). A prerequisite in this scenario is that the endoglucosaminidase does not hydrolyze the desired sugar chains (e.g., because of its specificity, because the endoglucosaminidase is spatially and/or temporally separated from the glycosylated protein, or because the endoglucosaminidase is rendered inactive after it has removed undesired glycans). Typically, such cells will produce two populations of glycoproteins: the correctly glycosylated form and a non-glycosylated or single GlcNAc modified form (obtained, e.g., from deglycosylation of glycoproteins with hybrid-type or mannose-type glycan modifications). Although such mixed population still requires a separation step before a uniformly glycosylated population is obtained, this separation step is much easier than with traditional production methods, as the (e.g., weight, hydrodynamic properties) difference between proteins with complex glycosylation and non-glycosylated proteins is much larger than between differently glycosylated proteins.

Alternatively, it can be envisaged that the cells produce and/or secrete only correctly glycosylated proteins. For, e.g., glyco-engineered yeast, this can be achieved by targeting the endoglucosaminidase enzyme just before the at least one enzyme for complex glycosylation in the ER→Golgi pathway, in such a way that all glycoproteins are first (at least partly) deglycosylated by the endoglucosaminidase, after which they are modified by the at least one enzyme for complex glycosylation. Using the latter approach, the produced glycoproteins may have non-naturally occurring carbohydrate chains, as the endoglucosaminidase typically will remove the core $Man_5GlcNAc_2$ structure, or at least part thereof, so that the sugar chain added on the glycoprotein by the enzymes for complex glycosylation will be added on shortened base structures, such as a single GlcNAc residue. Although not naturally occurring, such complex sugar chains often also are non-immunogenic and may have other desirable properties, such as, e.g., increased stability, longer half-life, etc. Always important, but particular in the generation of such new, synthetic pathways is that the glycoprotein after modification by a first enzyme (e.g., an endoglucosaminidase) is a suitable substrate for the next enzyme (e.g., an enzyme needed for complex glycosylation).

However, it is understood that further (complex) glycosylation may also be inhibited, e.g., in order to retain solely non-glycosylated proteins or single-monosaccharide-modified proteins. Thus, according to a particular embodiment, the eukaryotic cells described herein do not comprise at least one enzyme needed for complex glycosylation, such as ER-mannosidase I, glucosidase I, glucosidase II, galactosyltransferase, sialyltransferase, mannosidase II, N-acetylglucosaminyl transferase I, and N-acetylglucosaminyl transferase II.

Such cells are not capable of complex glycosylation of glycoproteins. Nevertheless, even though (complete) complex glycosylation is normally not achieved in such cells, it may be possible to target an endoglucosaminidase with a particular specificity to a place in the ER→Golgi glycosylation pathway where it ensures that the glycoprotein after it has been contacted with the endoglucosaminidase is again a target for the following enzymes. This way, new synthetic pathways may be generated. It may, for instance, be possible in a cell that lacks N-acetylglucosaminyl transferase I to target an endoglucosaminidase just before the galactosyltransferase and sialyltransferase. This way, only the galactosyltransferase and sialyltransferase will act on the (partially) deglycosylated protein (e.g., a single-GlcNAc-modified protein), thus yielding a protein with non-naturally occurring complex glycosylation.

Whereas cells for the production of glycoproteins as described herein will typically be provided in the form of a cell culture, this need not necessarily be the case. Indeed, the cells producing the glycoproteins may be part of an organism, e.g., a transgenic animal or plant. According to a particular embodiment, plants comprising the glycoprotein and endoglucosaminidase-containing cells as described in the application are also envisaged. Typically, plants will have multiple of these cells, particularly also in different organs and/or tissues.

The eukaryotic cells described herein are particularly well suited for glycoprotein production. According to particular embodiments, the glycoproteins are enriched for a specific glycoform, particularly single GlcNAc-modified glycoproteins. Thus, methods are provided for producing glycoproteins modified with a single GlcNac moiety in a eukaryotic cell, comprising the steps of:

providing a eukaryotic cell deficient in expression and/or activity of an endogenous UDP-galactose 4-epimerase (GalE) and comprising a first exogenous nucleic acid sequence encoding an endoglucosaminidase enzyme and a second exogenous nucleic acid sequence encoding a glycoprotein in conditions suitable for expressing the endoglucosaminidase enzyme and the glycoprotein; and recovering the glycoprotein after it has been intracellularly or extracellularly contacted with the endoglucosaminidase.

The glycoproteins with a single GlcNAc residue may be the only glycoform of the glycoprotein produced by the cell (i.e., a uniform glycopopulation is produced), i.e., there are no other N- or O-glycans present on the glycoprotein.

The methods as described herein may be further adapted to ensure that the contact between glycoprotein and endoglucosaminidase occurs under optimal circumstances (i.e., to ensure optimal activity of the endoglucosaminidase on the glycoprotein). For instance, when the contact occurs intracellularly, the endoglucosaminidase may be targeted to the (desired place in the) Golgi or ER where it exerts its function on the glycoprotein. Depending on, e.g., further transglycosylation envisaged in or outside the cell, the desired place may vary, as described above. According to particular embodiments, the intracellular contact occurs in the Golgi or ER.

Both the endoglucosaminidase and the glycoprotein may also be secreted and the contact may happen extracellularly. Depending on the cells and endoglucosaminidase that are used however, the optimal growth and production conditions for the cells (e.g., pH, temperature) may differ from the optimal conditions for enzymatic activity. Thus, the medium where the extracellular contact between the glycoprotein and the endoglucosaminidase takes place may be adjusted for optimal enzymatic activity of the endoglucosaminidase. According to a particular embodiment, the conditions of the medium wherein the extracellular contact takes place are adjusted for optimal enzymatic endoglucosaminidase activity. According to a further particular embodiment, the pH of the medium wherein the extracellular contact takes place is adjusted for optimal enzymatic endoglucosaminidase activity. Typically, this may be done by a pH shift of the medium after the cells have been allowed to produce and secrete both glycoproteins and endoglucosaminidases. In general, such pH shift will be a downshift, as endoglucosaminidases usually are physiologically active in an acidic environment. According to another particular embodiment, the temperature of the medium is adjusted for optimal enzymatic activity. Note that the adjustment of growth and production conditions may be done just before endoglucosaminidase activity, or that the conditions may already been adapted during cell growth. For instance, Pichia cells can grow and produce proteins in a fairly acidic medium, which thus is already adjusted for optimal activity of particular endoglucosaminidases. However, as some eukaryotic cells are dependent on N-glycosylation for their integrity, it might be beneficial to buffer the pH of the growth medium to a pH at which the endoglucosaminidase is not active, and downshift the pH only after the protein production is finished.

As another important aspect of the disclosure, glycoproteins are provided comprising a single GlcNAc N-glycan and are devoid of mucin type O-glycans. According to the disclosure, the glycoprotein is obtained by expressing the glycoprotein in a mammalian cell line or organism wherein the mammalian cell or organism comprises an exogenous nucleic acid sequence encoding an endoglucosaminidase enzyme. The mammalian cell line or organism is deficient in expression and/or activity of an endogenous UDP-galactose 4-epimerase (GalE).

Of note, all of the previously specified features and embodiments of the disclosure are of use to further specify the process by which the glycoproteins that comprise a single GlcNAc N-glycan and are devoid of mucin type O-glycans are obtained.

It is to be understood that although particular embodiments, specific configurations as well as materials and/or molecules, have been discussed herein for cells and methods according to this disclosure, various changes or modifications in form and detail may be made. The following examples are provided to better illustrate particular embodiments, and they should not be considered limiting the application. The application is limited only by the claims.

EXAMPLES

Example 1: Generation of a HEK293S Glycodelete Cell Line

This was done as described in WO 2010/015722 and Meuris et al. (*Nat. Biotechnol.* 2014 32(5):485-9).

Briefly, to avoid in vitro deglycosylation we implement in vivo de-N-glycosylation in a HEK293S cell-line. Identification and cloning of a fungal gene (Genbank Acc. No. CS423050) that encodes an endoH-type endoglycosidase, denoted as endoT because it was cloned from the filamentous fungi *Trichoderma reesei* (PhD thesis Ingeborg Stals, Ghent University, 2004) allows us to do so. The work is carried out in a glucosaminyltransferase I negative HEK cell-line, (Reeves, Callewaert et al., *PNAS* 99 (2002): 13419-13424). This cell-line almost exclusively produces $Man_5GlcNAc_2$—N-glycans, which are hydrolyzed in the chitobiose bond by endoH-type endoglycosidases.

EndoT is secreted by *T. reesei* (now designated as *Hypocrea jecorina*), which is indicative for the fact that it is adapted to folding in the eukaryotic secretion pathway. In order not to interfere with the function of N-glycans in protein folding, endoT is targeted to the trans-golgi/trans-golgi network.

Strategy

Targeting the endoT enzyme to the trans-golgi/TGN of the HEK293 S cell-line is achieved by fusing the trans-golgi-targeting signal of a golgi-retained glycosyltransferase. Most golgi-resident glycosyltransferases are subject to proteolytic splicing in the stalk region to a lesser or greater extent (Jaskiewicz, *J. Biol. Chem.* 271(42) (1996), 26395-26403). The human β-galactoside-α-2,6-sialyltransferase (ST6GalI) or the human ganglioside-$GM_2$-synthase (GalNAcT) N-terminus is fused to the N-terminus of the full-length endoT enzyme. The 3-galactoside-α-2,6-sialyltransferase (ST6GalI) has been characterized better and its N-terminus is retained in the trans-golgi, but it contains several cleavage sites and is probably subject to proteolytic processing (Kitazume-Kawaguchi et al., *Glycobiology* 9(12) (1999), 1397-1406).

The GM2-synthase N-terminus is shorter: only the first 27 amino acids seem to determine trans-Golgi retention (Uliana et al., *Traffic* 7 (2006), 604-612) and only contains one cathepsin-D splice site between amino acids 22 and 23 (GL-LYAST) (Jaskiewicz, *J. Biol. Chem.* 271(42) (1996), 26395-26403). If too much cleaved endoT fusion protein is secreted, these sequences are mutated to a non-spliced sequence.

To evaluate proteolytic cleavage and targeting on the one hand and the efficiency of the in vivo de-N-glycosylation on the other, expression constructs for transient mammalian expression are made, using the mammalian expression vector pCAGGS (Niwa et al., *Gene* 108 (1991), 193-200). MYC-tagged constructs for the two fusion proteins allow for subcellular localization experiments and to assess secretion. Subcellular localization experiments are carried out using an anti-MYC antibody immunofluorescence microscopy and a trans-golgi-targeting pHluorin construct (http://www.bristol.ac.uk/synaptic/research/projects/mechanisms/phluorins.htm) as a positive control. Secretion of the MYC-tagged endoT protein is evaluated by Western blot with an anti-MYC antibody and by using a MYC-tagged endoT without an N-terminal golgi-targeting sequence as a negative control.

A soluble, secreted form of the glycoprotein hemagglutinin H3 is used to co-transfect to the HEK293 S cell-line and allows evaluation of the de-N-glycosylating activity of the endoT fusion protein. Such a hemagglutinin coding sequence is also cloned into the pCAGGS vector. As hemagglutinin is intracellularly deglycosylated by endoT, a shift in molecular weight is observed on SDS-PAGE.

The best Golgi-targeting signal is then used to make a final construct, with the chosen fusion protein. Constitutive as well as tetracycline-inducible expression is envisaged.

For tetracycline-inducible expression, the pcDNA4/TO (Invitrogen) vector is used. A stable cell-line is thus produced by selection with zeocin. The HEK293S GnTI–/– cell-line already contains a pcDNA6/TR construct, which encodes the Tet-repressor protein. This is constitutively and stably expressed and represses transcription from the pcDNA4/TO plasmid (Invitrogen) until tetracycline is added.

For constitutive expression, any mammalian expression vector, containing a constitutive promoter and a selection marker (not blasticidin, already in use for pcDNA6/TR) can be used.

Example 2. In Vivo De-N-Glycosylation of Glycoproteins by Targeting of the Fungal endoT Enzyme to the Secretory Pathway of Eukaryotic Organisms Transient Transfection of endoT Constructs in Mammalian Cells pCAGGS-hST-endoT, pCAGGS-hST-endoT-myc, pCAGGS-hGalNAcT-endoT and pCAGGS-hGalNAcT-endoT-myc were produced as described in WO 2010/015722 and Meuris et al. (Nat. Biotechnol. 2014 32(5):485-9). These plasmids and also the empty pCAGGS plasmid were used to transiently transfect the Hek293 S-Flt3 cell-line. As a negative control, the cells were also transfected without DNA. Cells were seeded at 200.000 cells per well in a six-well plate two days prior to transfection so that they are at least 85%-90% confluent at the day of transfection. Six hours prior to transfection, half of the medium was replaced by serum free medium and three hours prior to transfection, all medium (3 mL) was replaced by 2 mL of serum-free medium. DNA lipoplexes were prepared by combining 4 μg of plasmid DNA with L of lipofectamine 2000 in 500 μL serum free medium and incubating for 20 minutes at room temperature. After incubation, the lipoplexes were added to the cells and incubated overnight. The next morning, 1 mL of medium containing 30% serum was added to each well, to make a total serum concentration of 10%.

At the same time of transfection, 2 μg/mL Tetracycline Hydrochloride was added to each well to induce production of the Flt3 extracellular domain (secreted). 0.5 ml of the medium (without cells) was collected 48 and 72 hours after transfection and stored at −20° C. for later analysis.

Sample Preparation of Medium Samples for Flt3 Detection

The medium samples containing BSA (from the fetal calf serum) were cleaned up using Chelating sepharose 6B beads loaded with nickel ions.

Bead Preparation:

500 μL beads were loaded with 1 mL of 100 mM nickel sulphate and incubated for 5 minutes @ RT. They were spun down for 1 minute at 500 g in a microcentrifuge and the supernatant was discarded. After this, they were washed with 1 mL of PBS, spun down for 1 minute at 500 g and the supernatant was discarded. This wash step was repeated five times, and after the last wash, 500 μL of PBS was added.

Selective Enrichment of His-Tagged Flt3:

to a sample of 250 μL an equal amount of 2×PBS was added. 25 μL from the beads slurry (prepared as described above) was added to this, and the mix was incubated on a rotating platform for one hour.

After this, the beads were spun down for 1 minute at 500 g and the supernatant was discarded. 0.5 mL of PBS was added to the beads, they were spun down for 1 minute at 500 g and the supernatant was discarded. This wash step was done three times in total.

The beads were resuspended in 250 μL of PBS. Of the resulting samples, 20 μL was taken, to which 10 μL of 3× Laemlli buffer with β-mercapto ethanol was added and the samples were cooked for 5 minutes.

Detection of Secreted Flt3 by Western Blot

After sample preparation, 30 μL of each sample was loaded onto a 10% SDS-PAGE gel and run. The gel was blotted semi-dry to a nitrocellulose membrane and detection of the his-tagged Flt3 protein was performed with a primary penta-his antibody diluted 1/1000 and a secondary anti-mouse IgG1 diluted 1/5000.

Detection of Secreted endoT Constructs by Western Blot

The same medium samples were also used to asses secretion of (proteolytically cleaved) endoT fusion proteins. 10 μL of 3× Laemlli buffer with β-mercapto ethanol was added to 20 μL of the original samples, and these were run on a 10% SDS-PAGE gel. After blotting to a nitrocellulose membrane, detection was performed using an anti-myc primary antibody diluted 1/3000 and an anti-mouse secondary antibody diluted 1/5000.

Results

The Hek293S-Flt3 was generated by the group of Prof. S. Savvides from the parental cell-line Hek293 S-RicR, which produces almost exclusively Man5GlcNAc2 N-glycans. It is a stable transfectant line for the his-tagged extracellular domain of the human Flt3 receptor, this protein goes through the secretory pathway.

Transient Transfection of endoT Constructs into Mammalian Cells

The transfection protocol used allows us to transfect the cells with an efficiency of about 30-40% (assessed by FACS, results not shown). Daily microscopic observation showed no significant cell-death or a slower growth than the negative control well (transfection with no DNA) after transfecting any of the endoT fusion proteins or the empty pCAGGS plasmid.

Sample Preparation of Medium Samples for Flt3 Detection

Because of the presence of a high amount of bovine serum albumin (BSA) (runs at ~66 kDa) in the samples, and the fact that the secreted, non-deglycosylated Flt3 receptor runs at about 70 kDa, immunodetection of the Flt3 and especially detection of the deglycosylated forms of this protein, which run in the BSA area at a slightly lower molecular weight than 70 kDa, is obscured by aspecific staining by the excess BSA and blocking of the actual Flt3 signal. Therefore it is convenient to purify the Flt3 from the samples to a certain extent, using a cleanup step with nickel loaded chelating sepharose beads. This step selectively enriches the Flt3 molecules in the sample, since they are his-tagged, and detection becomes possible.

Flt3 Western Blot: Processing by endoT

The secreted Flt3 extracellular domain contains nine putative N-glycosylation sites (Rosnet et al., 1993). Up to this date, seven of these sites have been confirmed to be modified with N-glycans (personal communication, K. Verstraete). It is expected that removal of at least some of the glycans by the endoT fusion proteins will cause a band-shift on Western blot, and this is indeed the case (not shown). Two days post transfection and induction, some processing of the Flt3 produced by the pCAGGS-hST-endoT and pCAGGS-hST-endoT-myc transfected cells can be observed. After three days, no more fully glycosylated Flt3 can be observed in any of the samples produced by endoT transfected cells. The fact that the Flt3 bands originating from the cells transfected with the myc-tagged endoT fusion proteins show the same behavior as the ones from the non-myc-tagged endoT fusion protein transfected cells, in both cases, is indicative for the fact that the c-myc tag does not seriously interfere with the function of the fusion proteins.

Detection of endoT Constructs by Western Blot

Both endoT fusion protein constructs were also tagged C-terminally with a c-myc tag. This allows for assessment of proteolytic processing and subsequent secretion of the golgi-luminal domain of the endoT fusion proteins, which should then be detected in the supernatant by Western blot. This is indeed the case for the endoT fused N-terminally to the targeting domain of the human GM2-synthase (pCAGGS-hGalNAcT-endoT-myc) (not shown). Processing at a cathepsin D-like splice site (GL—LYAST) between amino acids 22 and 23 would give rise to a secreted fragment of ~39.1 kDa (non-glycosylated, myc-tagged form). The secreted fragment has about this size. The Coomassie stained SDS-PAGE gel shows small but clearly defined bands in the lanes loaded with supernatant samples from pCAGGS-hGal-NAcT-endoT and pCAGGS-hGalNAcT-endoT-myc transfected cells, with a slight difference in MW, attributed to the presence or absence of the myc-tag (1.2 kDa) (not shown).

The endoT fused to the targeting domain of the human β-galactoside-α-2,6-sialyltransferase (hST) does not seem to be secreted in significant amounts, since no fragment can be detected on Western blot three days after transfection with the pCAGGS-hST-endoT-myc plasmid. The first 27 amino acids of the fusion protein make up for the cytoplasmic and transmembrane domains. This means that theoretically anywhere between amino acid 27 and 100 (this is the portion of the hST used), proteolytic splicing could occur and give rise to a fragment of 38.6 kDa to 46.5 kDa. Even if N-glycans are present (four sites on endoT, no sites on hST targeting domain), taking into account that N-glycans are of the Man5GlcNAc2-form, the protein would outside of the BSA occluded area around 66 kDa (~60-70 kDa) and thus would be detected on Western blot. Also, the Coomassie stained SDS-PAGE gel shows no extra bands not present in the negative control lanes (transfection with empty pCAGGS) (not shown). All this indicates that the endoT protein indeed remains inside the cell and thus is efficiently targeted.

Example 3. Generation of a GlycoDoubleDelete Cell Line

Strategy

Our aim is to generate a cell line completely devoid of mucin type O-glycosylation. Combining this cell line with GlycoDelete engineering would then result in a "GlycoDoubleDelete" cell line, with both O- and N-glycan heterogeneity significantly reduced. These cell lines would be useful to produce glycoproteins that require their N-glycans to mediate correct folding, but do not require a fully matured N- or O-glycan to function. For example, in crystallography, glycan heterogeneity can hamper crystal formation. In addition glycans are known to influence the efficacy, activity and stability of biopharmaceuticals, but glycan heterogeneity can vary from batch to batch, which implicates that the properties of the pharmaceutical protein can vary equally.

An enzymatic strategy similar to the one used in GlycoDelete cells is impossible for O-glycans. In GlycoDelete cells, the endoT enzyme recognizes all N-glycans that are synthesized. For O-glycans, no such enzymes, which recognize every member of the complex and diverse mixture of mucin type O-glycans, are known. Therefore, we wanted to target the O-glycosylation biosynthesis pathway by knocking out a gene in the initial steps of O-glycan assembly. Unlike N-glycans, which all share the trimannosyl core, mucin type O-glycans structurally have little in common. GalNAc linkage to serine or threonine initiates O-glycosylation. It is the only common residue of the different mucin-type O-glycans. However, targeting the O-glycosylation initiating enzymes, the polypeptide-GalNAc-transferase (ppGalNAcT) family, would be a tedious task since the ppGalNAcT family has more than 20 members. The one shared feature we can target is the substrate used by the ppGalNAcT family: UDP-GalNAc. There are two routes by which UDP-GalNAc is provided: salvage from external or internal metabolized molecules or de novo assembly from the central carbon metabolism, via UDP-GlcNAc. The UDP-GlcNAC to UDP-GAlNAc epimerization is catalyzed by UDP-galactose-4'epimerase (GalE). During experiments studying receptor mediated endocytosis in CHO cells, GalE was inadvertently knocked out, which resulted in a deprivation of UDP-GalNAc and UDP-Gal (Krieger et al., *J. Mol. Biol.* 150:167-184 (1981)). Proteins produced in these cells were devoid of any mucin type O-glycan (Kingsley et al., *Cell* 44:749-759 (1986)). Therefore we decided to target the GalE gene in HEK293 cells.

Figure 1:
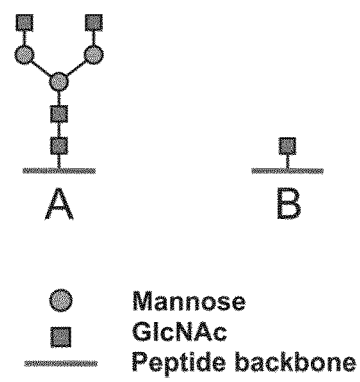
FIG. 1: A typical N-glycan as found on (A) a 293s GalE KO-produced protein and (B) a 293 sGlycoDoubleDelete-produced protein.

According to the authors, the selection method used to isolate the CHO GalE KO had only yielded one GalE-deficient clone. In addition, the experiment could never be repeated. Therefore we chose not to repeat those procedures, but design a new approach. Our aim was to knock out GalE in HEK293s cells by making use of genome editing tools, thereby creating O-glycosylation-deficient HEK293s cells that decorate their proteins with N-glycans as depicted in FIG. 1, Panel A, and no O-glycans. By applying this approach in GlycoDelete cells we wanted to tackle heterogeneity originating from both N- and O-linked glycans in these so-called GlycoDoubleDelete cells (FIG. 1, Panel B).

To ensure genome editing tools actually edit the target sequences, we followed a bottom up approach by first thoroughly characterizing newly designed targeted nucleases in an in vitro assay. In addition we also found the correct conditions to perform a Surveyor assay (described in the materials and methods section), which allowed in vivo testing. To increase our chances for success, we focused on generating KOs by using WT Cas9 instead of nickase Cas9, as the cleavage frequency of the latter is much lower.

A screening method was needed that allows for relatively easy screening in a short time span. Several phenotype-based screening methods were used, but due to the lack of a positive control it was always unclear if the screening method was failing or if there was just no knock out in the screened cells. Screening at the genomic level was also problematic, as we needed about a million cells per genomic DNA prep, which requires expanding the cell line. Moreover, we had to clone the PCR amplified fragment in a vector for sequencing, a labor-intensive and time consuming strategy. The problems encountered with screening were approached both at genomic and phenotypic level. On the genomic level, we optimized a combination of fast genomic DNA isolation methods and specific robust polymerases that allow screening a few dozen of clones within a reasonable timespan. On a phenotypic level, we expressed hGM-CSF in the potential GalE KO clones. We previously showed that removal of O-glycan sialic acids can be detected on SDS-PAGE gel, so a total removal of the O-glycans should result in an even larger molecular weight shift (L. Meuris et al., *Nat. Biotechnol.* 32:485-489 (2014)).

Guide Assembly and Activity Evaluation

Figure 2:
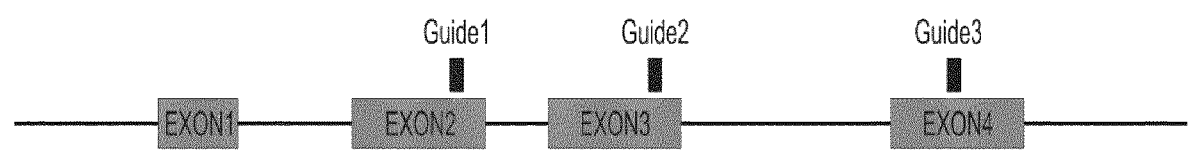
FIG. 2: Symbolic representation of the first four exons of the GalE gene and the positions of the three Guides (not to scale).

Three guides targeting exon 2, 3 and 4 of the GalE gene were designed with an online tool available from MIT (CRISPR.MIT.EDU). Their sequences can be found in Table 1. The loci of the GalE gene targeted by these guides are indicated in FIG. 2. The guides where then cloned into the PX458 vector from Feng Zhang's lab following the instructions from F. A. Ran et al. (genome engineering using the CRISPR Cas9 system, *Nat. Protoc.* 8:2281-2308 (2013)). Apart from a cloning site for the guide, this vector also has a Cas9-GFP expression cassette in which expression of a GFP gene is coupled to Cas9 expression. Cells expressing GFP must also express the Cas9 protein, because its expression is driven from the same promoter. The two coding sequences are separated by 2A sequences, a DNA element of viral origin that causes the ribosome to skip a certain stretch of CDS in the resulting mRNA, generating two separate polypeptide chains from the same mRNA.

TABLE 1

Assembly of the ordered oligos used to clone the guides in the PX458 vector

| Guide | Guide sequence | SEQ ID NO: |
|---|---|---|
| Guide 1 | TGGAAGTTATCGATGACCAC | 6 |
|  | GTGGTCATCGATAACTTCCA | 7 |
| Guide 2 | CTTTTTGAAGAGACGCTGTA | 8 |
|  | TACAGCGTCTCTTCAAAAAG | 9 |
| Guide 3 | CTTCTGCACCGACTCGCCCA | 10 |
|  | TGGGCGAGTCGGTGCAGAAG | 11 |

Figure 3:
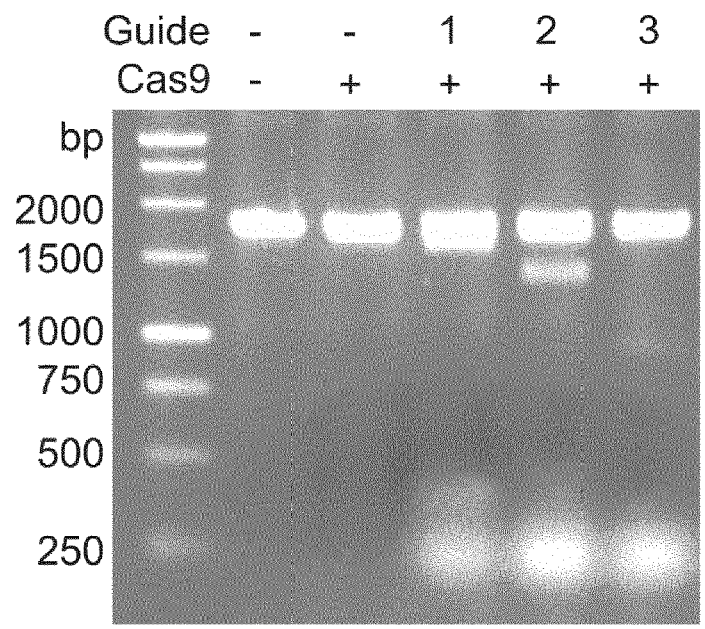
FIG. 3: In vitro digestion of a fragment of the GalE gene with three different guides. All three guides show bands at the expected molecular weight. The intense signals at low molecular weight are the in vitro-produced guide RNA.

Before attempting to obtain genome editing events in living cells, we assessed cleavage efficiency of the selected guides by digesting PCR amplified DNA of the target region with in vitro synthesized guide RNA and recombinantly produced Cas9. As shown in FIG. 3, all three guides process a 1805 bp long PCR amplified fragment of the GalE gene to fragments of the expected size (Table 2).

TABLE 2

Expected fragment sizes of the in vitro cleavage assay (in bp)

| Undigested | Guide 1 | Guide 2 | Guide 3 |
|---|---|---|---|
| 1804 | 156 | 441 | 905 |
|  | 1649 | 1363 | 900 |

Figure 4:
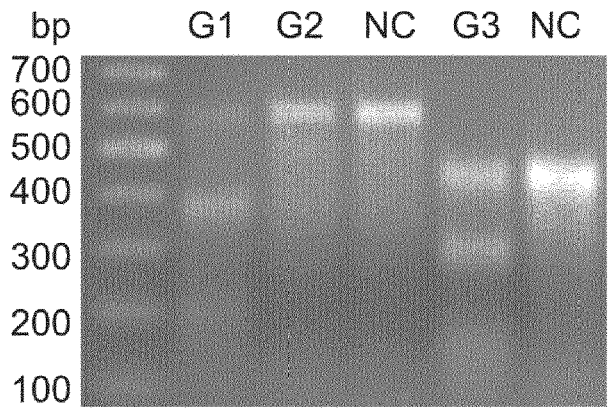
FIG. 4: Surveyor assay on DNA derived from cells treated with CRISPR/Cas9 guide one (G1), guide two (G2) and guide three (G3). NC are negative controls from WT cells.

To further characterize the guides we transfected 1 million cells with HEK293s cells with the three different guides. After 72 hours, GFP positive cells were FACs sorted in a pool. The cells from this pool were harvested and their genomic DNA was isolated. The targeted region was PCR-amplified. By making use of a Surveyor assay (FIG. 4), we could conclude that guide one and guide three had been able to cleave the target fragment in vivo while guide two showed no activity.

Table 3 displays the expected fragment sizes.

TABLE 3

Expected fragment sizes of the Surveyor assay (in bp)

|  | Guide 1 | Guide 2 | Guide 3 |
|---|---|---|---|
| Control | 577 | 577 | 454 |
| Digested | 202 & 375 | 89 & 488 | 288 & 166 |

HEK293sGalE$^{-/-}$ KO generation and analysis
Development of a Genotypic Screen and Application to Clone Selection Having successfully shown that guide 1 and 3 can both achieve in vivo genomic editing, we transfected HEK293s cells again with guide 1 and 3. Seventy-two hours post-transfection, the cells were FACS sorted to one cell per well in a 96-well plate. 34 clones grew to a stable single cell line-derived colony and were expanded. Of each clone, we harvested 2*10$^5$ cells to lyse in 100 µl QuickExtract buffer for genomic DNA extraction. Because this method does not require a DNA purification step, it results in a crude extract of genomic DNA mixed with other cellular lysate. The high amounts of contaminants make it difficult to measure the genomic DNA concentration in the sample. In an effort to add similar amounts of genomic DNA to the different PCR reactions, we each time lysed the same amount of cells in the same amount of buffer and used 1 µl of that crude genomic DNA mix per 10 µl of total PCR volume. We also found that our standard high fidelity polymerases often suffer from the residual products present in the crude genomic DNA extract, which then resulted in poor or no amplification of the targeted region. Therefore it was essential to use Kapa HiFi as a polymerase, which appeared to be able to handle a very broad variability in genomic DNA quality. In the past this PCR product was cloned in a TOPO vector, because direct sequencing on a PCR Product often resulted in bad reads due to a low DNA purity. However purification of the PCR amplicon with magnetic beats resulted in a highly pure DNA sample, which allowed direct Sanger sequencing by using nested primers. This eliminated the need of intermediate cloning steps, and consequently reduced the analysis time multiple days. Sanger sequencing revealed editing in 21 clones, 13 were still wild type.

Figure 5:
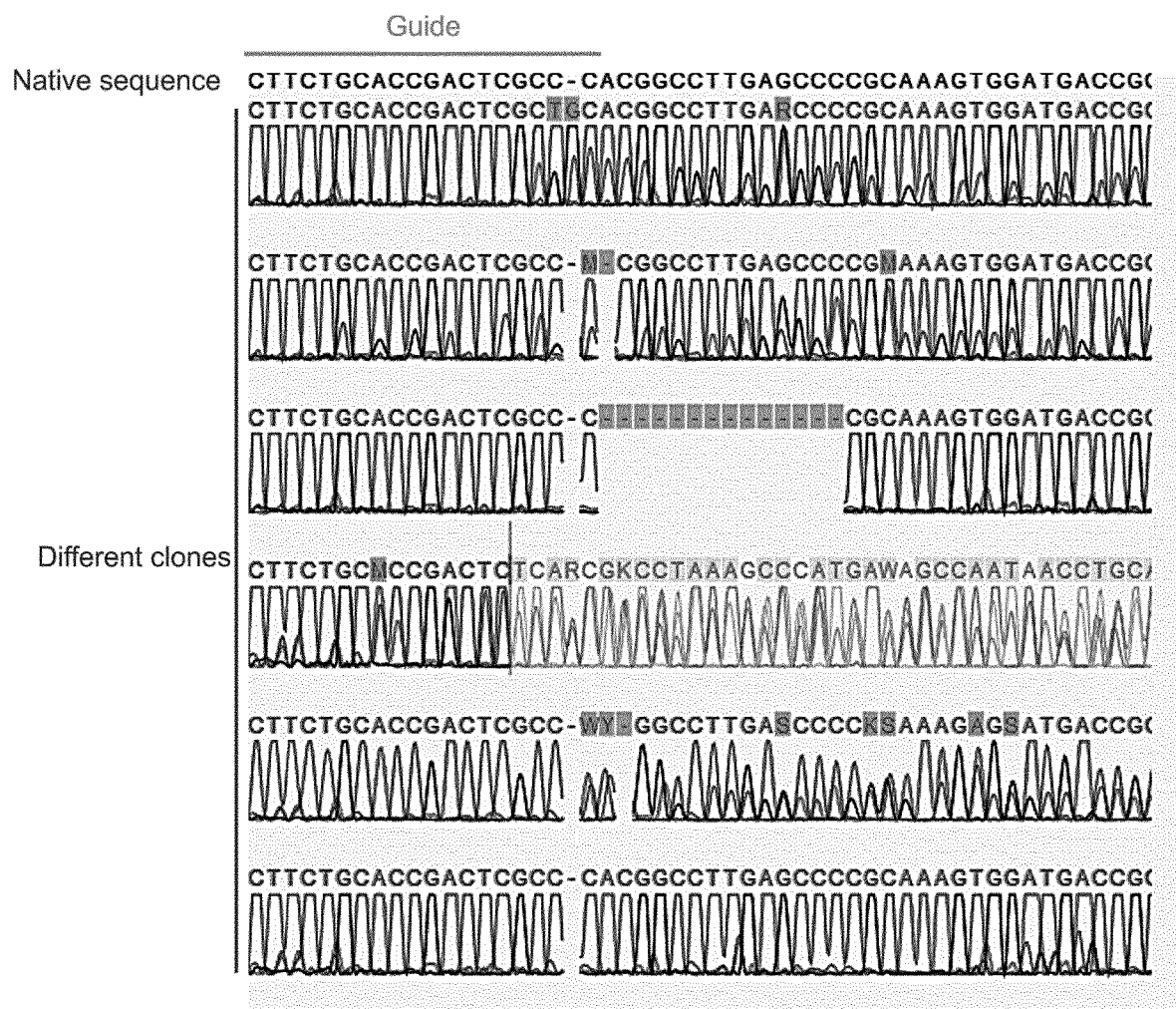
FIG. 5: Alignment of different Sanger sequencing reads (assigned with "different clones") to the native sequence on top. The position of the guide 3 is indicated with a line on top of the figure. Indels in mutant sequences are marked with a box. Most reads are composed of multiple tracks, due to different editing in the different alleles. (SEQ ID NOS:47-53.)

Due to polyploidy in HEK293 cells, it is difficult to determine how the different GalE alleles are edited. Previously, whole genome sequencing of HEK293 cells revealed a ploidy level of 2.72 at the position of the GalE gene in HEK293s cells and 3.48 in HEK293sGlycoDelete cells (Lin, Y.-C. et al. Genome dynamics of the human embryonic kidney 293 lineage in response to cell biology manipulations. *Nat. Commun.* 5, (2014)). When sequencing the PCR amplified fragments with Sanger sequencing, reads from the different alleles are superimposed on each other and are difficult to interpret as is illustrated for guide 3 in FIG. 5.

To tackle the problem of superimposed sequencing data, we used an online tool called TIDE. This tool deconvolutes and decomposes Sanger sequencing reads to estimate which indels occur in which frequencies (E. K. Brinkman, T. Chen, M. Amendola, and B. van Steensel, Easy quantitative assessment of genome editing by sequence trace decomposition, *Nucleic Acids Res.* 42, e168-e168 (2014)). TIDE is designed to analyze data from a pool of cells as an alternative for the Surveyor assay. However, we redirected the tool to find allelic variances. TIDE analysis revealed that nine clones appeared to have loss of function mutations in every allele.

From those nine clones, we PCR amplified the edited region with primers carrying illumina sequencing adapters. This allowed us to deep sequence the amplicon and generate a comprehensive analysis of different indels in the different alleles. By counting the coverage of each indel, editing frequencies were calculated. As can be seen in Table 4, the results from TIDE and the illumina sequencing coincide for most of the clones.

TABLE 4

Comparison of the indels detected in nine different clones, both by illumina sequencing and Sanger sequencing. The indel frequencies were calculated by counting the coverage for each indel in the case of illumina sequencing and by the online tool TIDE in the case of Sanger sequencing. The number under INDEL indicates an insertion (−) or deletion (+) of the indicated number of base pairs. Note that often different mutant sequences occur within the same clone due to the polyploidy of the cells. The first number of the clone name refers to the Guide used in these cells.

| Clone | Illumina NextSeq | | | SangerSeq |
|---|---|---|---|---|
| | INDEL | Frequency | Coverage | TIDE |
| 3.1 | −1 | 62.00% | 142110 | 65.80% |
| | −4 | 34.00% | | 32.50% |
| 3.2 | −14 | 95.30% | 171132 | 95.80% |
| | −1 | 4.60% | | |
| 3.3 | −1 | 100.00% | 177916 | 80.00% |
| 1.1 | −7 | 64.00% | 482992 | 62.00% |
| | −7 | 36.00% | | |
| 3.4 | −1 | 64.50% | 264704 | 64.70% |
| | −7 | 35.00% | | 28.80% |
| 1.2 | −10 | 31.00% | 450259 | 20.00% |
| | +1 | 26.90% | | 37.50% |
| | +1 | 18.90% | | |
| | −1 | 18.90% | | 13.80% |
| 3.5 | −7 | 100.00% | 264704 | 65.50% |
| 3.6 | −9 | 94.50% | 384916 | 65.80% |
| | −1 | 2.90% | | |
| 3.7 | −6 | 50.00% | 260086 | 45.20% |
| | −1 | 45.90% | | 49.10% |

Further Clone Selection Based on hGM-CSF Processing

Figure 6:
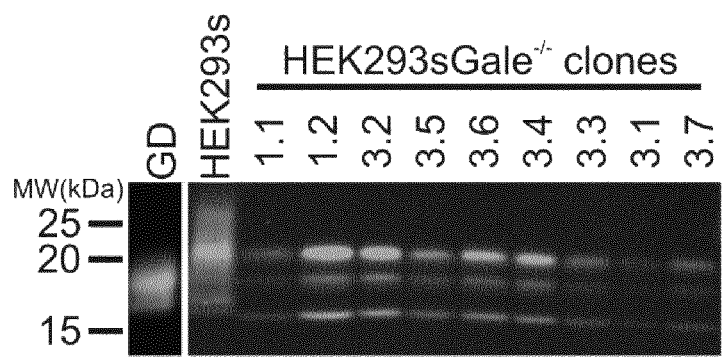
FIG. 6: hGM-CSF expressed in HEK293sGlycoDelete cells (GD), HEK293s cells and in the different HEK293sGalE$^{-/-}$ clones. HEK293s is the control in which hGM-CSF still carries full size N-glycans as well as O-glycans. In HEK293sGD cells (GD lane), N-glycans are small and homogenous, and the remaining smearing is due to O-glycans. The three discrete bands observed in HEK293sGalE$^{-/-}$ expression correspond from high to low molecular weight with hGMCSF decorated with two, one and no occupied N-glycosylation sites. Due to the lack of UDP-Gal and UDP-GalNAc, N-glycan heterogeneity is probably also reduced as compared to HEK293 s-produced hGM-CSF.

To check the effects of this KO on O-glycosylated proteins, we transfected the different clones with an human GM-CSF (hGM-CSF) expression plasmid. hGM-CSF is a small cytokine of which we know that it can carry up to four O-glycans of varying structure and up to two N-glycans. Its heterogeneous O-glycosylation causes smearing on an SDS-PAGE gel. This is illustrated in FIG. 6, GD lane and HEK293s lane. The absence of such extensive smearing in hGM-CSF samples produced in our clones would be indicative of a lack of mucin type O-glycosylation. Indeed, analysis by Western blot shows that only three discrete bands, representing three N-glycoforms can be distinguished and no smearing is apparent. From low to high molecular weight, the bands represent hGM-CSF decorated with no, one and two N-glycans. Because N-glycans are also impeded from further maturation due to the lack of UDP-Gal and UDP-GalNAc, the three remaining glycoforms separate in discrete bands on SDS-PAGE gel as depicted in FIG. 6. Consequently, we conclude that none of the selected clones still expresses a functional GalE enzyme.

Figure 7:
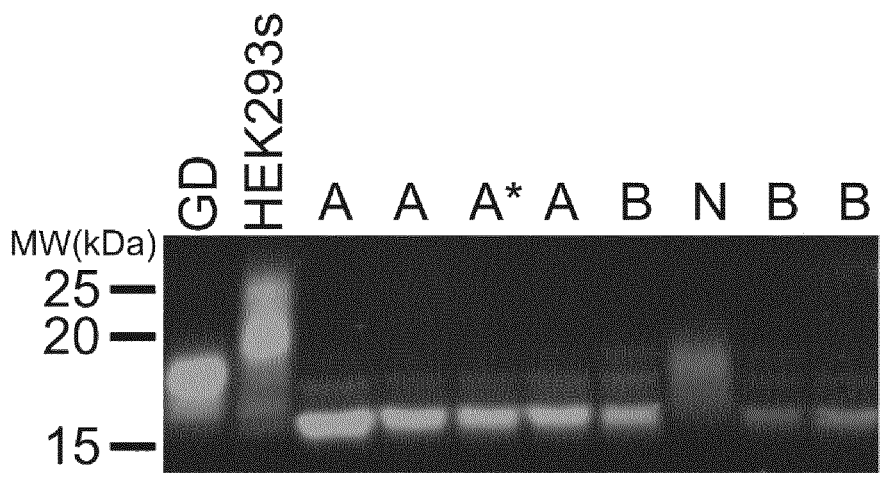
FIG. 7: hGM-CSF expressed in 293sGlycoDelete cells (GD), HEK293s cells and samples from possible HEK293sGlycoDoubleDelete clones (labeled with A, B and N). The lane labeled with N is hGM-CSF from a clone that still expresses functional GalE. Lanes labeled with B are hGM-CSF from clones with a successful GalE KO, but with lower levels of endoT processing. Lanes labeled with A are hGM-CSF from clones with both a successful GalE KO and relatively high endoT N-glycan processing levels. The starred clone was selected for further characterization.
Figure 8A:
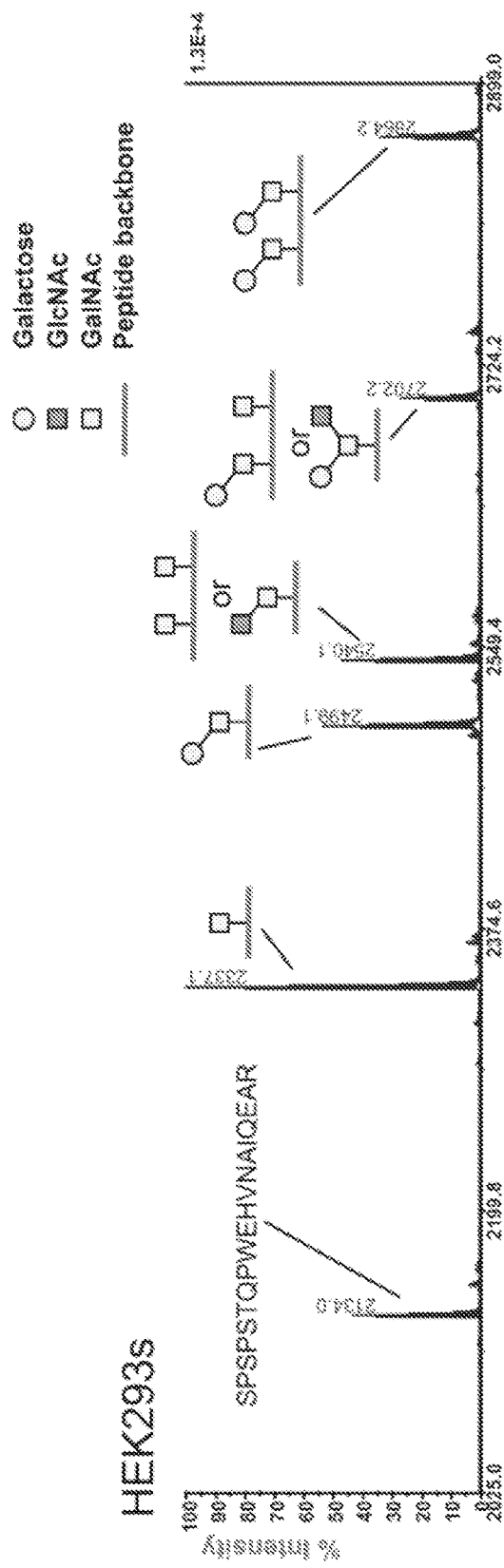
FIGS. 8A and 8B: MALDI-TOF analysis of trypsinized hGM-CSF. The tryptic peptide SPSPSTQPWEHVNAIQEAR (SEQ ID NO:3) (2134 Da) contains four possible O-glycosylation sites. In HEK293s (top spectrum) and HEK293sGlycoDelete cells (second spectrum) we detected various types of O-glycans attached to this peptide. Both in hGM-CSF from HEK293sGalE$^{-/-}$ (third spectrum) and HEK293sGlycoDoubleDelete (bottom spectrum) cell lines, these peaks are absent and only the naked peptide is detected.
Figure 8A:
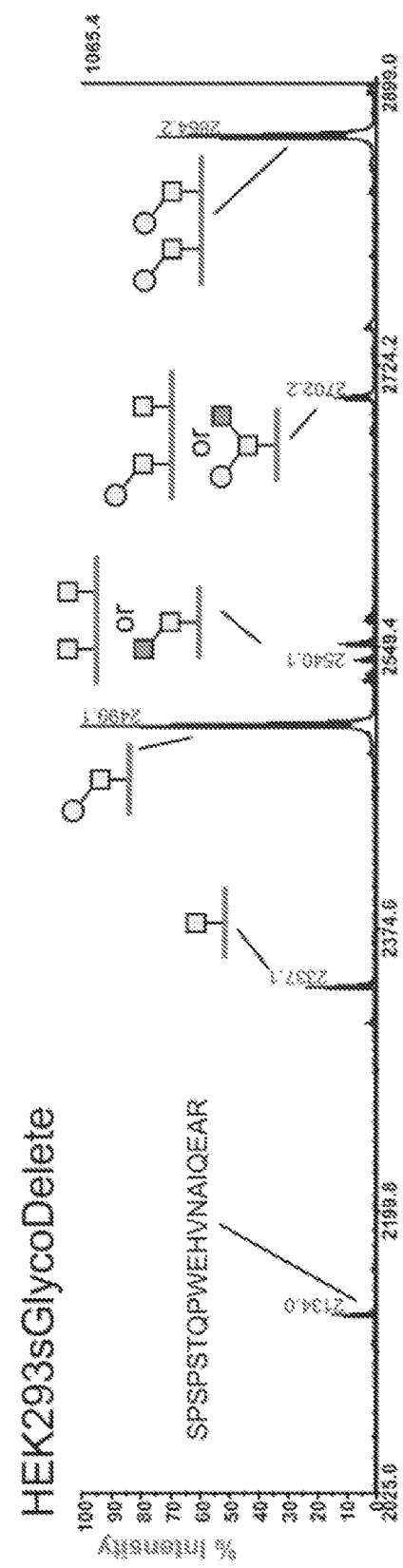
Figure 8B:
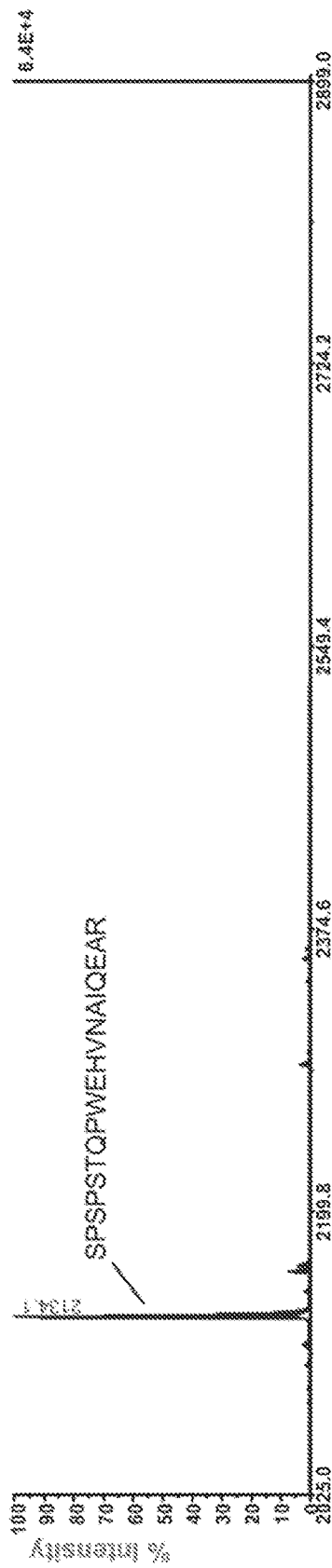
Figure 8B:
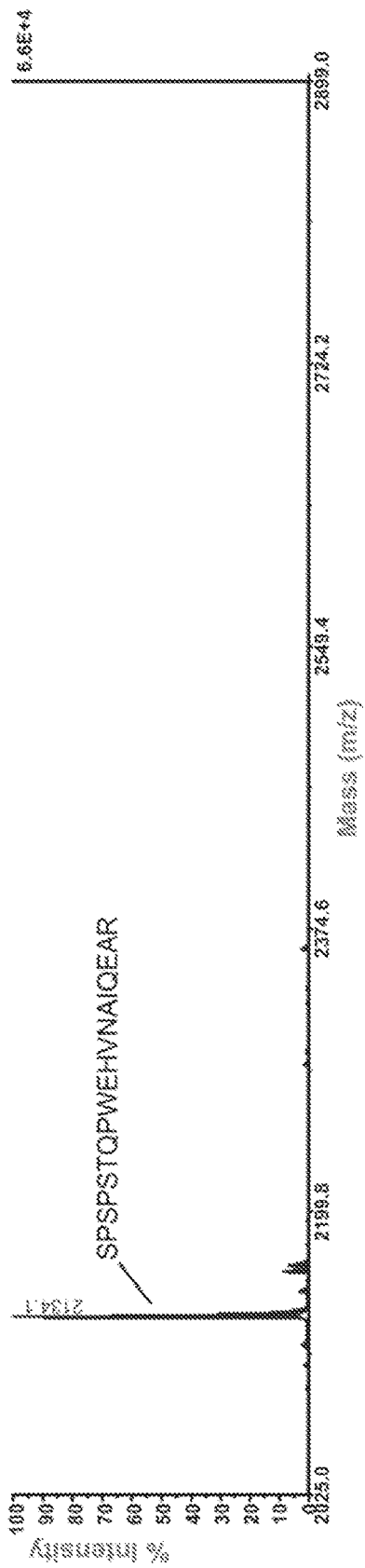

We finally selected one clone (3:1H6) for its fast growth and high yields in protein expression.
HEK293sGlycoDoubleDelete In order to generate a HEK293sGlycoDoubleDelete cell line, HEK293sGlycoDelete cells were transfected with the same CRISPR/Cas9 constructs for the generation of HEK293sGalE$^{-/-}$ cells. Single cells were sorted 72 hours after transfection. Eighteen clones started to grow and were expanded to a 24-well plate. We transfected them with an hGM-CSF expression plasmid and checked the glycoprofile on Western blot in the same way as described above. As can be seen in FIG. 7, hGM-CSF expressed in most of those clones showed a drastically reduced molecular weight, indicating a loss-of-function GalE mutation. We could distinguish three different types of hGM-CSF processing, depending on GalE functionality and clonal differences in endoT processing. In the first type (labeled with N in FIG. 7), smearing due to O-glycosylation is still visible, and consequently the cells still possessed at least one functional GalE gene copy. The second hGM-CSF sample type (labeled B in FIG. 7) originates from cells with a successful GalE knock out, but with reduced or lacking endoT activity (although endoT was active in the parent cells). Consequently, these cells produce hGM-CSF of significantly lower molecular weight, but N-glycoforms with one and two N-glycosylation sites are still detectable. Finally, we observe a third type of hGM-CSF processing, labeled with A in FIG. 7, in which almost no residual glycan heterogeneity is observed. We further call these cells HEK293 sGlycoDoubleDelete.

To further characterize HEK293sGlycoDoubleDelete cells, we selected the clone indicated with a star in FIG. 7 based on successful GalE knock out, proper endoT processing of the N-glycans of hGM-CSF, fast cell growth and high recombinant protein expression levels.

MALDI-TOF Glycan Characterization

To further characterize both new cell lines, hGM-CSF produced in the selected HEK293sGalE$^{-/-}$ and HEK293sGlycoDoubleDelete clonal cell lines was purified. Tryptic peptides of these hGM-CSF samples were analyzed on a MALDI-TOF mass spectrometer to confirm that a GalE KO results in an abrogation of O-glycosylation.

hGM-CSF has four possible O-glycosylation sites, all located on the same tryptic peptide (SPSP STQPWEHVNAIQEAR (SEQ ID NO:3), target Thr and Ser residues underlined) (K. Kaushansky, J. A. Lopez, and C. B. Brown. Role of carbohydrate modification in the production and secretion of human granulocyte macrophage colony-stimulating factor in genetically engineered and normal mesenchymal cells. *Biochemistry* (Mosc.) 31:1881-1886 (1992)). As displayed in the spectrum in FIG. 8, both HEK293s and HEK293sGlycoDelete cells decorate this peptide with several types of O-glycans. We could only detect glycopeptides with no, one or two O-glycosylation sites occupied. This does however not exclude modification of more sites, because peptides carrying more than two O-glycans have increased heterogeneity, which possibly smears the signal out under the detection limit. In addition these glycopeptides potentially do not ionize well anymore. In the spectra of hGM-CSF produced in HEK293sGalE−/− and HEK293sGlycoDoubleDelete cells none of these O-linked glycoforms were detected, confirming the absence of O-glycans in GalE$^{-/-}$ cells. We conclude that no signs of residual GalE activity can be observed in the HEK293sGalE$^{-/-}$ cell line and we thus successfully generated a full GalE knock out. Remarkably, no galactose or GalNAc scavenged from the culture medium ends up in the glycans.

Figure 9:
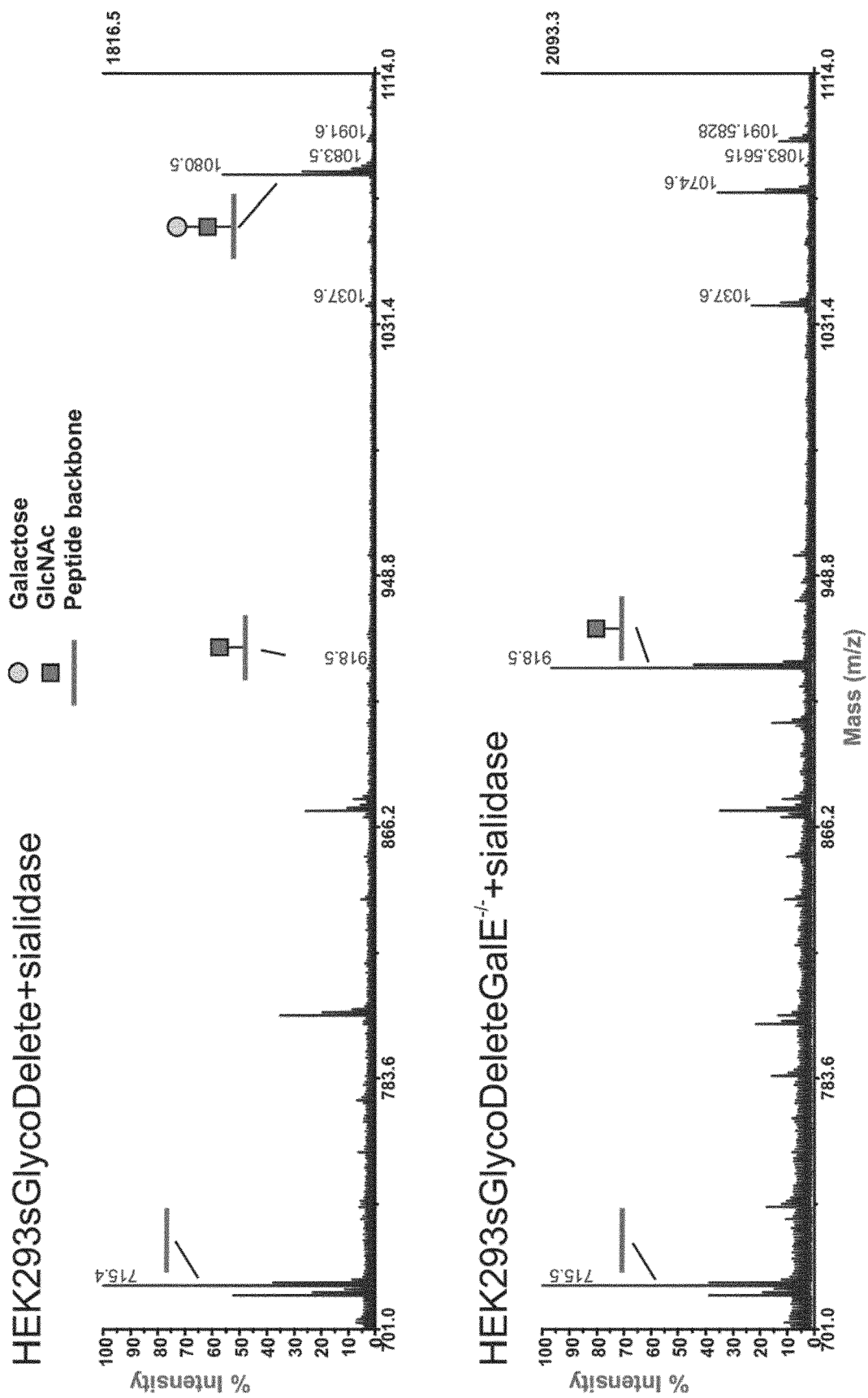
FIG. 9: MALDI-TOF spectrum of sialidase treated LLNLSR (SEQ ID NO:4) peptide from hGM-CSF expressed in HEK293sGlycoDelete and HEK293sGlycoDoubleDelete cells. The unglycosylated peptide has a molecular weight of 715 Da, the Asn-GlcNAc decorated peptide 918 Da and the Asn-GlcNAc-Gal glycopeptide 1080 Da.
Figure 10:
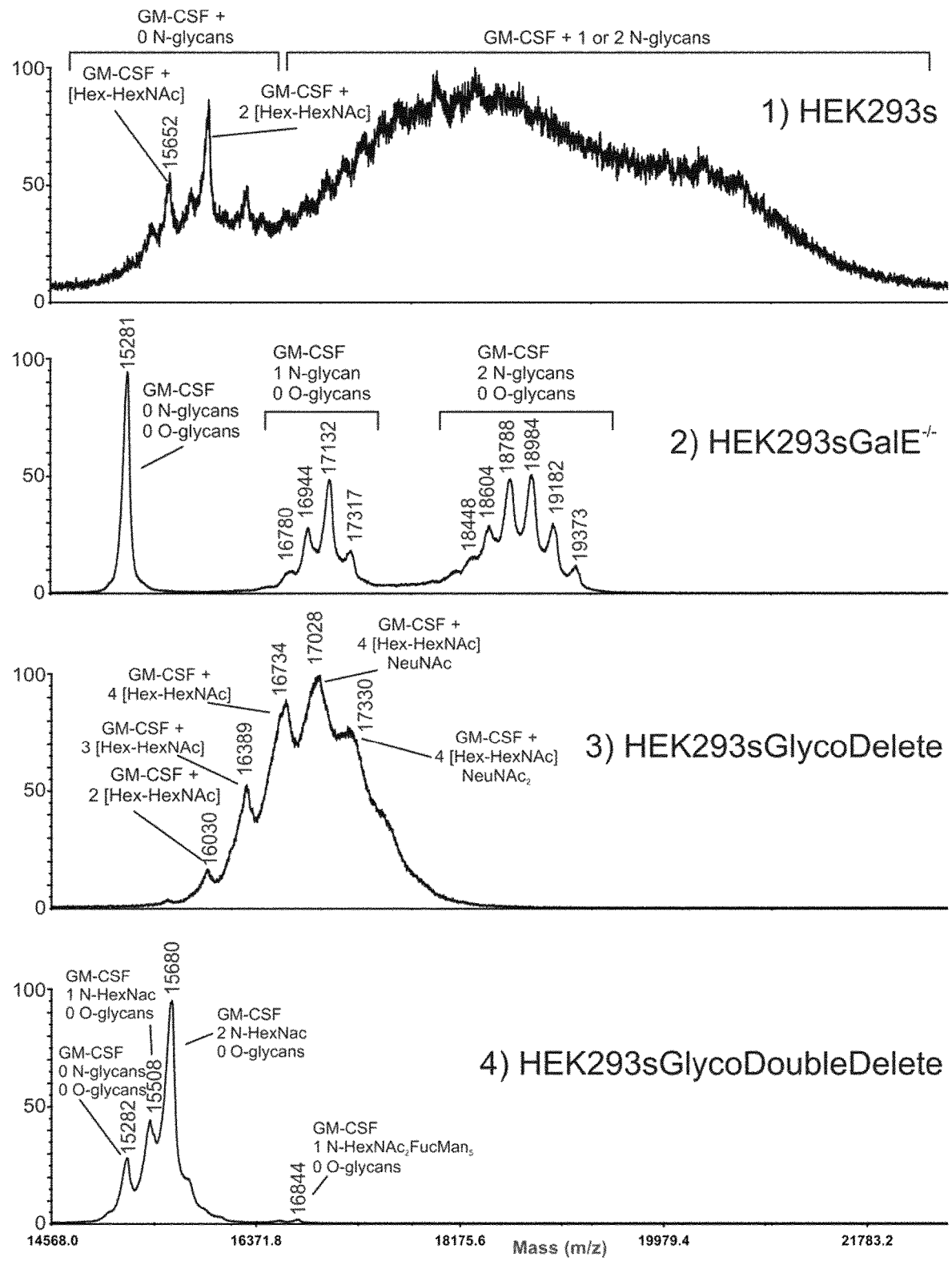
FIG. 10: MALDI-TOF spectrum of different glycoforms of intact hGM-CSF. HEK293 s-produced hGM-CSF smears out through the spectrum due to heterogeneous N- and 0-glycosylation (top spectrum). HEK293sGalE$^{-/-}$ hGM-CSF (second spectrum) lacks O-glycosylation and only shows heterogeneity due to N-glycans, HEK293sGlycoDelete hGM-CSF (third spectrum) shows a reduced N-glycan heterogeneity, but still smears out due to heterogeneous O-glycans. In the last spectrum, the signal of HEK293sGlycoDoubleDelete hGM-CSF is concentrated in three peaks corresponding with hGM-CSF carrying no, one and two GlcNAcs on the two putative N-glycosylation sites. At a m/z of 16844 Da a small peak is observed, corresponding with the molecular weight of hGM-CSF decorated with an oligomannose N-glycan.
Figure 11:
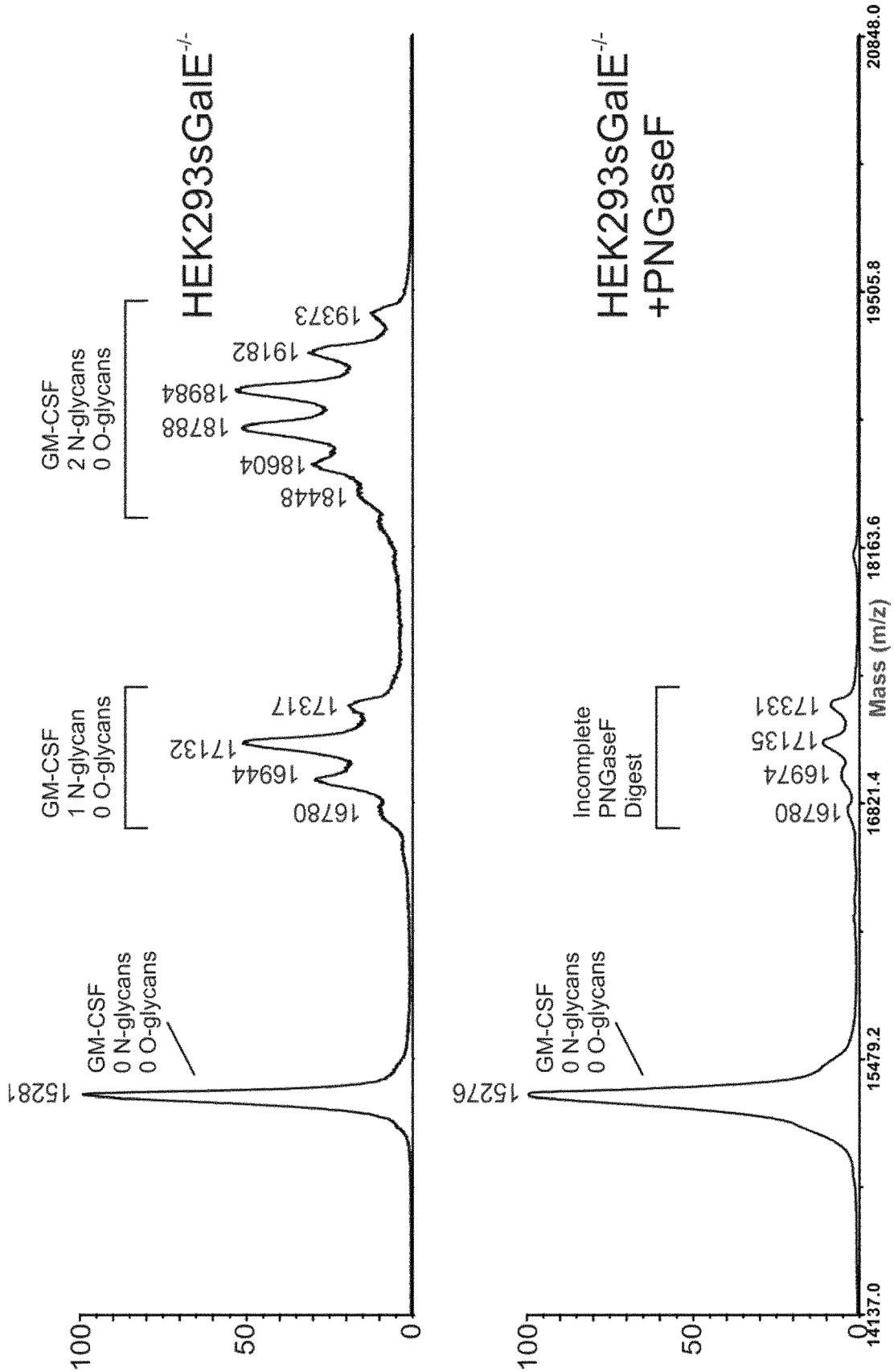
FIG. 11: MALDI-TOF spectrum of intact hGM-CSF produced in HEK293sGalE$^{-/-}$ cells (top spectrum). PNGaseF treatment of the sample resulted in an incomplete removal of the N-glycans (bottom spectrum).
Figure 12:
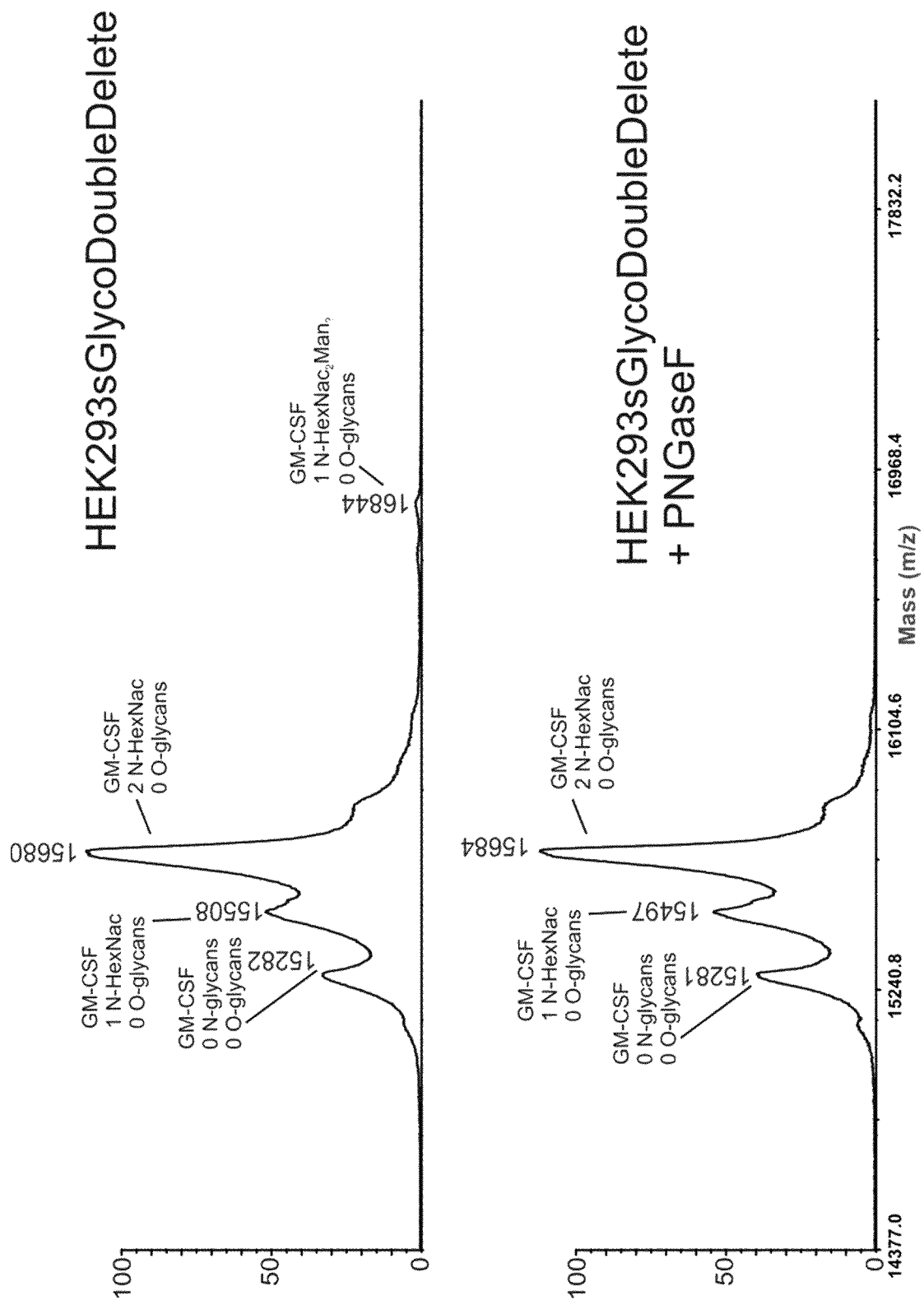
FIG. 12: MALDI-TOF spectrum of intact hGM-CSF produced in HEK293sGlycoDoubleDelete cells (top spectrum). Upon treatment with PNGaseF, the peak with a m/z of 16844 was completely digested.

On hGM-CSF produced in HEK293sGlycoDoubleDelete cells, no galactosylation was detected on the N-linked glycans as depicted in FIG. 9. This observation confirms that the homogeneity of the N-glycans in the HEK293sGlycoDoubleDelete cell line is further enhanced as compared to the parental HEK293sGlycoDelete line. Importantly, no glycopeptides carrying the unprocessed Asn-GlcNAc$_2$-Man$_5$ glycan were detected (data not shown). This would be indicative of incomplete endoT processing, as was observed in some of the initial clones (see lanes indicated with B in FIG. 7). In conclusion, no signs of residual GalE activity can be observed when expressing the hGM-CSF protein in the HEK293sGalE$^{-/-}$ and HEK293sGlycoDoubleDelete cell lines. In addition, we analyzed intact hGM-CSF on a MALDI-TOF mass spectrometer. HEK293s and HEK293sGlycoDelete hGM-CSF were compared to hGM-CSF produced in HEK293sGalE$^{-/-}$ and HEK293sGlycoDoubleDelete cells (FIG. 10). The first lane depicts the spectrum of HEK293s hGM-CSF. The heterogeneous N- and O-linked glycoforms spread out in a broad heterogeneous signal. Lane two of FIG. 10 depicts hGM-CSF produced in HEK293sGalE$^{-/-}$ cells. In this spectrum, we could detect a fully aglycosylated peak and two smaller smears at higher molecular weight. Upon PNGaseF treatment, the major fraction of these two small smears was digested (FIG. 11). This digest, although incomplete, confirms that the remainder heterogeneity in HEK293sGalE$^{-/-}$ cells originated from N-glycosylation. When addressing this N-glycosylation heterogeneity through GlycoDelete, the three possible GlycoDelete N-glycan stumps could be detected, but their signal still smeared out through the spectrum due to O-glycan heterogeneity (FIG. 10, lane 3). Upon combination of the GalE KO in HEK293sGlycoDelete cells, both O- and N-linked glycan heterogeneity was significantly reduced, as illustrated in the last lane of FIG. 10, depicting HEK293sGlycoDoubleDelete hGM-CSF. Here, only hGM-CSF decorated with no, one or two GlcNAc residues could be detected. Consequently the remainder heterogeneity detected in the spectrum originated from differential N-glycan site occupancy. At a m/z of 16844 Da, a small peak is detected, corresponding with the molecular weight of hGM-CSF decorated with an oligomannose N-glycan. A PNGaseF digest confirms that this peak is an N-glycan (FIG. 12).

Figure 14A:
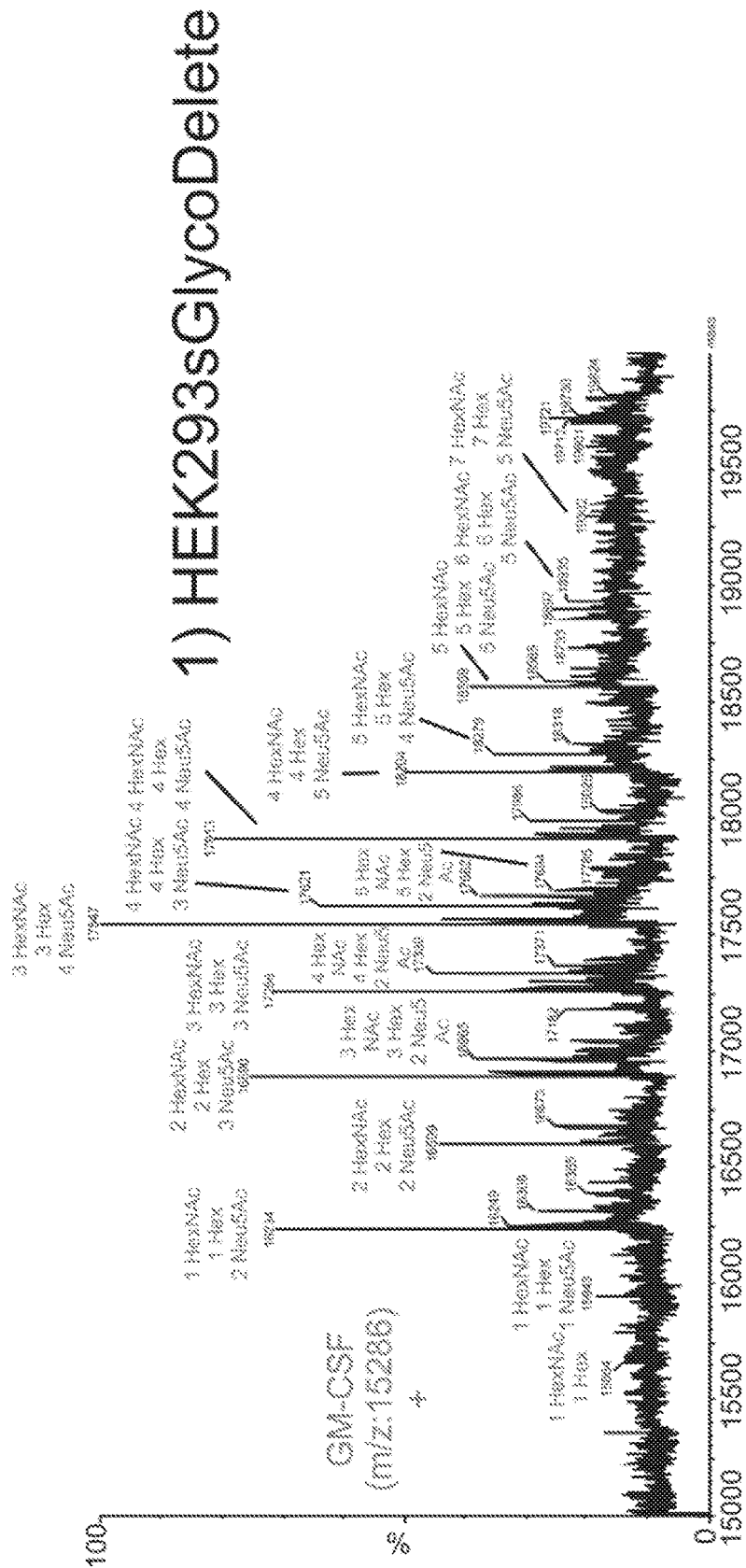
FIGS. 14A-14C: QTOF MS analysis of intact hGM-CSF produced in HEK293sGlycoDelete, HEK293sGalE and HEK293sGlycoDoubleDelete. The spectra are in line with the data observed in FIG. 10.
Figure 14B:
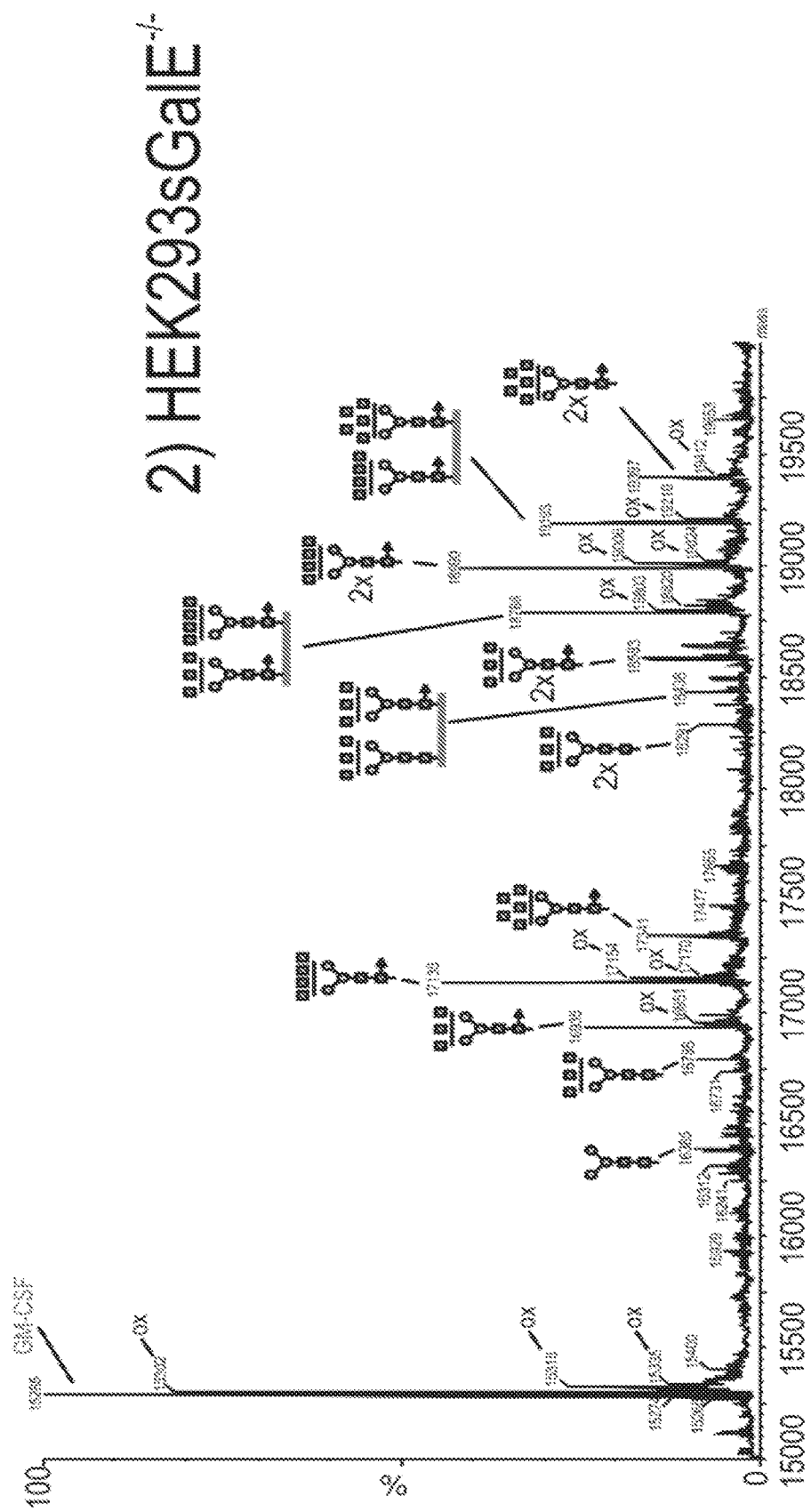
Figure 14C:
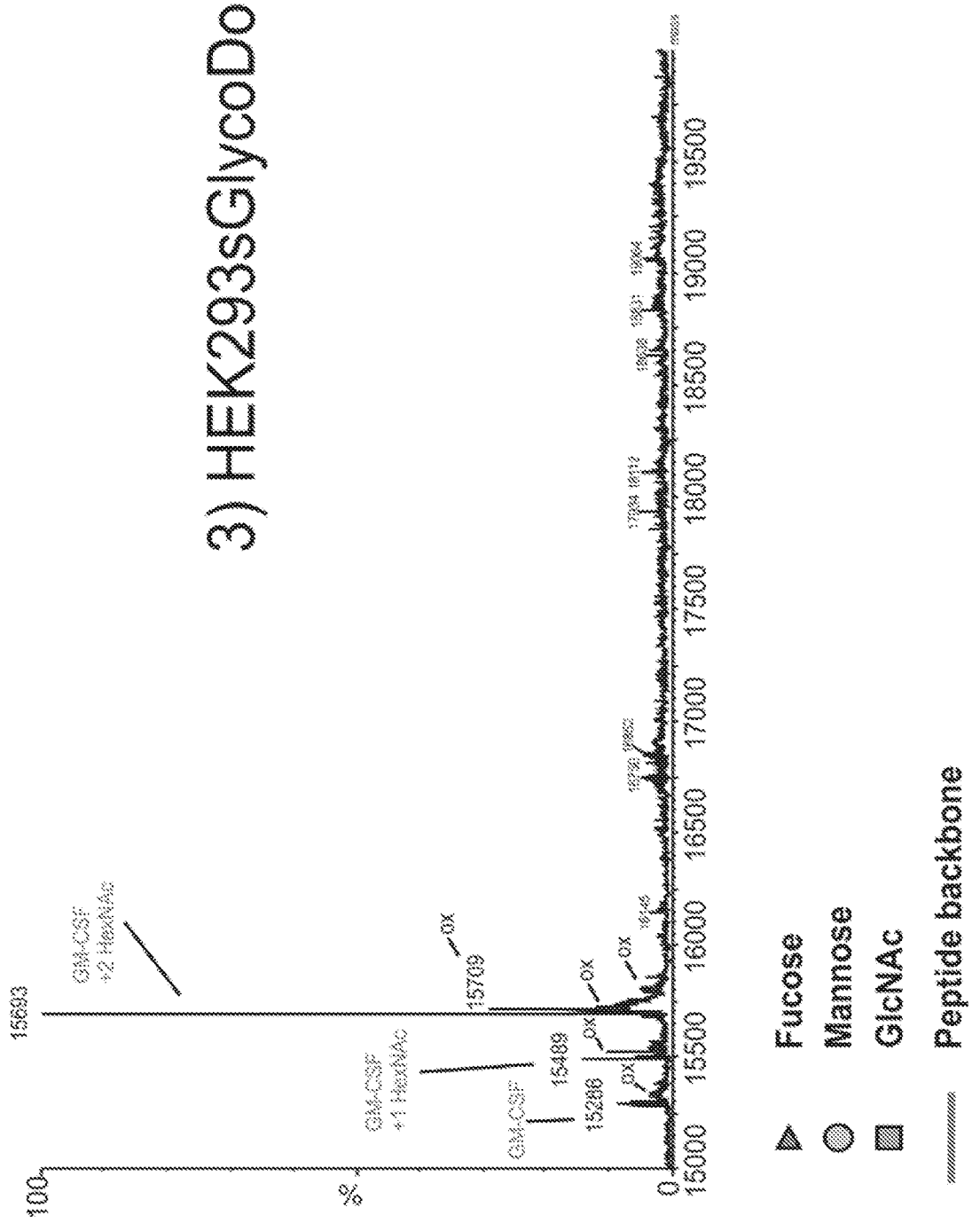

The intact hGM-CSF was also analyzed on a qtof MS for higher resolution (FIG. 14). This confirmed the previous results with higher detail. We were unable to obtain a spectrum for HEK293s produced hGM-CSF as this was too complex to deconvolute.

We conclude that again no O-glycans were detected in both GalE KO cell lines. HEK293sGlycoDoubleDelete cells have a very homogeneous glycoprofile, with no heterogeneity except three peaks originating from the different site-occupancy of the two hGM-CSF N-glycosylation sites, which are only decorated with a single GlcNAc.

Discussion

HEK293sGlycoDelete cells tackle heterogeneity in N-glycosylation. However, protein glycosylation mainly comes in two types: O-linked and N-linked carbohydrates. When aiming to produce completely homogeneous glycoproteins, O-glycosylation is the most important remaining source of heterogeneity in GlycoDelete-produced proteins. By knocking out the GalE gene, which epimerizes UDP-GlcNAc to UDP-GalNAc, we deprived HEK293s cells of UDP-GalNAc and consequently prevented any mucin type O-glycosylation on the proteins. The alternative salvage pathways appeared not to be active or did not manage to scavenge the necessary precursors, because no galactose or GalNAc decorated residues were detected. Galactose and GalNAc concentration in the medium used during hGM-CSF expression (FreeStyle 293 Expression Medium) are not disclosed, so we are unable to allocate the lack of salvaged nucleotide sugars to their absence in the medium or to inactive or disrupted salvage pathways in the cells. By combining the GalE KO strategy with HEK293sGlycoDelete cells, we generated HEK293sGlycoDoubleDelete cells. These cells are able to express proteins with essential and complex PTMs but without the inherent heterogeneity caused by these PTMs. The predicted glycoforms in both HEK293sGalE$^{-/-}$ and HEK293sGlycoDoubleDelete cells could be confirmed by mass spectrometry.

With these two new cell lines, we can now selectively choose to produce proteins in wild type HEK293s cells, HEK293s cells with reduced N-glycosylation, HEK293s cells with no O-glycosylation or HEK293s cells with no O-glycosylation and reduced N-glycosylation. An overview of the different possible cell lines with the impact on (hGM-CSF) glycan heterogeneity is provided in FIG. 13.

Through generating a GalE KO we optimized a protocol that allows high throughput screening of clones for genome editing. The phenotypic hGM-CSF expression screen was very valuable, but has an applicability limited to glycan engineering. In general, phenotypic screens for generating new cell lines through genome engineering all have the same drawback: they lack a positive control since it is the first time such a cell line is generated. As illustrated multiple times in the addendum "The road to nowhere," it can be difficult to assess whether the phenotypic screen is not working or whether there are just no correct clones. Therefore, easily applicable large throughput genomic screens are essential.

In contrast to phenotypical screening, the protocol used for genomic screening is easily adaptable to other targets. Initially our genomic screening method was very tedious and labor intensive. Moreover, the potential correct clones were growing in the meantime, resulting in additional work to maintain the cells or make freezings. With the protocol optimized in this work, we are now able to screen a few hundred clones within a day. To illustrate the potential, we performed a larger screen in which we aimed for a homologous recombination knock in event with Cas9n guides. By combining the genotypic screen with smart pooling of the samples, we screened 125 clones to find two cell lines carrying the knock in construct (L. A. Tabak, The role of mucin-type O-glycans in eukaryotic development. *Semin. Cell Dev. Biol.* 21:616-621 (2010)). Especially in combination with the Illumina sample preparation developed in this section, screening of hundreds of clones becomes possible within a few days. Hereby one also avoids additional handling of the potential clones to maintain them, as the screen can be finished before the cells grow to full confluency.

Importantly, 293s GalE KO cells have been kept in culture for over 15 passages and no major growth defect was detected. Also expression levels did not seem to be radically reduced. The GlycoDelete GalE KO's have been kept in culture for >5 passages and also there no major growth defect was detected. Also here expression levels were not drastically reduced compared to WT HEK cells.

Example 4. Expression of hEPO-His6

To underline the previously presented findings, His6-tagged human EPO was stably expressed in adherent HEK293s, HEK293sGlycoDelete, HEK293sGale-/- and HEK293sGlycoDoubleDelete cells.

HEK239s, HEK239sGalE-/-, HEK239sGlycoDelete, and HEK239GlycoDoubleDelete cells were seeded in 6-well plates, in DMEM/F12 medium+10% FCS. At 24 hours post seeding, the medium was aspirated and replaced with 3 ml serum-free FreeStyle 293 medium, and cells were mock-transfected or transfected with an expression vector encoding hEPO (FuGENE HD; manufacturer's instructions were followed). Supernatants were collected at 5 days post transfection.

Figure 15:
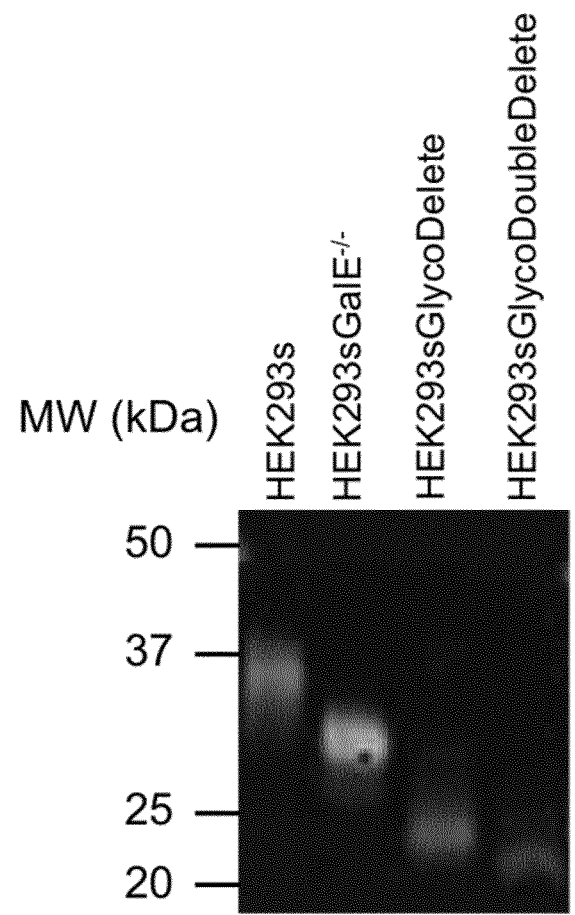
FIG. 15: SDS-PAGE and His-tag-specific Western Blot analysis of hEPO-His6, stably expressed in HEK293s (lane 1), HEK293sGalE–/– (lane 2), HEK293sGlycoDelete (lane 3), and HEK293sGlycoDoubleDelete (lane 4) cells. A clear shift in molecular weight can be observed. This corresponds with the reduced N-glycans in HEK293sGlycoDelete and HEK293sGlycoDoubleDelete cells and the absent O-glycans in HEK293sGalE–/– and HEK293sGlycoDoubleDelete cells.

Supernatant samples were analyzed via SDS-PAGE and Western Blot analysis (FIG. 15). hEPO-His6 was stably expressed in HEK293s (lane 1), HEK293sGalE$^{-/-}$ (lane 2), HEK293sGlycoDelete (lane 3), and HEK293sGlycoDoubleDelete (lane 4) cells. A clear shift in molecular weight can be observed. This corresponds with the reduced N-glycans in HEK293sGlycoDelete and HEK293sGlycoDoubleDelete cells and the absent O-glycans in HEK293 sGalE$^{-/-}$ and HEK293 sGlycoDoubleDelete cells.

Tryptic peptides of the purified hEPO-His6 were analyzed on a ESI-LC-MS mass spectrometer.

Figure 16:
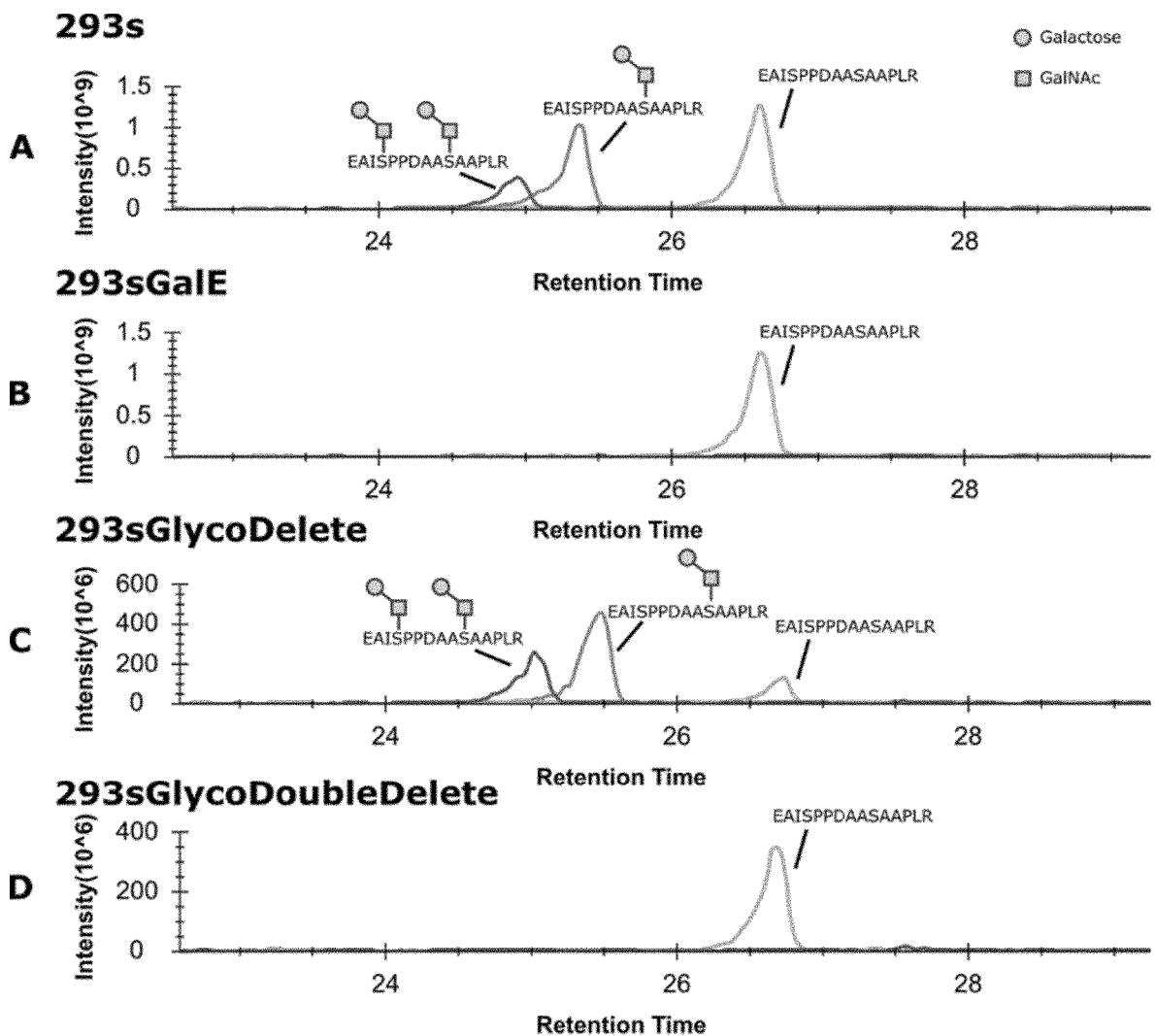
FIG. 16: MS1 spectrum of trypsinized hEPO-His6 analyzed by ESI-LC-MS mass spectrometry. The tryptic peptide EAISPPDAASAAPLR (SEQ ID NO:5) contains two possible O-glycosylation sites. On the tryptic peptide derived from hEPO-produced HEK293s and HEK293sGlycoDelete cells, both sites were indeed occupied by O-glycans. In hEPO-His6 produced in HEK293sGalE–/– and HEK293sGlycoDoubleDelete cells, only the naked peptide is detected.

Mass spec data identify the tryptic peptide EAISPP-DAASAAPLR (SEQ ID NO:5) as a target site for mucin-type O-linked glycosylation (target Ser residues underlined, FIG. 16). HEK293s and HEK293sGlycoDelete cells can decorate this peptide with O-glycans. Peptides with no, one or two occupied O-glycosylation sites were detected. In the spectra of hEPO-His6 produced in HEK293sGalE-/- and HEK293sGlycoDoubleDelete cells, none of the O-linked glycoforms were detected, confirming the absence of mucin-type O-glycans in GalE-/- cells.

Example 5. Expression of Etanercept

As a proof of concept, Etanercept (Enbrel), which consists of a fusion between an Fc tail and the human TNF receptor 2 and which contains multiple O- and N-glycosylation sites, was expressed in HEK293s, HEK293sGlycoDelete, HEK293sGale-/- and HEK293sGlycoDoubleDelete cells.

Every cell line was seeded in 6-well plates, in DMEM/F12 medium+10% FCS. At 24 hours post-seeding, the medium was aspirated and replaced with 3 ml serum-free FreeStyle 293 medium, and cells were mock-transfected or transfected with an expression vector encoding Etanercept (Enbrel) (FuGENE HD; manufacturer's instructions were followed). Supernatants were collected at 5 days post-transfection.

Figure 17:
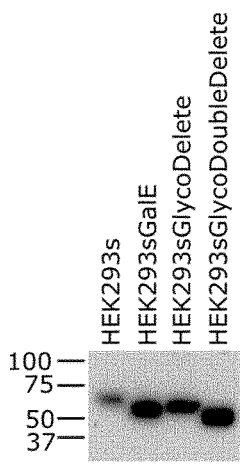
FIG. 17: Western Blot analysis of etanercept, stably expressed in HEK293s (lane 1), HEK293sGalE–/– (lane 2), HEK293sGlycoDelete (lane 3), and HEK293sGlycoDoubleDelete (lane 4) cells. A clear shift in molecular weight can be observed.

Supernatant samples were analyzed via SDS-PAGE and Western Blot analysis (FIG. 17) and it was shown that etanercept was stably expressed in HEK293s (lane 1), HEK293 sGalE-/- (lane 2), HEK293 sGlycoDelete (lane 3), and HEK293 sGlycoDoubleDelete (lane 4) cells. A clear shift in molecular weight can be observed corresponding with the reduced N-glycans in HEK293sGlycoDelete and HEK293sGlycoDoubleDelete cells and the absent O-glycans in HEK293 sGalE-/- and HEK293 sGlycoDoubleDelete cells.

The reduction in molecular weight between HEK293 S and HEK293 SGalE-/- on one hand and HEK293SGlycoDelete and HEK293 SGlycoDoubleDelete on the other hand indicates that Etanercept produced in Gale KO cells is indeed devoid of O-glycans. The molecular weight difference between HEK293 S and HEK293 SGlycoDelete cells agrees with the expected difference between wild type N-glycans and GlycoDelete N-glycans.

Example 6. Expression of RSV-G (Respiratory Syncytial Virus—G Protein)

As another example, RSV-G was expressed in the different cell lines. In detail, HEK239s, HEK239sGalE-/-, HEK239sGlycoDelete, and HEK239GlycoDoubleDelete cells were seeded in 6-well plates, in DMEM/F12 medium+10% FCS. At 24 hours post-seeding, the medium was aspirated and replaced with 3 ml serum-free FreeStyle 293 medium, and cells were mock-transfected or transfected with an expression vector encoding RSV-G (FuGENE HD; manufacturer's instructions were followed). Supernatants were collected at 3 days post-transfection.

Supernatant samples were analyzed via SDS-PAGE and Western Blot analysis (FIG. 18) and it was shown that RSV-G could be expressed in HEK293s, HEK293sGalE-/-, HEK293 sGlycoDelete, and HEK293 sGlycoDoubleDelete cells. In HEK293sGlycoDoubleDelete cells, one clear band without any smear was observed.

Materials and Methods

Guide Assembly and Cloning

The GalE gene was downloaded from the UCSC human genome browser (build nr. GRCh37/hg19) and screened for guides using the tool available at http://CRISPR.MIT.EDU. We selected three guides with the best off-target scores according to the website's algorithm. Oligos coding for the guide and its reverse complement were extended with ends compatible with our cloning strategy, 5' phosphorylation and ordered at IDT. The sequences of the final guide sequences are displayed in Table 5. Next, the three guides were cloned into the PX458 vector (available through Addgene) as described in Ran et al [10]. Briefly, the oligos were annealed by adding 1 μl of a 100 μM dilution of each oligo to 8 μl duplexing buffer (100 mM Potassium Acetate, 30 mM HEPES, pH 7.5). This mix was heated to 98° C. and gradually cooled down to 25° C. at 5° C./minute 2 μl of a 1/200 dilution of the annealed oligos were added to 100 ng of the PC458 vector, 2 μl Tango buffer (Fermentas, Thermo Fisher Scientific, Waltham, Mass.), 1 μl of DTT (10 mM), 1 μl of ATP (10 mM), 1 μl BbSI FastDigest restriction enzyme (Fermentas), 1 μl T7 ligase (Fermentas) and milliQ to a total volume of 20 μl. By cycling this mix six times from 5 minutes at 37° C. to 5 minutes at 25° C., the restriction and ligation were incubated. Next 2 μl of the product was transformed to chemically competent MC1061 *E. coli* cells. The cells were grown at 37° C. overnight in LB medium containing carbenicillin antibiotic, to select for cells containing the PX485 vector.

TABLE 5

Assembly of the ordered oligos used to clone the guides in the PX458 vector

| Guide | 5' end | Guide sequence | 3' end | SEQ ID NO: |
|---|---|---|---|---|
| Guide 1 | CACCg | TGGAAGTTATCGATGACCAC | | 6 |
| | AAAC | GTGGTCATCGATAACTTCCA | c | 7 |
| Guide 2 | CACCg | CTTTTTGAAGAGACGCTGTA | | 8 |
| | AAAC | TACAGCGTCTCTTCAAAAAG | c | 9 |
| Guide 3 | CACCg | CTTCTGCACCGACTCGCCCA | | 10 |
| | AAAC | TGGGCGAGTCGGTGCAGAAG | c | 11 |

We verified the obtained *E. Coli* clones in a colony PCR using a forward primer on the U6 promotor (AGCCTATG-GAAAAACGCCAGCAACGC (SEQ ID NO:12)) and as reverse primer the bottom oligo of the guide. We used GoTaq Green (Promega, Madison, Wis., USA) according to the manufacturer's instructions with an annealing temperature of 58° C. and an elongation time of 1 minute. The PCR samples were analyzed MCE-202 MultiNA Microchip Electrophoresis System (Shimadzu, Kyoto, Japan).

Table 6 and gDNA template isolated with QuickExtract at an annealing temperature of 55° C. and an elongation time of 2 minutes. The amplicon was purified using magnetic beads (PCR Clean Up, CleanNA, Alphen aan den Rijn, Netherlands), according to the manufacturer's instructions.

To produce the guide RNAs in vitro, we had to introduce a T7 promoter. We thus used primers coding for a T7 promotor 5' of the guide. The T7 promotor, preceding the forward primer is indicated in bold in to the transcription reaction.

Table 6. The reverse primer binds to the structural part of the guide (Guide rev), this primer designed strategy has been described earlier (Yang, Z. et al. The GalNAc-type O-glycoproteome of CHO cells characterized by the SimpleCell strategy. *Mol. Cell. Proteomics* mcp.M114.041541 (2014)). For the amplification with these primers, GoTaq Green polymerase (Promega, Madison, Wis., USA) was used following the manufacturer's instructions, with an annealing temperature of 58° C. and an elongation time of 30 seconds. 10 ng of the relevant PX458 plasmid with the respective guide cloned into the multi cloning site was used as a template. To transcribe RNA from these PCR reaction mixtures, a Megascript T7 kit (Ambion, Life technologies, Paisley, UK) was used according to the manufacturer's instructions: first the PCR amplicon was purified with magnetic beads (PCR Clean Up, CleanNA, Alphen aan den Rijn, Netherlands) and 2 pmol DNA was supplied to the transcription reaction.

TABLE 6

Primers used for the in vitro CRISPR/Cas9 test. Sequences in bolt are the T7 promotor.

| Primer name | Sequence | SEQ ID NO: |
|---|---|---|
| GalE forward | GTGTAGTGGCCTGATTTGGCTCAC | 13 |
| GalE reverse | GTGGGAAGGAAGCTCTGAGCAG | 14 |
| T7 Guide1 Fw | TAATACGACTCACTATAGGGTGGAAGTTATCGATGACCAC | 15 |
| T7 Guide2 Fw | TAATACGACTCACTATAGGGCTTTTTGAAGAGACGCTGTA | 16 |
| T7 Guide 3 Fw | TAATACGACTCACTATAGGGCTTCTGCACCGACTCGCCCA | 17 |
| Guide rev | AAAAGCACCGACTCGGTGCC | 18 |

Genomic DNA Prep

For genomic DNA (gDNA) isolation from all HEK cell lines, $2*10^5$ cells were lysed in 100 μl of QuickExtract DNA Extraction Solution (Epicentre, Madison, Wis., USA) according to the manufacturer's instructions. The QuickExtract genomic DNA extraction does not include a DNA purification step. Therefore the extract contains high amounts of residual cellular lysate products, making it difficult to measure the genomic DNA concentration in the sample. Therefore we always started with an equal amount of cells to prepare genomic DNA in an equal amount of QuickExtract DNA extraction solution, and for every PCR on gDNA described in this section we used 1 μl of this lysate per 10 μl of total PCR volume.

In Vitro Digests with Cas9.

The region of interest of the target (GalE gene) was amplified using GoTaq Green (Promega, Madison, Wis., USA), the GalE forward and reverse primers displayed in to the transcription reaction.

The in vitro transcribed RNA was purified using phenol/chloroform extraction. First an equal volume of acidic phenol/chloroform (Ambion, Life technologies, Paisley, UK) was added to separate the organic phase from the upper aqueous phase. The upper phase was transferred to a new tube, in which the RNA was precipitated by adding 1 volume of isopropanol. The mixture was incubated for 15 minutes at −20° C., upon which the RNA was pelleted in a cooled table top centrifuge at 15,000 rpm. The supernatant was removed and the pellet resuspended in nuclease free water. The RNA solution was quantified by nanodrop.

Finally, 2 μg of guide RNA was added to 1 μM of Cas9 (NEB, Ipswich, Mass., USA) in 20 μl of nuclease free water and 3 μl of 10×Cas9 nuclease reaction buffer. We allowed the Cas9 to bind the guide RNA for 10 minutes at 37° C. Finally 500 ng of template DNA was added and incubated with the RNA and Cas9 at 37° C. for 1 hour. Digestion of the template DNA by the Cas9 and guide RNA complex was analyzed by separating the reaction mixture on a 1.2% TAE-agarose gel.

Cultivating, Transfecting and Sorting Cell Lines

HEK293s and HEK293sGlycoDelete cells were maintained in a humidified incubator at 37° C. and 5% $CO_2$ in DMEM/F12 (Life Technologies, Paisley, UK) supplemented with 10% fetal calf serum (FCS).

To transfect HEK293s or HEK293sGlycoDelete cells for small scale productions or genome editing experiments, they were seeded 48 hours prior to transfections at approximately 200,000 cells per well in a 6-well or 500,000 cells in a T25. Fugene HD transfection reagents (Promega, Madison, Wis., USA) was used to transfect 3.3 µg plasmid DNA per well according to the manufacturer's instructions.

To detect expression of fluorescent proteins, the cells were detached 48 hours post-transfection by pipetting the medium up and down. The medium containing the cells was pelleted down for 4 minutes at 400 RPM and resuspended in PBS at $1*10^6$ cells/ml. Multicellular clusters were filtered out by applying the suspension on a 100 m cell strainer (Corning, Midland, Mich., USA). Next the cells were sorted on a BD FACS ARIA III, by selecting for GFP positive single cells. Positive cells were directly single cell sorted into a 96-well plate, seeding out 1 cell per well or pooled in a tube. In the wells a 1:1 (v/v) mix of fresh DMEM/F12+10% FCS and conditioned medium was added. Conditioned medium was prepared by seeding out $1*10^6$ HEK293sGlycoDelete cells in 10 ml DMEM/F12+10% FCS, then grow the cells for three days and finally harvest the medium by filtering through a 0.22 m filter (Millipore, Billerica, Mass., USA).

hGM-CSF Production Purification hGM-CSF was produced, purified and prepared for mass spec analysis as described earlier.[1] Briefly, the cells were transfected with an hGM-CSF expression plasmid. One day post transfection the medium was exchanged to Freestyle 293 Expression medium (Life technologies, Paisley, UK) and the supernatant was harvested 5 days post transfection. The medium was directly loaded on a His-Trap HP column loaded with $Ni^{2+}$ ions (GE healthcare UK Ltd, Buckinghamshire, UK) on an Äkta Pure (GE healthcare UK Ltd, Buckinghamshire, UK), followed by a polishing step on a superdex 75 size exclusion column (GE healthcare UK Ltd, Buckinghamshire, UK) to change the buffer to PBS. The protein concentration after purification was determined by Pierce BCA Protein Assay Kit (Life technologies, Paisley, UK).

hGM-CSF Peptide Maldi-Tof Ms Analysis

For MALDI-TOF analysis, 2.5 µg of hGM-CSF sample was separated on an SDS-PAGE gel, the region from 20 to 70 kDa was cut out of the gel and an in-gel tryptic digest was performed. Peptide extraction and cleanup was performed using C18 ZipTips (Merck Millipore, Billerica, Mass., USA), eluting the samples in a total volume of 5 µl. Next, 2 µl of each peptide mix was spotted on a MALDI target plate in CHCA (α-cyano-4-hydroxycinnamic acid) matrix. MALDI-TOF analysis was performed in the positive ion mode with the reflectron activated for optimal resolution.

hGM-CSF Intact Protein Maldi-Tof Ms

Five g of hGM-CSF in PBS was aliquoted in separate tubes. Either no enzyme 500 units PNGaseF (homemade) was added and the samples incubated for 24 hours at 37° C. After digestion, 0.1% TFA was added and the samples were desalted using C4 ZipTips™ (Merck Millipore, Billerica, Mass., USA) according to the manufacturer's instructions. Final elution was done in 3 1 of 50% acetonitrile, 49.5% milliQ and 0.5% TFA, which was directly spotted on the MALDI plate. 1 µl of 10 mg/ml alpha-cyano-4-hydroxycinnammic acid matrix was added to each spot. The samples were analyzed on an Applied Biosystems 4800 proteomics analyzer in the linear mode.

Surveyor Assay

In a six-well plate, $1*10^6$ cells were transfected with 8.8 µg of the PX458 vector containing a guide by using Fugene HD (Promega, Madison, Wis., USA) transfection reagents. Seventy-two hours post-transfection, we FACs sorted the GFP expressing clones out of the transfected cells. We pooled the sorted cells and let them expand to approximately $1*10^6$ cells. The cells were harvested by pipetting the medium up and down. Genomic DNA was prepared with the QuickExtract kit (Epicentre, Madison, Wis., USA), according to the manufacturer's instructions.

The region targeted by the CRISPR/Cas9 guide RNAs was PCR amplified using 3 µl of the QuickExtract solution on a total PCR volume of 30 µl as template. We used Kapa HiFi polymerase (Kapa Biosystems, Cape Town, South Africa) and the primers displayed in Table 7. The PCR was preformed according to the manufacturer's instructions and with an annealing temperature of 71° C. and elongation time of 30 seconds.

TABLE 7

Primers used to amplify part of the GalE gene for a Surveyor assay

| Primer | Sequence | SEQ ID NO: |
|---|---|---|
| surveyor GalE1&2 fw | TGATCTCCTCACCTCGGCCT | 19 |
| surveyor GalE1&2 rev | ACACTGCCGCCTCCTTCCAA | 20 |
| surveyor GalE3 fw | TGACCTCTGCCTCACACATTACTCCC | 21 |
| surveyor GalE3 rev | CTGGACAACAGAGCGAGACTGTCAA | 22 |

The amplicon was purified using magnetic beads (CleanNA, Alphen aan den Rijn, Netherlands). Next, 400 ng of purified DNA was diluted in a total volume of 9 µl with milliQ, to which 1 µl of 10× Standard Taq Buffer (NEB, Ipswich, Mass., USA) was added. The fragments were denatured and renatured according to the temperature gradient displayed in Table 8.

TABLE 8

Denaturation and renaturation program for a surveyor assay

| Temp. (° C.) | Time |
|---|---|
| 95 | 10 minutes |
| 95 to 85 | 2° C./second |
| 85 | 1 minute |
| 85 to 75 | 0.30° C./second |
| 75 | 1 minute |
| 75 to 65 | 0.30° C./second |
| 65 | 1 minute |
| 65 to 55 | 0.30° C./second |
| 55 | 1 minute |
| 55 to 45 | 0.30° C./second |
| 45 | 1 minute |
| 45 to 35 | 0.30° C./second |
| 35 | 1 minute |

TABLE 8-continued

Denaturation and renaturation program for a surveyor assay

| Temp. (° C.) | Time |
|---|---|
| 35 to 25 | 0.30° C./second |
| 25 | 1 minute |
| 4 | ∞ |

One µl of Surveyor nuclease and 1 l of Surveyor enhancer (IDT, Leuven, Belgium) were added to the mix and incubated for 1 hour at 42° C. Finally, 1 µl Surveyor stop solution was added and the samples were analyzed by separation on a 1.2% TAE-agarose gel.

Sanger Sequencing

The single cell derived clones were expanded in a 24-well plate, from which genomic DNA was prepared using QuickExtract as detailed before. The region of interest was PCR amplified by Kapa HiFi polymerase and the primers displayed in table 9.

The PCR was preformed according to the manufacturer's instructions with an annealing temperature of 72° C. and an elongation time of 1 minute and 30 seconds.

TABLE 9

Primers used to amplify the CRISPR/Cas9 targeted GalE region for Sanger sequencing

| Primer | sequence | SEQ ID NO: |
|---|---|---|
| Fw | GTGTAGTGGCCTGATTTGGCTCAC | 13 |
| Rev | GTGGGAAGGAAGCTCTGAGCAG | 14 |

The amplicon was purified using magnetic beads (CleanNA, Alphen aan den Rijn, Netherlands) and sequenced using the forward primers from Table 7.

Illumina Sequencing Prep

Illumina sequencing uses specific adapters. However these adaptors are quite long, so we first amplified the region of interest with smaller intermediate adapters, which we then extended in a second reaction with the Illumina sequencing adaptors. So first the region targeted by the CRISPR/Cas9 guides was amplified from gDNA isolated with QuickExtract and at the same time extended with the intermediate adaptors (bold in the first four primers of Table 10) in an initial PCR reaction. In this reaction Kapa HiFi polymerase was used according to the manufacturer's instructions, with an annealing temperature of 70° C. and 72° C. for Guide 3 and Guide 1 primers respectively and an elongation time of 30 seconds. The amplicon was purified using magnetic beads (CleanNA, Alphen aan den Rijn, Netherlands). 100 ng of purified amplificate was again amplified to attach the P5 adaptor and Illumina sequencing forward adapter to one side and the P7 adaptor, Illumina sequencing reverse adaptor and Truseq barcode to the other side (Table 10). By providing every clone with a different Truseq barcode (Table 10, primers named "P7 Truseq13 to 28"), we could trace back which sequence belonged to which clone after the sequencing run. Again Kapa HiFi polymerase was used according to the manufacturer's instructions with an annealing temperature of 70° C. and an elongation time of 30 seconds. However, to avoid amplification bias, only 15 cycles were run.

The samples were purified using magnetic beads (CleanNA, Alphen aan den Rijn, Netherlands) and the concentration was measured on the nanodrop. We pooled the samples at equimolar quantities and diluted the mixture to 10 nM. This sample was pooled with other samples at 1% of the total DNA concentration. This mix was then analyzed on an Illumina NextSeq using single end sequencing.

TABLE 10

Primers used to attach Illumina sequencing primers to the target regions of interest. The first four primers contain a target specific part and part of the Illumina sequencing primer (indicated in bold) as intermediate adapter. In a second PCR this intermediate adapter was used to fuse the full size Illumina adaptors to the amplicon, by using the Universal primer P5 and the different P7 truseq primers. The universal primer P5 contains the P5 sequence (upper case) and the forward Illumina sequencing primer (lower case). The primers labeled with P7 truseq contain the P7 sequence (upper case), a TruSeq barcode (bolt upper case) and the reverse Illumina sequencing primer (lower case).

| Primer | Sequence | SEQ ID NO: |
|---|---|---|
| Guide3 Amp1FW | CCTACACGACGCTCTTCCGATCT<br>GGTCCCGGTCAGGTTAACTCTGTAATAATC | 29 |
| Guide3 Amp1rev | AGTTCAGACGTGTGCTCTTCCGATCT<br>GTGAGTGCAGGCAGGCAGG | 30 |
| Guide1 Amp1FW | CCTACACGACGCTCTTCCGATCT<br>CCGCTCACCACGGAAGGC | 31 |
| Guide1 Amp1rev | AGTTCAGACGTGTGCTCTTCCGATCT<br>GCCTCAGCCACCTCTGAGACTCTG | 32 |
| Universal primer P5 | AATGATACGGCGACCACCGAGATCT<br>acactctttccctacacgacgctcttccgatct | 33 |
| P7 truseq 13 | CAAGCAGAAGACGGCATACGAGATTTGACT<br>gtgactggagttcagacgtgtgctcttccgatct | 34 |

TABLE 10-continued

Primers used to attach Illumina sequencing primers to the target regions of interest. The first four primers contain a target specific part and part of the Illumina sequencing primer (indicated in bold) as intermediate adapter. In a second PCR this intermediate adapter was used to fuse the full size Illumina adaptors to the amplicon, by using the Universal primer P5 and the different P7 truseq primers. The universal primer P5 contains the P5 sequence (upper case) and the forward Illumina sequencing primer (lower case). The primers labeled with P7 truseq contain the P7 sequence (upper case), a TruSeq barcode (bolt upper case) and the reverse Illumina sequencing primer (lower case).

| Primer | Sequence | SEQ ID NO: |
|---|---|---|
| P7 truseq 14 | CAAGCAGAAGACGGCATACGAGATGGAACT<br>gtgactggagttcagacgtgtgctcttccgatct | 35 |
| P7 truseq 15 | CAAGCAGAAGACGGCATACGAGATTGACAT<br>gtgactggagttcagacgtgtgctcttccgatct | 36 |
| P7 truseq 16 | CAAGCAGAAGACGGCATACGAGATGGACGG<br>gtgactggagttcagacgtgtgctcttccgatct | 37 |
| P7 truseq 18 | CAAGCAGAAGACGGCATACGAGATGCGGAC<br>gtgactggagttcagacgtgtgctcttccgatct | 38 |
| P7 truseq 19 | CAAGCAGAAGACGGCATACGAGATTTTCAC<br>gtgactggagttcagacgtgtgctcttccgatct | 39 |
| P7 truseq 20 | CAAGCAGAAGACGGCATACGAGATGGCCAC<br>gtgactggagttcagacgtgtgctcttccgatct | 40 |
| P7 truseq 21 | CAAGCAGAAGACGGCATACGAGATCGAAAC<br>gtgactggagttcagacgtgtgctcttccgatct | 41 |
| P7 truseq 22 | CAAGCAGAAGACGGCATACGAGATCGTACG<br>gtgactggagttcagacgtgtgctcttccgatct | 42 |
| P7 truseq 23 | CAAGCAGAAGACGGCATACGAGATCCACTC<br>gtgactggagttcagacgtgtgctcttccgatct | 43 |
| P7 truseq 25 | CAAGCAGAAGACGGCATACGAGATATCAGT<br>gtgactggagttcagacgtgtgctcttccgatct | 44 |
| P7 truseq 27 | CAAGCAGAAGACGGCATACGAGATAGGAAT<br>gtgactggagttcagacgtgtgctcttccgatct | 45 |
| P7 truseq 28 | CAAGCAGAAGACGGCATACGAGATCTTTTG<br>gtgactggagttcagacgtgtgctcttccgatct | 46 |

SDS-PAGE and Western Blots

Proteins samples were separated on 12% Tricin SDS-PAGE gels, prepared as previously described (DeAngelis, M. M., Wang, D. G. & Hawkins, T. L. Solid-phase reversible immobilization for the isolation of PCR products. *Nucleic Acids Res.* 23:4742-4743 (1995)). The samples were transferred to a nitrocellulose membrane (Schleicher & Schuell, Munchen, Germany) using a TE70X semi dry transfer unit (Hoefer, Holliston, Mass., USA) according to the manufacturer's instructions. Next, the blots were blocked with PBS containing 0.05% (wt/vol) TWEEN®20 and 3% (wt/vol) milk powder for one hour. To visualize the hGM-CSF, a DyLight 800 coupled 6xHis tag antibody (Catalog number 200-345-382, Rockland, Limerick, Pa., USA) was added in a 1/15000 dilution and incubated for 1 hour. After three wash steps with PBS+0.05% TWEEN®20 the blot was visualized using the odyssey scanner (LI-COR biosciences, Lincoln, Nebr., USA).

The invention claimed is:

1. A eukaryotic cell comprising an exogenous nucleic acid sequence encoding an endoglucosaminidase enzyme;
   wherein the endoglucosaminidase is an endo-beta-N-acetylglucosaminidase of EC class 3.2.1.96; and
   wherein the eukaryotic cell is a UDP-galactose 4-epimerase (GalE) knockout cell.

2. The eukaryotic cell according to claim 1, further comprising a second exogenous nucleic acid sequence encoding a glycoprotein.

3. The eukaryotic cell according to claim 2, which does not express an endogenous endoglucosaminidase enzyme.

4. The eukaryotic cell according to claim 1, which is a mammalian cell.

5. The eukaryotic cell according to claim 2, wherein the glycoprotein is secreted by the eukaryotic cell.

6. A method for producing glycoproteins in a eukaryotic cell, wherein N-glycans present on the glycoproteins consist only of a single GlcNAc residue and the glycoproteins also lack O-glycosylation, the method comprising the steps of:
   providing the eukaryotic cell of claim 2 in conditions suitable for expressing the endoglucosaminidase enzyme and the glycoprotein; and
   recovering the glycoprotein.

7. The method according to claim 6, further comprising a step of having the glycoprotein processed by a glycosyltransferase after contact with the endoglucosaminidase.

8. The eukaryotic cell of claim 4, wherein the mammalian cell is a Hek293 cell or a CHO cell.

9. The eukaryotic cell of claim 1, wherein the endoglucosaminidase is Endo T.

10. The eukaryotic cell of claim 2, which is a mammalian cell.

* * * * *